United States Patent
Depla et al.

(10) Patent No.: US 6,635,257 B1
(45) Date of Patent: Oct. 21, 2003

(54) PARTICLES OF HCV ENVELOPE PROTEINS: USE FOR VACCINATION

(75) Inventors: Erik Depla, Destelbergen (BE); Geert Maertens, Brugge (BE); Alfons Bosman, Opwiik (BE); Frans Van Wijnendaele, Laarne (BE)

(73) Assignee: Innogentics N.V., Ghent (BE)

( * ) Notice: Subject to any disclaimer, the term of this patent is extended or adjusted under 35 U.S.C. 154(b) by 0 days.

(21) Appl. No.: 09/355,040

(22) PCT Filed: Jun. 23, 1999

(86) PCT No.: PCT/EP99/04342

§ 371 (c)(1), (2), (4) Date: Jul. 23, 1999

(87) PCT Pub. No.: WO99/67285

PCT Pub. Date: Dec. 29, 1999

(30) Foreign Application Priority Data

Jun. 24, 1998 (EP) .............................................. 98870142
Feb. 22, 1999 (EP) .............................................. 99870033

(51) Int. Cl.[7] .............................................. A61K 39/29
(52) U.S. Cl. ................................ 424/228.1; 424/185.1; 435/5; 435/69.1; 435/235.1; 530/350; 530/826
(58) Field of Search .......................... 424/185.1, 228.1; 435/5, 69.1, 235.1; 530/826, 350

(56) References Cited

U.S. PATENT DOCUMENTS 5,942,234 A * 8/1999 Ralston et al. ............ 424/228.1
6,150,134 A * 11/2000 Maertens et al. .......... 435/69.3

FOREIGN PATENT DOCUMENTS

WO    WO 96 04385 A    2/1996
WO    WO 98 21338 A    5/1998

OTHER PUBLICATIONS

Baumert et al. Hepatitis C virus structural proteins assemble into virus like particles in insect cells. Journal of Virology (May 1998) vol. 72, No. 5, pp. 3827–3836.*
Ristori et al. Compositional bias and mimicry toward the nonself proteome in immunodominant T cell epitopes of self and nonself antigens. FASEB (2000) vol. 14, No. 3, pp. 431–438.*
Paul, Fundamental Immunology, Raven Press, New York, NY; 1993, 3rd Edition, p. 251, column 1, lines 11–12.*
Bosman F et al: Purification of the hepatitis C virus envelope proteins and analysis of their oligomeric state. 48th Annual Meeting of the American Association for the Study of Liver Diseases, Chicago, Illinois, USA, Nov. 7–11, 1997. Hepatology 26 (4 Part 2). 1997. 412A, XP002087226 see abstract 1136.

* cited by examiner

Primary Examiner—James Housel
Assistant Examiner—Ulrike Winkler
(74) Attorney, Agent, or Firm—Nixon & Vanderhye

(57) ABSTRACT

The present invention is based on the finding that the envelope proteins of HCV induce a beneficial immune response in chronically HCV-infected chimpanzees. The immunization can preferentially be carried out using HCV envelope proteins in the form of particles which are produced in a detergent-assisted manner. The envelope proteins when presented as such to chronic HCV carriers are highly immunogenic and stimulate both the cellular and humoral immune response.

28 Claims, 38 Drawing Sheets

Ton epitope mapping E1 response

Figure 1:
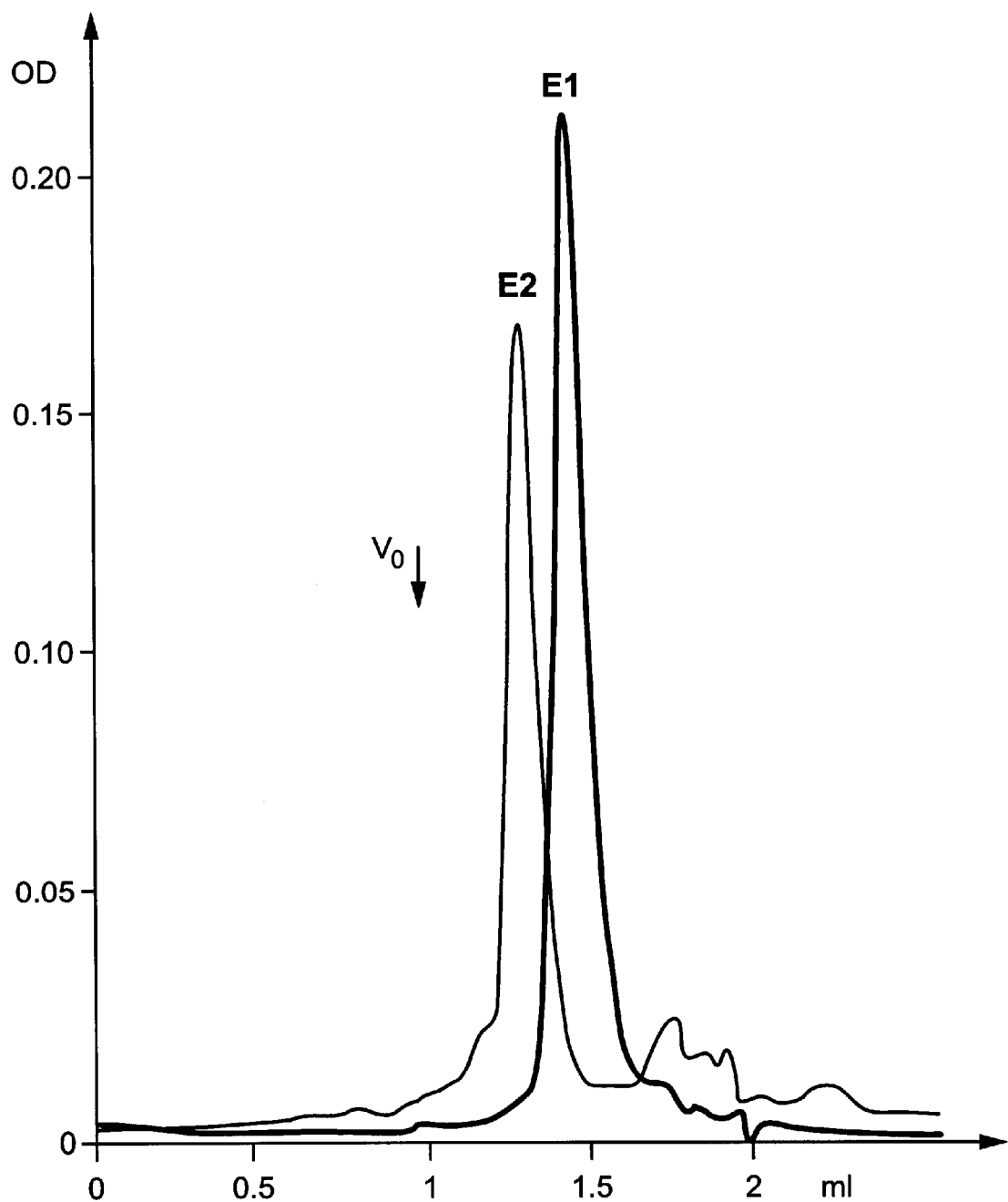

- E1
- V1V2
- V2V3
- V3V4
- V4V5
- V5C4
- C4V6

Figure 12

TON (Subtype 1a)

Crossreactivity of vaccine-induced E1Ab on E1-1a and E1-1b

Figure 13 days post first immunization

```
  1  AGCTTTTGCG  ATCAATAAAT  GGATCACAAC  CAGTATCTCT  TAACGATGTT
     TCGAAAACGC  TAGTTATTTA  CCTAGTGTTG  GTCATAGAGA  ATTGCTACAA

51  CTTCGCAGAT  GATGATTCAT  TTTTTAAGTA  TTTGGCTAGT  CAAGATGATG
     GAAGCGTCTA  CTACTAAGTA  AAAAATTCAT  AAACCGATCA  GTTCTACTAC

101  AATCTTCATT  ATCTGATATA  TTGCAAATCA  CTCAATATCT  AGACTTTCTG
     TTAGAAGTAA  TAGACTATAT  AACGTTTAGT  GAGTTATAGA  TCTGAAAGAC

151  TTATTATTAT  TGATCCAATC  AAAAAATAAA  TTAGAAGCCG  TGGGTCATTG
     AATAATAATA  ACTAGGTTAG  TTTTTTATTT  AATCTTCGGC  ACCCAGTAAC

201  TTATGAATCT  CTTTCAGAGG  AATACAGACA  ATTGACAAAA  TTCACAGACT
     AATACTTAGA  GAAAGTCTCC  TTATGTCTGT  TAACTGTTTT  AAGTGTCTGA

251  TTCAAGATTT  TAAAAACTG   TTTAACAAGG  TCCCTATTGT  TACAGATGGA
     AAGTTCTAAA  ATTTTTTGAC  AAATTGTTCC  AGGGATAACA  ATGTCTACCT

301  AGGGTCAAAC  TTAATAAAGG  ATATTTGTTC  GACTTTGTGA  TTAGTTTGAT
     TCCCAGTTTG  AATTATTTCC  TATAAACAAG  CTGAAACACT  AATCAAACTA

351  GCGATTCAAA  AAAGAATCCT  CTCTAGCTAC  CACCGCAATA  GATCCTGTTA
     CGCTAAGTTT  TTTCTTAGGA  GAGATCGATG  GTGGCGTTAT  CTAGGACAAT

401  GATACATAGA  TCCTCGTCGC  AATATCGCAT  TTTCTAACGT  GATGGATATA
     CTATGTATCT  AGGAGCAGCG  TTATAGCGTA  AAAGATTGCA  CTACCTATAT

451  TTAAAGTCGA  ATAAAGTGAA  CAATAATTAA  TTCTTTATTG  TCATCATGAA
     AATTTCAGCT  TATTTCACTT  GTTATTAATT  AAGAAATAAC  AGTAGTACTT

501  CGGCGGACAT  ATTCAGTTGA  TAATCGGCCC  CATGTTTTCA  GGTAAAAGTA
     GCCGCCTGTA  TAAGTCAACT  ATTAGCCGGG  GTACAAAAGT  CCATTTTCAT

551  CAGAATTAAT  TAGACGAGTT  AGACGTTATC  AAATAGCTCA  ATATAAATGC
     GTCTTAATTA  ATCTGCTCAA  TCTGCAATAG  TTTATCGAGT  TATATTTACG

601  GTGACTATAA  AATATTCTAA  CGATAATAGA  TACGGAACGG  GACTATGGAC
     CACTGATATT  TTATAAGATT  GCTATTATCT  ATGCCTTGCC  CTGATACCTG

651  GCATGATAAG  AATAATTTTG  AAGCATTGGA  AGCAACTAAA  CTATGTGATG
     CGTACTATTC  TTATTAAAAC  TTCGTAACCT  TCGTTGATTT  GATACACTAC

701  TCTTGGAATC  AATTACAGAT  TTCTCCGTGA  TAGGATACTC  ATAAATCCAG
     AGAACCTTAG  TTAATGTCTA  AAGAGGCACT  ATCCTATGAG  TATTTAGGTC
```

Figure 16a

```
 751   TTGCCGCCAC  GGTAGCCAAT  CACCGTATCG  TATAAATCAT  CGTCGGTACG
       AACGGCGGTG  CCATCGGTTA  GTGGCATAGC  ATATTTAGTA  GCAGCCATGC

801   TTCGGCATCG  CTCATCACAA  TACGTGCCTG  GACGTCGAGG  ATTTCGCGTG
       AAGCCGTAGC  GAGTAGTGTT  ATGCACGGAC  CTGCAGCTCC  TAAAGCGCAC

851   GGTCAATGCC  GCGCCAGATC  CACATCAGAC  GGTTAATCAT  GCGATACCAG
       CCAGTTACGG  CGCGGTCTAG  GTGTAGTCTG  CCAATTAGTA  CGCTATGGTC

901   TGAGGGATGG  TTTTACCATC  AAGGGCCGAC  TGCACAGGCG  GTTGTGCGCC
       ACTCCCTACC  AAAATGGTAG  TTCCCGGCTG  ACGTGTCCGC  CAACACGCGG

951   GTGATTAAAG  CGGCGGACTA  GCGTCGAGGT  TTCAGGATGT  TTAAAGCGGG
       CACTAATTTC  GCCGCCTGAT  CGCAGCTCCA  AAGTCCTACA  AATTTCGCCC

1001   GTTTGAACAG  GGTTTCGCTC  AGGTTTGCCT  GTGTCATGGA  TGCAGCCTCC
       CAAACTTGTC  CCAAAGCGAG  TCCAAACGGA  CACAGTACCT  ACGTCGGAGG

1051   AGAATACTTA  CTGGAAACTA  TTGTAACCCG  CCTGAAGTTA  AAAAGAACAA
       TCTTATGAAT  GACCTTTGAT  AACATTGGGC  GGACTTCAAT  TTTTCTTGTT

1101   CGCCCGGCAG  TGCCAGGCGT  TGAAAAGATT  AGCGACCGGA  GATTGGCGGG
       GCGGGCCGTC  ACGGTCCGCA  ACTTTTCTAA  TCGCTGGCCT  CTAACCGCCC

1151   ACGAATACGA  CGCCCATATC  CCACGGCTGT  TCAATCCAGG  TATCTTGCGG
       TGCTTATGCT  GCGGGTATAG  GGTGCCGACA  AGTTAGGTCC  ATAGAACGCC

1201   GATATCAACA  ACATAGTCAT  CAACCAGCGG  ACGACCAGCC  GGTTTTGCGA
       CTATAGTTGT  TGTATCAGTA  GTTGGTCGCC  TGCTGGTCGG  CCAAAACGCT

1251   AGATGGTGAC  AAAGTGCGCT  TTTGGATACA  TTTCACGAAT  CGCAACCGCA
       TCTACCACTG  TTTCACGCGA  AAACCTATGT  AAAGTGCTTA  GCGTTGGCGT

1301   GTACCACCGG  TATCCACCAG  GTCATCAATA  ACGATGAAGC  CTTCGCCATC
       CATGGTGGCC  ATAGGTGGTC  CAGTAGTTAT  TGCTACTTCG  GAAGCGGTAG

1351   GCCTTCTGCG  CGTTTCAGCA  CTTTAAGCTC  GCGCTGGTTG  TCGTGATCGT
       CGGAAGACGC  GCAAAGTCGT  GAAATTCGAG  CGCGACCAAC  AGCACTAGCA

1401   AGCTGGAAAT  ACAAACGGTA  TCGACATGAC  GAATACCCAG  TTCACGCGCC
       TCGACCTTTA  TGTTTGCCAT  AGCTGTACTG  CTTATGGGTC  AAGTGCGCGG

1451   AGTAACGCAC  CCGGTACCAG  ACCGCCACGG  CTTACGGCAA  TAATGCCTTT
       TCATTGCGTG  GGCCATGGTC  TGGCGGTGCC  GAATGCCGTT  ATTACGGAAA
```

Figure 16a-1

```
1501  CCATTGTTCA GAAGGCATCA GTCGGCTTGC GAGTTTACGT GCATGGATCT
      GGTAACAAGT CTTCCGTAGT CAGCCGAACG CTCAAATGCA CGTACCTAGA

1551  GCAACATGTC CCAGGTGACG ATGTATTTTT CGCTCATGTG AAGTGTCCCA
      CGTTGTACAG GGTCCACTGC TACATAAAAA GCGAGTACAC TTCACAGGGT

1601  GCCTGTTTAT CTACGGCTTA AAAAGTGTTC GAGGGGAAAA TAGGTTGCGC
      CGGACAAATA GATGCCGAAT TTTTCACAAG CTCCCCTTTT ATCCAACGCG

1651  GAGATTATAG GGCCTTACTT TGTAATATAA TGATATATAT TTTCACTTTA
      CTCTAATATC CCGGAATGAA ACATTATATT ACTATATATA AAAGTGAAAT

1701  TCTCATTTGA GAATAAAAAT GTTTTTGTTT AACCACTGCA TGATGTCAAT
      AGAGTAAACT CTTATTTTTA CAAAAACAAA TTGGTGACGT ACTACAGTTA

1751  TCCGATCCTA GAAGCGATGC TACGCTAGTC ACAATCACCA CTTTCATATT
      AGGCTAGGAT CTTCGCTACG ATGCGATCAG TGTTAGTGGT GAAAGTATAA

1801  TAGAATATAT GTATGTAAAA ATATAGTAGA ATTTCATTTT GTTTTTTTCT
      ATCTTATATA CATACATTTT TATATCATCT AAAGTAAAA CAAAAAAAGA

1851  ATCGATTAAA TAGAATTCGA GCTCGGTACC CGGGGATCCC ACAAGCTGTC
      TAGCTAATTT ATCTTAAGCT CGAGCCATGG GCCCCTAGGG TGTTCGACAG

1901  GTGGACATGG TGGCGGGGGC CCATTGGGGA GTCCTGGCGG GTCTCGCCTA
      CACCTGTACC ACCGCCCCG GGTAACCCCT CAGGACCGCC CAGAGCGGAT

1951  CTATTCCATG GTGGGGAACT GGGCTAAGGT TTTGATTGTG ATGCTACTCT
      GATAAGGTAC CACCCCTTGA CCCGATTCCA AAACTAACAC TACGATGAGA

2001  TTGCCGGCGT CGACGGGCAT ACCCGCGTGT CAGGAGGGGC AGCAGCCTCC
      AACGGCCGCA GCTGCCCGTA TGGGCGCACA GTCCTCCCCG TCGTCGGAGG

2051  GATACCAGGG GCCTTGTGTC CCTCTTTAGC CCCGGGTCGG CTCAGAAAAT
      CTATGGTCCC CGGAACACAG GGAGAAATCG GGCCCAGCC GAGTCTTTTA

2101  CCAGCTCGTA AACACCAACG GCAGTTGGCA CATCAACAGG ACTGCCCTGA
      GGTCGAGCAT TTGTGGTTGC CGTCAACCGT GTAGTTGTCC TGACGGGACT

2151  ACTGCAACGA CTCCCTCCAA ACAGGGTTCT TGCCGCACT ATTCTACAAA
      TGACGTTGCT GAGGGAGGTT TGTCCCAAGA AACGGCGTGA TAAGATGTTT

2201  CACAAATTCA ACTCGTCTGG ATGCCCAGAG CGCTTGGCCA GCTGTCGCTC
      GTGTTTAAGT TGAGCAGACC TACGGGTCTC GCGAACCGGT CGACAGCGAG
```

Figure 16a-2

```
2251 CATCGACAAG TTCGCTCAGG GGTGGGGTCC CCTCACTTAC ACTGAGCCTA
     GTAGCTGTTC AAGCGAGTCC CCACCCCAGG GGAGTGAATG TGACTCGGAT

2301 ACAGCTCGGA CCAGAGGCCC TACTGCTGGC ACTACGCGCC TCGACCGTGT
     TGTCGAGCCT GGTCTCCGGG ATGACGACCG TGATGCGCGG AGCTGGCACA

2351 GGTATTGTAC CCGCGTCTCA GGTGTGCGGT CCAGTGTATT GCTTCACCCC
     CCATAACATG GGCGCAGAGT CCACACGCCA GGTCACATAA CGAAGTGGGG

2401 GAGCCCTGTT GTGGTGGGGA CGACCGATCG GTTTGGTGTC CCCACGTATA
     CTCGGGACAA CACCACCCCT GCTGGCTAGC CAAACCACAG GGGTGCATAT

2451 ACTGGGGGGC GAACGACTCG GATGTGCTGA TTCTCAACAA CACGCGGCCG
     TGACCCCCCG CTTGCTGAGC CTACACGACT AAGAGTTGTT GTGCGCCGGC

2501 CCGCGAGGCA ACTGGTTCGG CTGTACATGG ATGAATGGCA CTGGGTTCAC
     GGCGCTCCGT TGACCAAGCC GACATGTACC TACTTACCGT GACCCAAGTG

2551 CAAGACGTGT GGGGCCCCCC CGTGCAACAT CGGGGGGGCC GGCAACAACA
     GTTCTGCACA CCCCGGGGG GCACGTTGTA GCCCCCCGG CCGTTGTTGT

2601 CCTTGACCTG CCCCACTGAC TGTTTTCGGA AGCACCCCGA GGCCACCTAC
     GGAACTGGAC GGGGTGACTG ACAAAAGCCT TCGTGGGCT CCGGTGGATG

2651 GCCAGATGCG GTTCTGGGCC CTGGCTGACA CCTAGGTGTA TGGTTCATTA
     CGGTCTACGC CAAGACCCGG GACCGACTGT GGATCCACAT ACCAAGTAAT

2701 CCCATATAGG CTCTGGCACT ACCCCTGCAC TGTCAACTTC ACCATCTTCA
     GGGTATATCC GAGACCGTGA TGGGACGTG ACAGTTGAAG TGGTAGAAGT

2751 AGGTTAGGAT GTACGTGGGG GGCGTGGAGC ACAGGTTCGA AGCCGCATGC
     TCCAATCCTA CATGCACCCC CCGCACCTCG TGTCCAAGCT TCGGCGTACG

2801 AATTGGACTC GAGGAGAGCG TTGTGACTTG GAGGACAGGG ATAGATCAGA
     TTAACCTGAG CTCCTCTCGC AACACTGAAC CTCCTGTCCC TATCTAGTCT

2851 GCTTAGCCCG CTGCTGCTGT CTACAACAGA GTGGCAGATA CTGCCCTGTT
     CGAATCGGGC GACGACGACA GATGTTGTCT CACCGTCTAT GACGGGACAA

2901 CCTTCACCAC CCTGCCGGCC CTATCCACCG GCCTGATCCA CCTCCATCAG
     GGAAGTGGTG GGACGGCCGG GATAGGTGGC CGGACTAGGT GGAGGTAGTC

2951 AACATCGTGG ACGTGCAATA CCTGTACGGT GTAGGGTCGG CGGTTGTCTC
     TTGTAGCACC TGCACGTTAT GGACATGCCA CATCCCAGCC GCCAACAGAG
```

Figure 16a-3

```
3001  CCTTGTCATC  AAATAAGCTT  AATTAATTAG  CTTGGGATCG  GCTGTGAGCG
      GGAACAGTAG  TTTATTCGAA  TTAATTAATC  GAACCCTAGC  CGACACTCGC

3051  TATGGCAAAC  GAAGGAAAAA  TAGTTATAGT  AGCCGCACTC  GATGGGACAT
      ATACCGTTTG  CTTCCTTTTT  ATCAATATCA  TCGGCGTGAG  CTACCCTGTA

3101  TTCAACGTAA  ACCGTTTAAT  AATATTTTGA  ATCTTATTCC  ATTATCTGAA
      AAGTTGCATT  TGGCAAATTA  TTATAAAACT  TAGAATAAGG  TAATAGACTT

3151  ATGGTGGTAA  AACTAACTGC  TGTGTGTATG  AAATGCTTTA  AGGAGGCTTC
      TACCACCATT  TTGATTGACG  ACACACATAC  TTTACGAAAT  TCCTCCGAAG

3201  CTTTTCTAAA  CGATTGGGTG  AGGAAACCGA  GATAGAAATA  ATAGGAGGTA
      GAAAAGATTT  GCTAACCCAC  TCCTTTGGCT  CTATCTTTAT  TATCCTCCAT

3251  ATGATATGTA  TCAATCGGTG  TGTAGAAAGT  GTTACATCGA  CTCATAATAT
      TACTATACAT  AGTTAGCCAC  ACATCTTTCA  CAATGTAGCT  GAGTATTATA

3301  TATATTTTTT  ATCTAAAAAA  CTAAAAATAA  ACATTGATTA  AATTTTAATA
      ATATAAAAAA  TAGATTTTTT  GATTTTTATT  TGTAACTAAT  TTAAAATTAT

3351  TAATACTTAA  AAATGGATGT  TGTGTCGTTA  GATAAACCGT  TTATGTATTT
      ATTATGAATT  TTTACCTACA  ACACAGCAAT  CTATTTGGCA  AATACATAAA

3401  TGAGGAAATT  GATAATGAGT  TAGATTACGA  ACCAGAAAGT  GCAAATGAGG
      ACTCCTTTAA  CTATTACTCA  ATCTAATGCT  TGGTCTTTCA  CGTTTACTCC

3451  TCGCAAAAAA  ACTGCCGTAT  CAAGGACAGT  TAAAACTATT  ACTAGGAGAA
      AGCGTTTTTT  TGACGGCATA  GTTCCTGTCA  ATTTTGATAA  TGATCCTCTT

3501  TTATTTTTTC  TTAGTAAGTT  ACAGCGACAC  GGTATATTAG  ATGGTGCCAC
      AATAAAAAAG  AATCATTCAA  TGTCGCTGTG  CCATATAATC  TACCACGGTG

3551  CGTAGTGTAT  ATAGGATCTG  CTCCCGGATC  GATCCTGCAT  TAATGAATCG
      GCATCACATA  TATCCTAGAC  GAGGGCCTAG  CTAGGACGTA  ATTACTTAGC

3601  GCCAACGCGC  GGGGAGAGGC  GGTTTGCGTA  TTGGGCTTCC  TCGCTGCGCT
      CGGTTGCGCG  CCCCTCTCCG  CCAAACGCAT  AACCCGAAGG  AGCGACGCGA

3651  CGGTCGTTCG  GCTGCGGCGA  GCGGTATCAG  CTCACTCAAA  GGCGGTAATA
      GCCAGCAAGC  CGACGCCGCT  CGCCATAGTC  GAGTGAGTTT  CCGCCATTAT

3701  CGGTTATCCA  CAGAATCAGG  GGATAACGCA  GGAAAGAACA  TGTGAGCAAA
      GCCAATAGGT  GTCTTAGTCC  CCTATTGCGT  CCTTTCTTGT  ACACTCGTTT
```

Figure 16a-4

```
3751  AGGCCAGCAA  AAGGCCAGGA  ACCGTAAAAA  GGCCGCGTTG  CTGGCGTTTT
      TCCGGTCGTT  TTCCGGTCCT  TGGCATTTTT  CCGGCGCAAC  GACCGCAAAA

3801  TCCATAGGCT  CCGCCCCCT   GACGAGCATC  ACAAAAATCG  ACGCTCAAGT
      AGGTATCCGA  GGCGGGGGGA  CTGCTCGTAG  TGTTTTTAGC  TGCGAGTTCA

3851  CAGAGGTGGC  GAAACCCGAC  AGGACTATAA  AGATACCAGG  CGTTTCCCCC
      GTCTCCACCG  CTTTGGGCTG  TCCTGATATT  TCTATGGTCC  GCAAAGGGGG

3901  TGGAAGCTCC  CTCGTGCGCT  CTCCTGTTCC  GACCCTGCCG  CTTACCGGAT
      ACCTTCGAGG  GAGCACGCGA  GAGGACAAGG  CTGGGACGGC  GAATGGCCTA

3951  ACCTGTCCGC  CTTTCTCCCT  TCGGGAAGCG  TGGCGCTTTC  TCATAGCTCA
      TGGACAGGCG  GAAAGAGGGA  AGCCCTTCGC  ACCGCGAAAG  AGTATCGAGT

4001  CGCTGTAGGT  ATCTCAGTTC  GGTGTAGGTC  GTTCGCTCCA  AGCTGGGCTG
      GCGACATCCA  TAGAGTCAAG  CCACATCCAG  CAAGCGAGGT  TCGACCCGAC

4051  TGTGCACGAA  CCCCCCGTTC  AGCCCGACCG  CTGCGCCTTA  TCCGGTAACT
      ACACGTGCTT  GGGGGGCAAG  TCGGGCTGGC  GACGCGGAAT  AGGCCATTGA

4101  ATCGTCTTGA  GTCCAACCCG  GTAAGACACG  ACTTATCGCC  ACTGGCAGCA
      TAGCAGAACT  CAGGTTGGGC  CATTCTGTGC  TGAATAGCGG  TGACCGTCGT

4151  GCCACTGGTA  ACAGGATTAG  CAGAGCGAGG  TATGTAGGCG  GTGCTACAGA
      CGGTGACCAT  TGTCCTAATC  GTCTCGCTCC  ATACATCCGC  CACGATGTCT

4201  GTTCTTGAAG  TGGTGGCCTA  ACTACGGCTA  CACTAGAAGA  ACAGTATTTG
      CAAGAACTTC  ACCACCGGAT  TGATGCCGAT  GTGATCTTCT  TGTCATAAAC

4251  GTATCTGCGC  TCTGCTGAAG  CCAGTTACCT  TCGGAAAAAG  AGTTGGTAGC
      CATAGACGCG  AGACGACTTC  GGTCAATGGA  AGCCTTTTTC  TCAACCATCG

4301  TCTTGATCCG  GCAAACAAAC  CACCGCTGGT  AGCGGTGGTT  TTTTTGTTTG
      AGAACTAGGC  CGTTTGTTTG  GTGGCGACCA  TCGCCACCAA  AAAAACAAAC

4351  CAAGCAGCAG  ATTACGCGCA  GAAAAAAAGG  ATCTCAAGAA  GATCCTTTGA
      GTTCGTCGTC  TAATGCGCGT  CTTTTTTTCC  TAGAGTTCTT  CTAGGAAACT

4401  TCTTTTCTAC  GGGGTCTGAC  GCTCAGTGGA  ACGAAAACTC  ACGTTAAGGG
      AGAAAAGATG  CCCCAGACTG  CGAGTCACCT  TGCTTTTGAG  TGCAATTCCC

4451  ATTTTGGTCA  TGAGATTATC  AAAAAGGATC  TTCACCTAGA  TCCTTTTAAA
      TAAAACCAGT  ACTCTAATAG  TTTTTCCTAG  AAGTGGATCT  AGGAAAATTT
```

Figure 16a-5

```
4501  TTAAAAATGA AGTTTTAAAT CAATCTAAAG TATATATGAG TAAACTTGGT
      AATTTTTACT TCAAAATTTA GTTAGATTTC ATATATACTC ATTTGAACCA

4551  CTGACAGTTA CCAATGCTTA ATCAGTGAGG CACCTATCTC AGCGATCTGT
      GACTGTCAAT GGTTACGAAT TAGTCACTCC GTGGATAGAG TCGCTAGACA

4601  CTATTTCGTT CATCCATAGT TGCCTGACTC CCCGTCGTGT AGATAACTAC
      GATAAAGCAA GTAGGTATCA ACGGACTGAG GGGCAGCACA TCTATTGATG

4651  GATACGGGAG GGCTTACCAT CTGGCCCCAG TGCTGCAATG ATACCGCGAG
      CTATGCCCTC CCGAATGGTA GACCGGGGTC ACGACGTTAC TATGGCGCTC

4701  ACCCACGCTC ACCGGCTCCA GATTTATCAG CAATAAACCA GCCAGCCGGA
      TGGGTGCGAG TGGCCGAGGT CTAAATAGTC GTTATTTGGT CGGTCGGCCT

4751  AGGGCCGAGC GCAGAAGTGG TCCTGCAACT TTATCCGCCT CCATCCAGTC
      TCCCGGCTCG CGTCTTCACC AGGACGTTGA AATAGGCGGA GGTAGGTCAG

4801  TATTAATTGT TGCCGGGAAG CTAGAGTAAG TAGTTCGCCA GTTAATAGTT
      ATAATTAACA ACGGCCCTTC GATCTCATTC ATCAAGCGGT CAATTATCAA

4851  TGCGCAACGT TGTTGCCATT GCTACAGGCA TCGTGGTGTC ACGCTCGTCG
      ACGCGTTGCA ACAACGGTAA CGATGTCCGT AGCACCACAG TGCGAGCAGC

4901  TTTGGTATGG CTTCATTCAG CTCCGGTTCC CAACGATCAA GGCGAGTTAC
      AAACCATACC GAAGTAAGTC GAGGCCAAGG GTTGCTAGTT CCGCTCAATG

4951  ATGATCCCCC ATGTTGTGCA AAAAAGCGGT TAGCTCCTTC GGTCCTCCGA
      TACTAGGGGG TACAACACGT TTTTTCGCCA ATCGAGGAAG CCAGGAGGCT

5001  TCGTTGTCAG AAGTAAGTTG GCCGCAGTGT TATCACTCAT GGTTATGGCA
      AGCAACAGTC TTCATTCAAC CGGCGTCACA ATAGTGAGTA CCAATACCGT

5051  GCACTGCATA ATTCTCTTAC TGTCATGCCA TCCGTAAGAT GCTTTTCTGT
      CGTGACGTAT TAAGAGAATG ACAGTACGGT AGGCATTCTA CGAAAAGACA

5101  GACTGGTGAG TACTCAACCA AGTCATTCTG AGAATAGTGT ATGCGGCGAC
      CTGACCACTC ATGAGTTGGT TCAGTAAGAC TCTTATCACA TACGCCGCTG

5151  CGAGTTGCTC TTGCCCGGCG TCAATACGGG ATAATACCGC GCCACATAGC
      GCTCAACGAG AACGGGCCGC AGTTATGCCC TATTATGGCG CGGTGTATCG

5201  AGAACTTTAA AAGTGCTCAT CATTGGAAAA CGTTCTTCGG GGCGAAAACT
      TCTTGAAATT TTCACGAGTA GTAACCTTTT GCAAGAAGCC CCGCTTTTGA
```

Figure 16a-6

```
5251  CTCAAGGATC TTACCGCTGT TGAGATCCAG TTCGATGTAA CCCACTCGTG
      GAGTTCCTAG AATGGCGACA ACTCTAGGTC AAGCTACATT GGGTGAGCAC

5301  CACCCAACTG ATCTTCAGCA TCTTTTACTT TCACCAGCGT TTCTGGGTGA
      GTGGGTTGAC TAGAAGTCGT AGAAAATGAA AGTGGTCGCA AAGACCCACT

5351  GCAAAAACAG GAAGGCAAAA TGCCGCAAAA AAGGGAATAA GGGCGACACG
      CGTTTTTGTC CTTCCGTTTT ACGGCGTTTT TTCCCTTATT CCCGCTGTGC

5401  GAAATGTTGA ATACTCATAC TCCTCCTTTT TCAATATTAT TGAAGCATTT
      CTTTACAACT TATGAGTATG AGGAGGAAAA AGTTATAATA ACTTCGTAAA

5451  ATCAGGGTTA TTGTCTCATG AGCGGATACA TATTTGAATG TATTTAGAAA
      TAGTCCCAAT AACAGAGTAC TCGCCTATGT ATAAACTTAC ATAAATCTTT

5501  AATAAACAAA TAGGGGTTCC GCGCACATTT CCCCGAAAAG TGCCACCTGA
      TTATTTGTTT ATCCCCAAGG CGCGTGTAAA GGGGCTTTTC ACGGTGGACT

5551  CGTCTAAGAA ACCATTATTA TCATGACATT AACCTATAAA AATAGGCGTA
      GCAGATTCTT TGGTAATAAT AGTACTGTAA TTGGATATTT TTATCCGCAT

5601  TCACGAGGCC CTTTCGTCTC GCGCGTTTCG GTGATGACGG TGAAAACCTC
      AGTGCTCCGG GAAAGCAGAG CGCGCAAAGC CACTACTGCC ACTTTTGGAG

5651  TGACACATGC AGCTCCCGGA GACGGTCACA GCTTGTCTGT AAGCGGATGC
      ACTGTGTACG TCGAGGGCCT CTGCCAGTGT CGAACAGACA TTCGCCTACG

5701  CGGGAGCAGA CAAGCCCGTC AGGGCGCGTC AGCGGGTGTT GGCGGGTGTC
      GCCCTCGTCT GTTCGGGCAG TCCCGCGCAG TCGCCCACAA CCGCCCACAG

5751  GGGGCTGGCT TAACTATGCG GCATCAGAGC AGATTGTACT GAGAGTGCAC
      CCCCGACCGA ATTGATACGC CGTAGTCTCG TCTAACATGA CTCTCACGTG

5801  CATATGCGGT GTGAAATACC GCACAGATGC GTAAGGAGAA AATACCGCAT
      GTATACGCCA CACTTTATGG CGTGTCTACG CATTCCTCTT TTATGGCGTA

5851  CAGGCGATTC CGTTGCAATG GCTGGCGGTA ATATTGTTCT GGATATTACC
      GTCCGCTAAG GCAACGTTAC CGACCGCCAT TATAACAAGA CCTATAATGG

5901  AGCAAGGCCG ATAGTTTGAG TTCTTCTACT CAGGCAAGTG ATGTTATTAC
      TCGTTCCGGC TATCAAACTC AAGAAGATGA GTCCGTTCAC TACAATAATG

5951  TAATCAAAGA AGTATTGCGA CAACGGTTAA TTTGCGTGAT GGACAGACTC
      ATTAGTTTCT TCATAACGCT GTTGCCAATT AAACGCACTA CCTGTCTGAG
```

Figure 16a-7

```
6001  TTTTACTCGG  TGGCCTCACT  GATTATAAAA  ACACTTCTCA  GGATTCTGGC
      AAAATGAGCC  ACCGGAGTGA  CTAATATTTT  TGTGAAGAGT  CCTAAGACCG

6051  GTACCGTTCC  TGTCTAAAAT  CCCTTTAATC  GGCCTCCTGT  TTAGCTCCCG
      CATGGCAAGG  ACAGATTTTA  GGGAAATTAG  CCGGAGGACA  AATCGAGGGC

6101  CTCTGATTCT  AACGAGGAAA  GCACGTTATA  CGTGCTCGTC  AAAGCAACCA
      GAGACTAAGA  TTGCTCCTTT  CGTGCAATAT  GCACGAGCAG  TTTCGTTGGT

6151  TAGTACGCGC  CCTGTAGCGG  CGCATTAAGC  GCGGCGGGTG  TGGTGGTTAC
      ATCATGCGCG  GGACATCGCC  GCGTAATTCG  CGCCGCCCAC  ACCACCAATG

6201  GCGCAGCGTG  ACCGCTACAC  TTGCCAGCGC  CCTAGCGCCC  GCTCCTTTCG
      CGCGTCGCAC  TGGCGATGTG  AACGGTCGCG  GGATCGCGGG  CGAGGAAAGC

6251  CTTTCTTCCC  TTCCTTTCTC  GCCACGTTCG  CCGGCTTTCC  CCGTCAAGCT
      GAAAGAAGGG  AAGGAAAGAG  CGGTGCAAGC  GGCCGAAAGG  GGCAGTTCGA

6301  CTAAATCGGG  GGCTCCCTTT  AGGGTTCCGA  TTTAGTGCTT  TACGGCACCT
      GATTTAGCCC  CCGAGGGAAA  TCCCAAGGCT  AAATCACGAA  ATGCCGTGGA

6351  CGACCCCAAA  AAACTTGATT  AGGGTGATGG  TTCACGTAGT  GGGCCATCGC
      GCTGGGGTTT  TTTGAACTAA  TCCCACTACC  AAGTGCATCA  CCCGGTAGCG

6401  CCTGATAGAC  GGTTTTTCGC  CCTTTGACGT  TGGAGTCCAC  GTTCTTTAAT
      GGACTATCTG  CCAAAAAGCG  GGAAACTGCA  ACCTCAGGTG  CAAGAAATTA

6451  AGTGGACTCT  TGTTCCAAAC  TGGAACAACA  CTCAACCCTA  TCTCGGTCTA
      TCACCTGAGA  ACAAGGTTTG  ACCTTGTTGT  GAGTTGGGAT  AGAGCCAGAT

6501  TTCTTTTGAT  TTATAAGGGA  TTTTGCCGAT  TTCGGCCTAT  TGGTTAAAAA
      AAGAAAACTA  AATATTCCCT  AAAACGGCTA  AAGCCGGATA  ACCAATTTTT

6551  ATGAGCTGAT  TTAACAAAAA  TTTAACGCGA  ATTTTAACAA  AATATTAACG
      TACTCGACTA  AATTGTTTTT  AAATTGCGCT  TAAAATTGTT  TTATAATTGC

6601  CTTACAATTT  AAATATTTGC  TTATACAATC  TTCCTGTTTT  TGGGGCTTTT
      GAATGTTAAA  TTTATAAACG  AATATGTTAG  AAGGACAAAA  ACCCCGAAAA

6651  CTGATTATCA  ACCGGGGTAC  ATATGATTGA  CATGCTAGTT  TTACGATTAC
      GACTAATAGT  TGGCCCCATG  TATACTAACT  GTACGATCAA  AATGCTAATG

6701  CGTTCATCGG      (SEQ ID 28)
      GCAAGTAGCC
```

Figure 16a-8

```
1907  ATG GTG GCG GGG GCC CAT TGG GGA GTC CTG GCG GGT CTC GCC
       M   V   A   G   A   H   W   G   V   L   A   G   L   A
      347
1949  TAC TAT TCC ATG GTG GGG AAC TGG GCT AAG GTT TTG ATT GTG
       Y   Y   S   M   V   G   N   W   A   K   V   L   I   I   V
              364                                  ┌─►E2
1991  ATG CTA CTC TTT GCC GGC GTC GAC GGG CAT ACC CGC GTG TCA
       M   L   L   F   A   G   V   D   G   H   T   R   V   S
                                          384
2033  GGA GGG GCA GCA GCC TCC GAT ACC AGG GGC CTT GTG TCC CTC
       G   G   A   A   A   S   D   T   R   G   L   V   S   L
2075  TTT AGC CCC GGG TCG GCT CAG AAA ATC CAG CTC GTA AAC ACC
       F   S   P   G   S   A   Q   K   I   Q   L   V   N   T
                                  409         412
2117  AAC GGC AGT TGG CAC ATC AAC AGG ACT GCC CTG AAC TGC AAC
       N   G   S   W   H   I   N   R   T   A   L   N   C   N
2159  GAC TCC CTC CAA ACA GGG TTC TTT GCC GCA CTA TTC TAC AAA
       D   S   L   Q   T   G   F   F   A   A   L   F   Y   K
2201  CAC AAA TTC AAC TCG TCT GGA TGC CCA GAG CGC TTG GCC AGC
       H   K   F   N   S   S   G   C   P   E   R   L   A   S
2243  TGT CGC TCC ATC GAC AAG TTC GCT CAG GGG TGG GGT CCC CTC
       C   R   S   I   D   K   F   A   Q   G   W   G   P   L
2285  ACT TAC ACT GAG CCT AAC AGC TCG GAC CAG AGG CCC TAC TGC
       T   Y   T   E   P   N   S   S   D   Q   R   P   Y   C
2327  TGG CAC TAC GCG CCT CGA CCG TGT GGT ATT GTA CCC GCG TCT
       W   H   Y   A   P   R   P   C   G   I   V   P   A   S
2369  CAG GTG TGC GGT CCA GTG TAT TGC TTC ACC CCG AGC CCT GTT
       Q   V   C   G   P   V   Y   C   F   T   P   S   P   V
2411  GTG GTG GGG ACG ACC GAT CGG TTT GGT GTC CCC ACG TAT AAC
       V   V   G   T   T   D   R   F   G   V   P   T   Y   N
2453  TGG GGG GCG AAC GAC TCG GAT GTG CTG ATT CTC AAC AAC ACG
       W   G   A   N   D   S   D   V   L   I   L   N   N   T
2495  CGG CCG CCG CGA GGC AAC TGG TTC GGC TGT ACA TGG ATG AAT
       R   P   P   R   G   N   W   F   G   C   T   W   M   N
```

Figure 16b

```
2537  GGC ACT GGG TTC ACC AAG ACG TGT GGG GGC CCC CCG TGC AAC
       G   T   G   F   T   K   T   C   G   G   P   P   C   N

2579  ATC GGG GGG GCC GGC AAC AAC ACC TTG ACC TGC CCC ACT GAC
       I   G   G   A   G   N   N   T   L   T   C   P   T   D

2621  TGT TTT CGG AAG CAC CCC GAG GCC ACC TAC GCC AGA TGC GGT
       C   F   R   K   H   P   E   A   T   Y   A   R   C   G

2663  TCT GGG CCC TGG CTG ACA CCT AGG TGT ATG GTT CAT TAC CCA
       S   G   P   W   L   T   P   R   C   M   V   H   Y   P

2705  TAT AGG CTC TGG CAC TAC CCC TGC ACT GTC AAC TTC ACC ATC
       Y   R   L   W   H   Y   P   C   T   V   N   F   T   I

2747  TTC AAG GTT AGG ATG TAC GTG GGG GGC GTG GAG CAC AGG TTC
       F   K   V   R   M   Y   V   G   G   V   E   H   R   F

2789  GAA GCC GCA TGC AAT TGG ACT CGA GGA GAG CGT TGT GAC TTG
       E   A   A   C   N   W   T   R   G   E   R   C   D   L

2831  GAG GAC AGG GAT AGA TCA GAG CTT AGC CCG CTG CTG CTG TCT
       E   D   R   D   R   S   E   L   S   P   L   L   L   S

2873  ACA ACA GAG TGG CAG ATA CTG CCC TGT TCC TTC ACC ACC CTG
       T   T   E   W   Q   I   L   P   C   S   F   T   T   L

2915  CCG GCC CTA TCC ACC GGC CTG ATC CAC CTC CAT CAG AAC ATC
       P   A   L   S   T   G   L   I   H   L   H   Q   N   I

2957  GTG GAC GTG CAA TAC CTG TAC GGT GTA GGG TCG GCG GTT GTC
       V   D   V   Q   Y   L   Y   G   V   G   S   A   V   V

2999  TCC CTT GTC ATC AAA TAA (SEQ ID 29)
       S   L   V   I$_{715}$K   -
```

Figure 16b-1

```
                    SEQUENCE LISTING

<160> NUMBER OF SEQ ID NOS: 30

<210> SEQ ID NO 1
<211> LENGTH: 300
<212> TYPE: PRT
<213> ORGANISM: Hepatitis C virus

<400> SEQUENCE: 1
```

-continued

```
Met Ala Thr Cys Ile Asn Gly Val Cys Trp Thr Val Tyr His Gly Arg
 1               5                  10                  15

Ala Ala Val Cys Thr Arg Gly Val Ala Lys Ala Val Asp Phe Val Pro
                20                  25                  30

Val Glu Ser Met Glu Thr Thr Met Arg Ser Pro Val Phe Thr Asp Asn
            35                  40                  45

Ser Ser Pro Pro Ala Val Pro Gln Thr Phe Gln Val Ala His Leu His
        50                  55                  60

Ala Pro Thr Gly Ser Gly Lys Ser Thr Lys Val Pro Ala Ala Tyr Ala
 65                 70                  75                  80

Ala Gln Gly Tyr Lys Val Leu Val Leu Asn Pro Ser Val Ala Ala Thr
                85                  90                  95

Leu Gly Phe Gly Ala Tyr Met Ser Lys Ala His Gly Val Asp Pro Asn
            100                 105                 110

Ile Arg Thr Gly Val Arg Thr Ile Thr Thr Gly Ala Pro Ile Thr Tyr
        115                 120                 125

Ser Thr Tyr Gly Lys Phe Leu Ala Asp Gly Gly Cys Ser Gly Gly Ala
        130                 135                 140

Tyr Asp Ile Ile Ile Cys Asp Glu Cys His Ser Ile Asp Ser Thr Ser
145                 150                 155                 160

Ile Leu Gly Ile Gly Thr Val Leu Asp Gln Ala Glu Thr Ala Gly Ala
                165                 170                 175

Arg Leu Val Val Leu Ala Thr Ala Thr Pro Pro Gly Ser Val Thr Val
            180                 185                 190

Pro His Pro Asn Ile Glu Glu Val Ala Leu Ser Ser Thr Gly Glu Ile
        195                 200                 205

Pro Phe Tyr Gly Lys Ala Ile Pro Ile Glu Val Ile Lys Gly Gly Arg
        210                 215                 220

His Leu Ile Phe Cys His Ser Lys Lys Cys Asp Glu Leu Ala Ala
225                 230                 235                 240

Lys Leu Ser Gly Phe Gly Ile Asn Ala Val Ala Tyr Tyr Arg Gly Leu
                245                 250                 255

Asp Val Ser Val Ile Pro Thr Ser Gly Asp Val Val Val Val Ala Thr
            260                 265                 270

Asp Ala Leu Met Thr Gly Phe Thr Gly Asp Phe Asp Ser Val Ile Asp
        275                 280                 285

Cys Asn Thr Cys Val Thr Gln Thr Val Asp Phe Ser
        290                 295                 300

<210> SEQ ID NO 2
<211> LENGTH: 294
<212> TYPE: PRT
<213> ORGANISM: Hepatitis C virus

<400> SEQUENCE: 2

Met Gly Val Ala Lys Ala Val Asp Phe Val Pro Val Glu Ser Met Glu
 1               5                  10                  15

Thr Thr Met Arg Ser Pro Val Phe Thr Asp Asn Ser Ser Pro Pro Ala
                20                  25                  30

Val Pro Gln Thr Phe Gln Val Ala His Leu His Ala Pro Thr Gly Ser
            35                  40                  45

Gly Lys Ser Thr Lys Val Pro Ala Ala Tyr Ala Ala Gln Gly Tyr Lys
        50                  55                  60

Val Leu Val Leu Asn Pro Ser Val Ala Ala Thr Leu Gly Phe Gly Ala
 65                 70                  75                  80
```

```
Tyr Met Ser Lys Ala His Gly Val Asp Pro Asn Ile Arg Thr Gly Val
             85                  90                  95
Arg Thr Ile Thr Thr Gly Ala Pro Ile Thr Tyr Ser Thr Tyr Gly Lys
            100                 105                 110
Phe Leu Ala Asp Gly Gly Cys Ser Gly Gly Ala Tyr Asp Ile Ile Ile
            115                 120                 125
Cys Asp Glu Cys His Ser Ile Asp Ser Thr Ser Ile Leu Gly Ile Gly
            130                 135                 140
Thr Val Leu Asp Gln Ala Glu Thr Ala Gly Ala Arg Leu Val Val Leu
145                 150                 155                 160
Ala Thr Ala Thr Pro Pro Gly Ser Val Thr Val Pro His Pro Asn Ile
                165                 170                 175
Glu Glu Val Ala Leu Ser Ser Thr Gly Glu Ile Pro Phe Tyr Gly Lys
            180                 185                 190
Ala Ile Pro Ile Glu Val Ile Lys Gly Gly Arg His Leu Ile Phe Cys
            195                 200                 205
His Ser Lys Lys Lys Cys Asp Glu Leu Ala Ala Lys Leu Ser Gly Phe
            210                 215                 220
Gly Ile Asn Ala Val Ala Tyr Tyr Arg Gly Leu Asp Val Ser Val Ile
225                 230                 235                 240
Pro Thr Ser Gly Asp Val Val Val Ala Thr Asp Ala Leu Met Thr
                245                 250                 255
Gly Phe Thr Gly Asp Phe Asp Ser Val Ile Asp Cys Asn Thr Cys Val
                260                 265                 270
Thr Gln Thr Val Asp Phe Ser Leu Ala Thr Cys Ile Asn Gly Val Cys
            275                 280                 285
Trp Thr Val Tyr His Gly
        290

<210> SEQ ID NO 3
<211> LENGTH: 903
<212> TYPE: DNA
<213> ORGANISM: Hepatitis C virus

<400> SEQUENCE: 3
atggcgacct gcatcaacgg tgtttgctgg accgtttacc acggtcgtgc ggctgtttgc      60
acccgtgggg ttgcgaaggc ggtggacttt gtacccgtag agtctatgga aaccaccatg     120
cggtccccgg tctttacgga taactcatct cctccggccg taccgcagac attccaagtg     180
gcccatctac acgcccccac tggtagtggc aagagcacta aggtgccggc tgcatatgca     240
gcccaagggt acaaggtact tgtcctgaac ccatccgttg ccgccacctt aggattcggg     300
gcgtatatgt ctaaagcaca tggtgtcgac cctaacatta gaactggggt aaggaccatc     360
accacgggcg cccccattac gtactccacc tacggcaagt tcttgccga cggtggttgc     420 tctgggggcg cttacgacat cataatatgt gatgagtgcc actcgattga ctcaacctcc     480
atcttgggca tcggcaccgt cctggatcag gcggagacgg ctggagcgcg gcttgtcgtg     540
ctcgccactg ctacacctcc ggggtcggtc accgtgccac atcccaacat cgaggaggtg     600
gctctgtcca gcactggaga gatccccttt tatggcaaag ccatccccat cgaggtcatc     660 aaaggggga ggcacctcat tttctgccat tccaagaaga aatgtgacga gctcgccgca     720
aagctatcgg gcttcggaat caacgctgta gcgtattacc gaggccttga tgtgtccgtc     780
ataccgacta gcggagacgt cgttgttgtg gcaacagacg ctctaatgac gggctttacc     840
```

-continued

```
ggcgactttg actcagtgat cgactgtaac acatgcgtca cccagacagt cgacttcagc    900
taa                                                                 903

<210> SEQ ID NO 4
<211> LENGTH: 885
<212> TYPE: DNA
<213> ORGANISM: Hepatitis C virus

<400> SEQUENCE: 4 atggggggttg cgaaggcggt ggactttgta cccgtagagt ctatggaaac caccatgcgg    60
tccccggtct ttacggataa ctcatctcct ccggccgtac cgcagacatt ccaagtggcc   120
catctacacg cccccactgg tagtggcaag agcactaagg tgccggctgc atatgcagcc   180
caagggtaca aggtacttgt cctgaaccca tccgttgccg ccaccttagg attcggggcg   240
tatatgtcta agcacatgg tgtcgaccct aacattagaa ctggggtaag gaccatcacc   300
acgggcgccc ccattacgta ctccacctac ggcaagtttc ttgccgacgg tggttgctct   360
gggggcgctt acgacatcat aaatatgtgat gagtgccact cgattgactc aacctccatc   420
ttgggcatcg gcaccgtcct ggatcaggcg gagacggctg gagcgcggct tgtcgtgctc   480
gccactgcta cacctccggg gtcggtcacc gtgccacatc ccaacatcga ggaggtggct   540
ctgtccagca ctggagagat ccccttttat ggcaaagcca tccccatcga ggtcatcaaa   600
ggggggaggc acctcatttt ctgccattcc aagaagaaat gtgacgagct cgccgcaaag   660
ctatcgggct tcggaatcaa cgctgtagcg tattaccgag gccttgatgt gtccgtcata   720
ccgactagcg gagacgtcgt tgttgtggca acagacgctc taatgacggg cttaccggc   780 gactttgact cagtgatcga ctgtaacaca tgcgtcaccc agacagtcga cttcagcctg   840
gcgacctgca tcaacggtgt ttgctggacc gtttaccacg gttaa                   885

<210> SEQ ID NO 5
<211> LENGTH: 88
<212> TYPE: DNA
<213> ORGANISM: Hepatitis C virus

<400> SEQUENCE: 5
gccatggcga cctgcatcaa cggtgtttgc tggaccgttt accacggtcg tgcggctgtt    60
tgcacccgtg gggttgcgaa ggcggtgg                                      88

<210> SEQ ID NO 6
<211> LENGTH: 21
<212> TYPE: DNA
<213> ORGANISM: Hepatitis C virus

<400> SEQUENCE: 6
ttttatcaga ccgcttctgc g                                             21

<210> SEQ ID NO 7
<211> LENGTH: 18
<212> TYPE: DNA
<213> ORGANISM: Hepatitis C virus

<400> SEQUENCE: 7
agcaaaccac caagtgga                                                 18

<210> SEQ ID NO 8
<211> LENGTH: 77
<212> TYPE: DNA
<213> ORGANISM: Hepatitis C virus
```

-continued

<400> SEQUENCE: 8
ctctagacta ttaaccgtgg taaacggtcc agcaaacacc gttgatgcag gtcgccaggc    60
tgaagtcgac tgtctgg    77

<210> SEQ ID NO 9
<211> LENGTH: 38
<212> TYPE: DNA
<213> ORGANISM: Hepatitis C virus

<400> SEQUENCE: 9
ctttgccggc gtcgacgggc agaaaatcca gctcgtaa    38

<210> SEQ ID NO 10
<211> LENGTH: 38
<212> TYPE: DNA
<213> ORGANISM: Hepatitis C virus

<400> SEQUENCE: 10
ttacgagctg gattttctgc ccgtcgacgc cggcaaag    38

<210> SEQ ID NO 11
<211> LENGTH: 38
<212> TYPE: DNA
<213> ORGANISM: Hepatitis C virus

<400> SEQUENCE: 11
ctttgccggc gtcgacgggc agctcgtaaa caccaacg    38

<210> SEQ ID NO 12
<211> LENGTH: 38
<212> TYPE: DNA
<213> ORGANISM: Hepatitis C virus

<400> SEQUENCE: 12
cgttggtgtt tacgagctgc ccgtcgacgc cggcaaag    38

<210> SEQ ID NO 13
<211> LENGTH: 307
<212> TYPE: PRT
<213> ORGANISM: Hepatitis C virus

<400> SEQUENCE: 13

Gln Lys Ile Gln Leu Val Asn Thr Asn Gly Ser Trp His Ile Asn Arg
  1               5                  10                  15

Thr Ala Leu Asn Cys Asn Asp Ser Leu Gln Thr Gly Phe Phe Ala Ala
             20                  25                  30

Leu Phe Tyr Lys His Lys Phe Asn Ser Ser Gly Cys Pro Glu Arg Leu
         35                  40                  45

Ala Ser Cys Arg Ser Ile Asp Lys Phe Ala Gln Gly Trp Gly Pro Leu
     50                  55                  60

Thr Tyr Thr Glu Pro Asn Ser Ser Asp Gln Arg Pro Tyr Cys Trp His
 65                  70                  75                  80

Tyr Ala Pro Arg Pro Cys Gly Ile Val Pro Ala Ser Gln Val Cys Gly
                 85                  90                  95

Pro Val Tyr Cys Phe Thr Pro Ser Pro Val Val Gly Thr Thr Asp
            100                 105                 110

Arg Phe Gly Val Pro Thr Tyr Asn Trp Gly Ala Asn Asp Ser Asp Val
        115                 120                 125

```
Leu Ile Leu Asn Asn Thr Arg Pro Pro Arg Gly Asn Trp Phe Gly Cys
    130                 135                 140

Thr Trp Met Asn Gly Thr Gly Phe Thr Lys Thr Cys Gly Gly Pro Pro
145                 150                 155                 160

Cys Asn Ile Gly Gly Ala Gly Asn Asn Thr Leu Thr Cys Pro Thr Asp
            165                 170                 175

Cys Phe Arg Lys His Pro Glu Ala Thr Tyr Ala Arg Cys Gly Ser Gly
            180                 185                 190

Pro Trp Leu Thr Pro Arg Cys Met Val His Tyr Pro Tyr Arg Leu Trp
            195                 200                 205

His Tyr Pro Cys Thr Val Asn Phe Thr Ile Phe Lys Val Arg Met Tyr
    210                 215                 220

Val Gly Gly Val Glu His Arg Phe Glu Ala Ala Cys Asn Trp Thr Arg
225                 230                 235                 240

Gly Glu Arg Cys Asp Leu Glu Asp Arg Asp Arg Ser Glu Leu Ser Pro
            245                 250                 255

Leu Leu Leu Ser Thr Thr Glu Trp Gln Ile Leu Pro Cys Ser Phe Thr
            260                 265                 270

Thr Leu Pro Ala Leu Ser Thr Gly Leu Ile His Leu His Gln Asn Ile
            275                 280                 285

Val Asp Val Gln Tyr Leu Tyr Gly Val Gly Ser Ala Val Val Ser Leu
    290                 295                 300

Val Ile Lys
305

<210> SEQ ID NO 14
<211> LENGTH: 304
<212> TYPE: PRT
<213> ORGANISM: Hepatitis C virus

<400> SEQUENCE: 14

Gln Leu Val Asn Thr Asn Gly Ser Trp His Ile Asn Arg Thr Ala Leu
  1                 5                  10                  15

Asn Cys Asn Asp Ser Leu Gln Thr Gly Phe Phe Ala Ala Leu Phe Tyr
            20                  25                  30

Lys His Lys Phe Asn Ser Ser Gly Cys Pro Glu Arg Leu Ala Ser Cys
        35                  40                  45

Arg Ser Ile Asp Lys Phe Ala Gln Gly Trp Gly Pro Leu Thr Tyr Thr
    50                  55                  60

Glu Pro Asn Ser Ser Asp Gln Arg Pro Tyr Cys Trp His Tyr Ala Pro
65                  70                  75                  80

Arg Pro Cys Gly Ile Val Pro Ala Ser Gln Val Cys Gly Pro Val Tyr
                85                  90                  95

Cys Phe Thr Pro Ser Pro Val Val Val Gly Thr Thr Asp Arg Phe Gly
            100                 105                 110

Val Pro Thr Tyr Asn Trp Gly Ala Asn Asp Ser Asp Val Leu Ile Leu
        115                 120                 125

Asn Asn Thr Arg Pro Pro Arg Gly Asn Trp Phe Gly Cys Thr Trp Met
    130                 135                 140

Asn Gly Thr Gly Phe Thr Lys Thr Cys Gly Gly Pro Pro Cys Asn Ile
145                 150                 155                 160

Gly Gly Ala Gly Asn Asn Thr Leu Thr Cys Pro Thr Asp Cys Phe Arg
                165                 170                 175

Lys His Pro Glu Ala Thr Tyr Ala Arg Cys Gly Ser Gly Pro Trp Leu
            180                 185                 190
```

```
Thr Pro Arg Cys Met Val His Tyr Pro Tyr Arg Leu Trp His Tyr Pro
        195                 200                 205
Cys Thr Val Asn Phe Thr Ile Phe Lys Val Arg Met Tyr Val Gly Gly
        210                 215                 220
Val Glu His Arg Phe Glu Ala Ala Cys Asn Trp Thr Arg Gly Glu Arg
225                 230                 235                 240
Cys Asp Leu Glu Asp Arg Asp Arg Ser Glu Leu Ser Pro Leu Leu Leu
                245                 250                 255
Ser Thr Thr Glu Trp Gln Ile Leu Pro Cys Ser Phe Thr Thr Leu Pro
            260                 265                 270
Ala Leu Ser Thr Gly Leu Ile His Leu His Gln Asn Ile Val Asp Val
            275                 280                 285
Gln Tyr Leu Tyr Gly Val Gly Ser Ala Val Val Ser Leu Val Ile Lys
            290                 295                 300

<210> SEQ ID NO 15
<211> LENGTH: 135
<212> TYPE: PRT
<213> ORGANISM: Hepatitis C virus

<400> SEQUENCE: 15

Tyr Gln Val Arg Asn Ser Thr Gly Leu Tyr His Val Thr Asn Asp Cys
1               5                   10                  15
Pro Asn Ser Ser Ile Val Tyr Glu Ala Ala Asp Ala Ile Leu His Thr
            20                  25                  30
Pro Gly Cys Val Pro Cys Val Arg Glu Gly Asn Ala Ser Arg Cys Trp
        35                  40                  45
Val Ala Met Thr Pro Thr Val Ala Thr Arg Asp Gly Lys Leu Pro Thr
    50                  55                  60
Thr Gln Leu Arg Arg His Ile Asp Leu Leu Val Gly Ser Ala Thr Leu
65                  70                  75                  80
Cys Ser Ala Leu Tyr Val Gly Asp Leu Cys Gly Ser Val Phe Leu Val
                85                  90                  95
Gly Gln Leu Phe Thr Phe Ser Pro Arg Arg His Trp Thr Thr Gln Glu
            100                 105                 110
Cys Asn Cys Ser Met Tyr Pro Gly His Ile Thr Gly His Arg Met Ala
        115                 120                 125
Trp Asp Met Met Met Asn Trp
    130                 135

<210> SEQ ID NO 16
<211> LENGTH: 135
<212> TYPE: PRT
<213> ORGANISM: Hepatitis C virus

<400> SEQUENCE: 16

Tyr Glu Val Arg Asn Val Ser Gly Met Tyr His Val Thr Asn Asp Cys
1               5                   10                  15
Ser Asn Ser Ser Ile Val Tyr Glu Ala Ala Asp Met Ile Met His Thr
            20                  25                  30
Pro Gly Cys Val Pro Cys Val Arg Glu Asn Asn Ser Ser Arg Cys Trp
        35                  40                  45
Val Ala Leu Thr Pro Thr Leu Ala Ala Arg Asn Ala Ser Val Pro Thr
    50                  55                  60
Thr Thr Ile Arg Arg His Val Asp Leu Leu Val Gly Ala Ala Ala Phe
65                  70                  75                  80
```

```
Cys Ser Ala Met Tyr Val Gly Asp Leu Cys Gly Ser Val Phe Leu Val
                85                  90                  95

Ser Gln Leu Phe Thr Ile Ser Pro Arg Arg His Glu Thr Val Gln Asp
            100                 105                 110

Cys Asn Cys Ser Ile Tyr Pro Gly His Ile Thr Gly His Arg Met Ala
            115                 120                 125

Trp Asp Met Met Met Asn Trp
        130                 135

<210> SEQ ID NO 17
<211> LENGTH: 135
<212> TYPE: PRT
<213> ORGANISM: Hepatitis C virus

<400> SEQUENCE: 17

Tyr Glu Val Arg Asn Val Ser Gly Val Tyr His Val Thr Asn Asp Cys
  1               5                  10                  15

Ser Asn Ala Ser Ile Val Tyr Glu Ala Ala Asp Met Ile Met His Thr
            20                  25                  30

Pro Gly Cys Val Pro Cys Val Arg Glu Gly Asn Ser Ser Arg Cys Trp
            35                  40                  45

Val Ala Leu Thr Pro Thr Leu Ala Ala Arg Asn Val Ser Val Pro Thr
        50                  55                  60

Thr Thr Ile Arg Arg His Val Asp Leu Ile Val Gly Ala Ala Ala Phe
 65                  70                  75                  80

Cys Ser Ala Met Tyr Val Gly Asp Leu Cys Gly Ser Val Phe Leu Val
                85                  90                  95

Ser Gln Leu Phe Thr Phe Ser Pro Arg Arg His Glu Thr Val Gln Asp
            100                 105                 110

Cys Asn Cys Ser Ile Tyr Pro Gly His Val Ser Gly His Arg Met Ala
            115                 120                 125

Trp Asp Met Met Met Asn Trp
        130                 135

<210> SEQ ID NO 18
<211> LENGTH: 35
<212> TYPE: PRT
<213> ORGANISM: Hepatitis C virus

<400> SEQUENCE: 18

Tyr Glu Val Arg Asn Val Ser Gly Ile Tyr His Val Thr Asn Asp Cys
  1               5                  10                  15

Ser Asn Ser Ser Ile Val Tyr Glu Ala Ala Asp Met Ile Met His Thr
            20                  25                  30

Pro Gly Cys
        35

<210> SEQ ID NO 19
<211> LENGTH: 29
<212> TYPE: PRT
<213> ORGANISM: Hepatitis C virus

<400> SEQUENCE: 19

Ile Val Tyr Glu Ala Ala Asp Met Ile Met His Thr Pro Gly Cys Val
  1               5                  10                  15

Pro Cys Val Arg Glu Asn Asn Ser Ser Arg Cys Trp Val
            20                  25
```

```
<210> SEQ ID NO 20
<211> LENGTH: 34
<212> TYPE: PRT
<213> ORGANISM: Hepatitis C virus

<400> SEQUENCE: 20

Val Arg Glu Asn Asn Ser Ser Arg Cys Trp Val Ala Leu Thr Pro Thr
 1               5                  10                  15

Leu Ala Ala Arg Asn Ala Ser Val Pro Thr Thr Thr Ile Arg Arg His
            20                  25                  30

Val Asp

<210> SEQ ID NO 21
<211> LENGTH: 30
<212> TYPE: PRT
<213> ORGANISM: Hepatitis C virus

<400> SEQUENCE: 21

His Val Asp Leu Leu Val Gly Ala Ala Ala Phe Cys Ser Ala Met Tyr
 1               5                  10                  15

Val Gly Asp Leu Cys Gly Ser Val Phe Leu Val Ser Gln Leu
            20                  25                  30

<210> SEQ ID NO 22
<211> LENGTH: 40
<212> TYPE: PRT
<213> ORGANISM: Hepatitis C virus

<400> SEQUENCE: 22

Ser Gln Leu Phe Thr Ile Ser Pro Arg Arg His Glu Thr Val Gln Asp
 1               5                  10                  15

Cys Asn Cys Ser Ile Tyr Pro Gly His Ile Thr Gly His Arg Met Ala
            20                  25                  30

Trp Asp Met Met Met Asn Trp Ser
            35                  40

<210> SEQ ID NO 23
<211> LENGTH: 34
<212> TYPE: PRT
<213> ORGANISM: Hepatitis C virus

<400> SEQUENCE: 23

Ser Ile Tyr Pro Gly His Ile Thr Gly His Arg Met Ala Trp Asp Met
 1               5                  10                  15

Met Met Asn Trp Ser Pro Thr Thr Ala Leu Val Val Ser Gln Leu Leu
            20                  25                  30

Arg Ile

<210> SEQ ID NO 24
<211> LENGTH: 26
<212> TYPE: PRT
<213> ORGANISM: Hepatitis C virus

<400> SEQUENCE: 24

Met Ala Thr Cys Ile Asn Gly Val Cys Trp Thr Val Tyr His Gly Arg
 1               5                  10                  15

Ala Ala Val Cys Thr Arg Gly Val Ala Lys
            20                  25

<210> SEQ ID NO 25
```

```
<211> LENGTH: 26
<212> TYPE: PRT
<213> ORGANISM: Hepatitis C virus

<400> SEQUENCE: 25

Gly Gly Pro Leu Leu Cys Pro Ala Gly His Ala Val Gly Ile Phe Arg
 1               5                  10                  15

Ala Ala Val Cys Thr Arg Gly Val Ala Lys
            20                  25

<210> SEQ ID NO 26
<211> LENGTH: 19
<212> TYPE: PRT
<213> ORGANISM: Hepatitis C virus

<400> SEQUENCE: 26

Val Asp Phe Ser Leu Ala Thr Cys Ile Asn Gly Val Cys Trp Thr Val
 1               5                  10                  15

Tyr His Gly

<210> SEQ ID NO 27
<211> LENGTH: 19
<212> TYPE: PRT
<213> ORGANISM: Hepatitis C virus

<400> SEQUENCE: 27

Val Asp Phe Ser Leu Asp Pro Thr Phe Thr Ile Glu Thr Ile Thr Leu
 1               5                  10                  15

Pro Gln Asp

<210> SEQ ID NO 28
<211> LENGTH: 6710
<212> TYPE: DNA
<213> ORGANISM: Hepatitis C virus

<400> SEQUENCE: 28
agcttttgcg atcaataaat ggatcacaac cagtatctct taacgatgtt cttcgcagat      60
gatgattcat tttttaagta tttggctagt caagatgatg aatcttcatt atctgatata     120
ttgcaaatca ctcaatatct agactttctg ttattattat tgatccaatc aaaaaataaa     180
ttagaagccg tgggtcattg ttatgaatct ctttcagagg aatacagaca attgacaaaa     240
ttcacagact tcaagatttt aaaaaactg tttaacaagg tccctattgt tacagatgga     300
agggtcaaac ttaataaagg atatttgttc gactttgtga ttagtttgat gcgattcaaa     360
aaagaatcct ctctagctac caccgcaata gatcctgtta gatacataga tcctcgtcgc     420
aatatcgcat tttctaacgt gatggatata ttaaagtcga ataaagtgaa caataattaa     480
ttctttattg tcatcatgaa cggcggacat attcagttga taatcggccc catgttttca     540
ggtaaaagta cagaattaat tagacgagtt agacgttatc aaatagctca atataaatgc     600
gtgactataa atattctaa cgataataga tacggaacgg gactatggac gcatgataag     660
aataattttg aagcattgga agcaactaaa ctatgtgatg tcttggaatc aattacagat     720
ttctccgtga taggatactc ataaatccag ttgccgccac ggtagccaat caccgtatcg     780
tataaatcat cgtcggtacg ttcggcatcg ctcatcacaa tacgtgcctg gacgtcgagg     840
atttcgcgtg ggtcaatgcc gcgccagatc cacatcagac ggttaatcat gcgataccag     900
tgagggatgg ttttaccatc aagggccgac tgcacaggcg gttgtgcgcc gtgattaaag     960
cggcggacta gcgtcgaggt ttcaggatgt ttaaagcggg gtttgaacag ggtttcgctc    1020
```

-continued

```
aggtttgcct gtgtcatgga tgcagcctcc agaatactta ctggaaacta ttgtaacccg    1080
cctgaagtta aaaagaacaa cgcccggcag tgccaggcgt tgaaaagatt agcgaccgga    1140
gattggcggg acgaatacga cgcccatatc ccacggctgt tcaatccagg tatcttgcgg    1200
gatatcaaca acatagtcat caaccagcgg acgaccagcc ggttttgcga agatggtgac    1260
aaagtgcgct tttggataca tttcacgaat cgcaaccgca gtaccaccgg tatccaccag    1320
gtcatcaata acgatgaagc cttcgccatc gccttctgcg cgtttcagca ctttaagctc    1380
gcgctggttg tcgtgatcgt agctggaaat acaaacggta tcgacatgac gaatacccag    1440
ttcacgcgcc agtaacgcac ccggtaccag accgccacgg cttacggcaa taatgccttt    1500
ccattgttca gaaggcatca gtcggcttgc gagtttacgt gcatggatct gcaacatgtc    1560
ccaggtgacg atgtattttt cgctcatgtg aagtgtccca gcctgtttat ctacggctta    1620
aaaagtgttc gaggggaaaa taggttgcgc gagattatag ggccttactt tgtaatataa    1680
tgatatatat tttcactttta tctcatttga gaataaaaat gtttttgttt aaccactgca    1740
tgatgtcaat tccgatccta gaagcgatgc tacgctagtc acaatcacca ctttcatatt    1800
tagaatatat gtatgtaaaa atatagtaga atttcatttt gttttttttct atcgattaaa    1860 tagaattcga gctcggtacc cggggatccc acaagctgtc gtggacatgg tggcgggggc    1920
ccattgggga gtcctggcgg gtctcgccta ctattccatg gtggggaact gggctaaggt    1980
tttgattgtg atgctactct ttgccggcgt cgacgggcat acccgcgtgt caggagggc    2040 agcagcctcc gataccaggg gccttgtgtc cctctttagc cccgggtcgg ctcagaaaat    2100
ccagctcgta acaccaacg gcagttggca catcaacagg actgccctga actgcaacga    2160
ctccctccaa acagggttct tgccgcact attctacaaa cacaaattca actcgtctgg    2220
atgcccagag cgcttggcca gctgtcgctc atcgacaag ttcgctcagg ggtgggtcc    2280 cctcacttac actgagccta acagctcgga ccagaggccc tactgctggc actacgcgcc    2340
tcgaccgtgt ggtattgtac ccgcgtctca ggtgtgcggt ccagtgtatt gcttcacccc    2400
gagccctgtt gtggtgggga cgaccgatcg gtttggtgtc cccacgtata actgggggc    2460 gaacgactcg gatgtgctga ttctcaacaa cacgcggccg ccgcgaggca actggttcgg    2520
ctgtacatgg atgaatggca ctgggttcac caagacgtgt gggggccccc cgtgcaacat    2580 cggggggggcc ggcaacaaca ccttgacctg ccccactgac tgttttcgga agcaccccga    2640
ggccacctac gccagatgcg gttctgggcc ctggctgaca cctaggtgta tggttcatta    2700
cccatatagg ctctggcact acccctgcac tgtcaacttc accatcttca aggttaggat    2760
gtacgtgggg ggcgtggagc acaggttcga agccgcatgc aattggactc gaggagagcg    2820
ttgtgacttg gaggacaggg atagatcaga gcttagcccg ctgctgctgt ctacaacaga    2880
gtggcagata ctgccctgtt ccttcaccac cctgccggcc ctatccaccg gcctgatcca    2940
cctccatcag aacatcgtgg acgtgcaata cctgtacggt gtagggtcgg cggttgtctc    3000
ccttgtcatc aaataagctt aattaattag cttgggatcg gctgtgagcg tatggcaaac    3060
gaaggaaaaa tagttatagt agccgcactc gatgggacat ttcaacgtaa accgtttaat    3120
aatattttga atcttattcc attatctgaa atggtggtaa aactaactgc tgtgtgtatg    3180
aaatgcttta aggaggcttc cttttctaaa cgattgggtg aggaaaccga gatagaaata    3240
ataggaggta atgatatgta tcaatcggtg tgtagaaagt gttacatcga ctcataatat    3300
tatatttttt atctaaaaaa ctaaaaataa acattgatta aatttaaata taatacttaa    3360
```

```
aaatggatgt tgtgtcgtta gataaaccgt ttatgtattt tgaggaaatt gataatgagt    3420
tagattacga accagaaagt gcaaatgagg tcgcaaaaaa actgccgtat caaggacagt    3480
taaaactatt actaggagaa ttattttttc ttagtaagtt acagcgacac ggtatattag    3540
atggtgccac cgtagtgtat ataggatctg ctcccggatc gatcctgcat taatgaatcg    3600
gccaacgcgc gggagagggc ggtttgcgta ttgggcttcc tcgctgcgct cggtcgttcg    3660
gctgcggcga gcggtatcag ctcactcaaa ggcggtaata cggttatcca cagaatcagg    3720
ggataacgca ggaaagaaca tgtgagcaaa aggccagcaa aaggccagga accgtaaaaa    3780
ggccgcgttg ctggcgtttt tccataggct ccgcccccct gacgagcatc acaaaaatcg    3840
acgctcaagt cagaggtggc gaaacccgac aggactataa agataccagg cgtttccccc    3900
tggaagctcc ctcgtgcgct ctcctgttcc gaccctgccg cttaccggat acctgtccgc    3960
ctttctccct tcgggaagcg tggcgctttc tcatagctca cgctgtaggt atctcagttc    4020
ggtgtaggtc gttcgctcca agctgggctg tgtgcacgaa ccccccgttc agcccgaccg    4080
ctgcgcctta tccggtaact atcgtcttga gtccaacccg gtaagacacg acttatcgcc    4140
actggcagca gccactggta acaggattag cagagcgagg tatgtaggcg gtgctacaga    4200
gttcttgaag tggtggccta actacggcta cactagaaga acagtatttg gtatctgcgc    4260
tctgctgaag ccagttacct tcggaaaaag agttggtagc tcttgatccg gcaaacaaac    4320
caccgctggt agcggtggtt tttttgtttg caagcagcag attacgcgca gaaaaaaagg    4380
atctcaagaa gatcctttga tcttttctac ggggtctgac gctcagtgga acgaaaactc    4440
acgttaaggg attttggtca tgagattatc aaaaaggatc ttcacctaga tccttttaaa    4500
ttaaaaatga agttttaaat caatctaaag tatatatgag taaacttggt ctgacagtta    4560
ccaatgctta atcagtgagg cacctatctc agcgatctgt ctatttcgtt catccatagt    4620
tgcctgactc ccgtcgtgt agataactac gatacgggag ggcttaccat ctggccccag    4680
tgctgcaatg ataccgcgag acccacgctc accggctcca gatttatcag caataaacca    4740
gccagccgga agggccgagc gcagaagtgg tcctgcaact ttatccgcct ccatccagtc    4800
tattaattgt tgccgggaag ctagagtaag tagttcgcca gttaatagtt tgcgcaacgt    4860
tgttgccatt gctacaggca tcgtggtgtc acgctcgtcg tttggtatgg cttcattcag    4920
ctccggttcc caacgatcaa ggcgagttac atgatccccc atgttgtgca aaaaagcggt    4980
tagctccttc ggtcctccga tcgttgtcag aagtaagttg gccgcagtgt tatcactcat    5040
ggttatggca gcactgcata attctcttac tgtcatgcca tccgtaagat gcttttctgt    5100
gactggtgag tactcaacca agtcattctg agaatagtgt atgcggcgac cgagttgctc    5160
ttgcccggcg tcaatacggg ataataccgc gccacatagc agaactttaa aagtgctcat    5220
cattggaaaa cgttcttcgg ggcgaaaact ctcaaggatc ttaccgctgt tgagatccag    5280
ttcgatgtaa cccactcgtg cacccaactg atcttcagca tcttttactt tcaccagcgt    5340
ttctgggtga gcaaaaacag gaaggcaaaa tgccgcaaaa aagggaataa gggcgacacg    5400
gaaatgttga atactcatac tcctcctttt tcaatattat tgaagcattt atcagggtta    5460
ttgtctcatg agcggataca tatttgaatg tatttagaaa aataaacaaa tagggggttcc    5520
gcgcacattt ccccgaaaag tgccacctga cgtctaagaa accattatta tcatgacatt    5580
aacctataaa aataggcgta tcacgaggcc ctttcgtctc gcgcgtttcg gtgatgacgg    5640
tgaaaacctc tgacacatgc agctcccgga gacggtcaca gcttgtctgt aagcggatgc    5700
cgggagcaga caagcccgtc agggcgcgtc agcgggtgtt ggcgggtgtc ggggctggct    5760
```

-continued

```
taactatgcg gcatcagagc agattgtact gagagtgcac catatgcggt gtgaaatacc    5820
gcacagatgc gtaaggagaa ataccgcat caggcgattc cgttgcaatg gctggcggta     5880
atattgttct ggatattacc agcaaggccg atagtttgag ttcttctact caggcaagtg    5940
atgttattac taatcaaaga agtattgcga caacggttaa tttgcgtgat ggacagactc    6000
ttttactcgg tggcctcact gattataaaa acacttctca ggattctggc gtaccgttcc    6060
tgtctaaaat ccctttaatc ggcctcctgt ttagctcccg ctctgattct aacgaggaaa    6120
gcacgttata cgtgctcgtc aaagcaacca tagtacgcgc cctgtagcgg cgcattaagc    6180
gcggcgggtg tggtggttac gcgcagcgtg accgctacac ttgccagcgc cctagcgccc    6240
gctcctttcg ctttcttccc ttcctttctc gccacgttcg ccggctttcc ccgtcaagct    6300
ctaaatcggg gctcccttt agggttccga tttagtgctt acggcacct cgaccccaaa      6360 aaacttgatt agggtgatgg ttcacgtagt gggccatcgc cctgatagac ggttttcgc     6420 cctttgacgt tggagtccac gttctttaat agtggactct tgttccaaac tggaacaaca    6480
ctcaacccta tctcggtcta ttcttttgat ttataaggga ttttgccgat tcggcctat    6540 tggttaaaaa atgagctgat ttaacaaaaa tttaacgcga atttaacaa aatattaacg     6600 cttacaattt aaatatttgc ttatacaatc ttcctgtttt tggggctttt ctgattatca    6660
accggggtac atatgattga catgctagtt ttacgattac cgttcatcgg                6710
```

<210> SEQ ID NO 29
<211> LENGTH: 1110
<212> TYPE: DNA
<213> ORGANISM: Hepatitis C virus
<220> FEATURE:
<221> NAME/KEY: CDS
<222> LOCATION: (1)..(1110)

<400> SEQUENCE: 29

```
atg gtg gcg ggg gcc cat tgg gga gtc ctg gcg ggt ctc gcc tac tat      48
Met Val Ala Gly Ala His Trp Gly Val Leu Ala Gly Leu Ala Tyr Tyr
 1               5                  10                  15 tcc atg gtg ggg aac tgg gct aag gtt ttg att gtg atg cta ctc ttt      96
Ser Met Val Gly Asn Trp Ala Lys Val Leu Ile Val Met Leu Leu Phe
             20                  25                  30 gcc ggc gtc gac ggg cat acc cgc gtg tca gga ggg gca gca gcc tcc     144
Ala Gly Val Asp Gly His Thr Arg Val Ser Gly Gly Ala Ala Ala Ser
         35                  40                  45 gat acc agg ggc ctt gtg tcc ctc ttt agc ccc ggg tcg gct cag aaa     192
Asp Thr Arg Gly Leu Val Ser Leu Phe Ser Pro Gly Ser Ala Gln Lys
     50                  55                  60 atc cag ctc gta aac acc aac ggc agt tgg cac atc aac agg act gcc     240
Ile Gln Leu Val Asn Thr Asn Gly Ser Trp His Ile Asn Arg Thr Ala
 65                  70                  75                  80 ctg aac tgc aac gac tcc ctc caa aca ggg ttc ttt gcc gca cta ttc     288
Leu Asn Cys Asn Asp Ser Leu Gln Thr Gly Phe Phe Ala Ala Leu Phe
                 85                  90                  95 tac aaa cac aaa ttc aac tcg tct gga tgc cca gag cgc ttg gcc agc     336
Tyr Lys His Lys Phe Asn Ser Ser Gly Cys Pro Glu Arg Leu Ala Ser
            100                 105                 110 tgt cgc tcc atc gac aag ttc gct cag ggg tgg ggt ccc ctc act tac     384
Cys Arg Ser Ile Asp Lys Phe Ala Gln Gly Trp Gly Pro Leu Thr Tyr
        115                 120                 125 act gag cct aac agc tcg gac cag agg ccc tac tgc tgg cac tac gcg     432
Thr Glu Pro Asn Ser Ser Asp Gln Arg Pro Tyr Cys Trp His Tyr Ala
    130                 135                 140
```

| | | | | | | | | | | | | | | | |
|---|---|---|---|---|---|---|---|---|---|---|---|---|---|---|---|
| cct | cga | ccg | tgt | ggt | att | gta | ccc | gcg | tct | cag | gtg | tgc | ggt | cca | gtg | 480 |
| Pro | Arg | Pro | Cys | Gly | Ile | Val | Pro | Ala | Ser | Gln | Val | Cys | Gly | Pro | Val | |
| 145 | | | | 150 | | | | | 155 | | | | | 160 | | |

```
cct cga ccg tgt ggt att gta ccc gcg tct cag gtg tgc ggt cca gtg      480
Pro Arg Pro Cys Gly Ile Val Pro Ala Ser Gln Val Cys Gly Pro Val
145                 150                 155                 160 tat tgc ttc acc ccg agc cct gtt gtg gtg ggg acg acc gat cgg ttt      528
Tyr Cys Phe Thr Pro Ser Pro Val Val Val Gly Thr Thr Asp Arg Phe
                165                 170                 175 ggt gtc ccc acg tat aac tgg ggg gcg aac gac tcg gat gtg ctg att      576
Gly Val Pro Thr Tyr Asn Trp Gly Ala Asn Asp Ser Asp Val Leu Ile
            180                 185                 190 ctc aac aac acg cgg ccg ccg cga ggc aac tgg ttc ggc tgt aca tgg      624
Leu Asn Asn Thr Arg Pro Pro Arg Gly Asn Trp Phe Gly Cys Thr Trp
        195                 200                 205 atg aat ggc act ggg ttc acc aag acg tgt ggg ggc ccc ccg tgc aac      672
Met Asn Gly Thr Gly Phe Thr Lys Thr Cys Gly Gly Pro Pro Cys Asn
    210                 215                 220 atc ggg ggg gcc ggc aac aac acc ttg acc tgc ccc act gac tgt ttt      720
Ile Gly Gly Ala Gly Asn Asn Thr Leu Thr Cys Pro Thr Asp Cys Phe
225                 230                 235                 240 cgg aag cac ccc gag gcc acc tac gcc aga tgc ggt tct ggg ccc tgg      768
Arg Lys His Pro Glu Ala Thr Tyr Ala Arg Cys Gly Ser Gly Pro Trp
                245                 250                 255 ctg aca cct agg tgt atg gtt cat tac cca tat agg ctc tgg cac tac      816
Leu Thr Pro Arg Cys Met Val His Tyr Pro Tyr Arg Leu Trp His Tyr
            260                 265                 270 ccc tgc act gtc aac ttc acc atc ttc aag gtt agg atg tac gtg ggg      864
Pro Cys Thr Val Asn Phe Thr Ile Phe Lys Val Arg Met Tyr Val Gly
        275                 280                 285 ggc gtg gag cac agg ttc gaa gcc gca tgc aat tgg act cga gga gag      912
Gly Val Glu His Arg Phe Glu Ala Ala Cys Asn Trp Thr Arg Gly Glu
    290                 295                 300 cgt tgt gac ttg gag gac agg gat aga tca gag ctt agc ccg ctg ctg      960
Arg Cys Asp Leu Glu Asp Arg Asp Arg Ser Glu Leu Ser Pro Leu Leu
305                 310                 315                 320 ctg tct aca aca gag tgg cag ata ctc ccc tgt tcc ttc acc acc ctg     1008
Leu Ser Thr Thr Glu Trp Gln Ile Leu Pro Cys Ser Phe Thr Thr Leu
                325                 330                 335 ccg gcc cta tcc acc ggc ctg atc cac ctc cat cag aac atc gtg gac     1056
Pro Ala Leu Ser Thr Gly Leu Ile His Leu His Gln Asn Ile Val Asp
            340                 345                 350 gtg caa tac ctg tac ggt gta ggg tcg gcg gtt gtc tcc ctt gtc atc     1104
Val Gln Tyr Leu Tyr Gly Val Gly Ser Ala Val Val Ser Leu Val Ile
        355                 360                 365 aaa taa                                                              1110
Lys
    370
```

<210> SEQ ID NO 30
<211> LENGTH: 369
<212> TYPE: PRT
<213> ORGANISM: Hepatitis C virus

<400> SEQUENCE: 30

```
Met Val Ala Gly Ala His Trp Gly Val Leu Ala Gly Leu Ala Tyr Tyr
  1               5                  10                  15

Ser Met Val Gly Asn Trp Ala Lys Val Leu Ile Val Met Leu Leu Phe
             20                  25                  30

Ala Gly Val Asp Gly His Thr Arg Val Ser Gly Ala Ala Ala Ser
         35                  40                  45

Asp Thr Arg Gly Leu Val Ser Leu Phe Ser Pro Gly Ser Ala Gln Lys
```

-continued

```
            50                  55                  60
Ile Gln Leu Val Asn Thr Asn Gly Ser Trp His Ile Asn Arg Thr Ala
 65                  70                  75                  80

Leu Asn Cys Asn Asp Ser Leu Gln Thr Gly Phe Phe Ala Ala Leu Phe
             85                  90                  95

Tyr Lys His Lys Phe Asn Ser Ser Gly Cys Pro Glu Arg Leu Ala Ser
            100                 105                 110

Cys Arg Ser Ile Asp Lys Phe Ala Gln Gly Trp Gly Pro Leu Thr Tyr
            115                 120                 125

Thr Glu Pro Asn Ser Ser Asp Gln Arg Pro Tyr Cys Trp His Tyr Ala
            130                 135                 140

Pro Arg Pro Cys Gly Ile Val Pro Ala Ser Gln Val Cys Gly Pro Val
145                 150                 155                 160

Tyr Cys Phe Thr Pro Ser Pro Val Val Val Gly Thr Thr Asp Arg Phe
            165                 170                 175

Gly Val Pro Thr Tyr Asn Trp Gly Ala Asn Asp Ser Asp Val Leu Ile
            180                 185                 190

Leu Asn Asn Thr Arg Pro Pro Arg Gly Asn Trp Phe Gly Cys Thr Trp
            195                 200                 205

Met Asn Gly Thr Gly Phe Thr Lys Thr Cys Gly Gly Pro Pro Cys Asn
            210                 215                 220

Ile Gly Gly Ala Gly Asn Asn Thr Leu Thr Cys Pro Thr Asp Cys Phe
225                 230                 235                 240

Arg Lys His Pro Glu Ala Thr Tyr Ala Arg Cys Gly Ser Gly Pro Trp
            245                 250                 255

Leu Thr Pro Arg Cys Met Val His Tyr Pro Tyr Arg Leu Trp His Tyr
            260                 265                 270

Pro Cys Thr Val Asn Phe Thr Ile Phe Lys Val Arg Met Tyr Val Gly
            275                 280                 285

Gly Val Glu His Arg Phe Glu Ala Ala Cys Asn Trp Thr Arg Gly Glu
            290                 295                 300

Arg Cys Asp Leu Glu Asp Arg Asp Arg Ser Glu Leu Ser Pro Leu Leu
305                 310                 315                 320

Leu Ser Thr Thr Glu Trp Gln Ile Leu Pro Cys Ser Phe Thr Thr Leu
            325                 330                 335

Pro Ala Leu Ser Thr Gly Leu Ile His Leu His Gln Asn Ile Val Asp
            340                 345                 350

Val Gln Tyr Leu Tyr Gly Val Gly Ser Ala Val Val Ser Leu Val Ile
            355                 360                 365

Lys
```

PARTICLES OF HCV ENVELOPE PROTEINS: USE FOR VACCINATION

The present application is a 371 U.S. national phase application of PCT/EP99/04342, filed Jun. 23, 1999.

FIELD OF THE INVENTION

The present invention is based on the finding that the envelope proteins of HCV induce a beneficial immune response in chimpanzees which are chronically infected with a heterologous subtype 1a or subtype 1b HCV strain. More specifically, the present invention relates to the finding that envelope proteins are highly immunogenic and result in the stimulation of both the cellular and humoral immune response. Moreover, the present invention relates to the finding that blocking of cysteines by alkylation results in even more immunogenic proteins. In addition, the envelope proteins of the present invention can be incorporated in particles which display a high imnmunogenecity and immunoreactivity. It was further demonstrated that such particles may incorporate other proteins.

BACKGROUND OF THE INVENTION

Hepatitis C virus (HCV) infection is a major health problem in both developed and developing countries. It is estimated that about 1 to 5% of the world population is affected by the virus. HCV infection appears to be the most important cause of transfusion-associated hepatitis and frequently progresses to chronic liver damage. Moreover, there is evidence implicating HCV in induction of hepatocellular carcinoma. Consequently, the demand for reliable diagnostic methods and effective therapeutic agents is high. Also sensitive and specific screening methods of HCV-contaminated blood-products and improved methods to culture HCV are needed.

HCV is a positive stranded RNA virus of approximately 9,600 bases which encode at least three structural and six non-structural proteins. Based on sequence homology, the structural proteins have been functionally assigned as one single core protein and two envelope proteins: E1 and E2. The E1 protein consists of 192 amino acids and contains 5 to 6 N-glycosylation sites, depending on the HCV genotype. The E2 protein consists of 363 to 370 amino acids and contains 9–11 N-glycosylation sites, depending on the HCV genotype (for reviews see: Major and Feinstone, 1997; Maertens and Stuyver, 1997). The E1 protein contains various variable domains (Maertens and Stuyver, 1997), while the E2 protein contains three hypervariable domains, of which the major domain is located at the N-terminus of the protein (Maertens and Stuyver, 1997). The latter envelope proteins have been produced by recombinant techniques in *Escherichia coli*, insect cells, yeast cells and mammalian cells. The usage of an expression system in higher eukaryotes and especially in mammalian cell culture leads to envelope proteins that are effectively recognized by antibodies in patient samples (Maertens et al., 1994).

It has been suggested that the E1 envelope protein needs the E2 envelope protein to reach a proper folding status (Deleersnyder et al., 1997). In addition, it has been suggested that E1 and E2 form heterodimers which may form the basic unit of the viral envelope (Yi et al., 1997). In WO 98/21338 to Liang et al. these presumptions have been used to construct HCV particles, which consist of E1 and E2, as well as Core and P7. In other words, the usage of E1 or E2 separately for immunization and other purposes is not suggested in the prior art. But, Houghton (1997) reported that repeated immunizations with recombinant gpE1E2 (4×25 μg) of 3 chronically HCV-infected chimpanzees did not induce a significant immune response. The inventors of the present application reasoned that the induction of an anti-envelope immune response in patients with chronic hepatitis C would indeed be desirable and beneficial to the patient, since higher levels of such antibodies seem to correlate with good response to interferon therapy, and may therefore help the patient to clear the virus (PCT/EP 95/03031 to Maertens et al.). The inventors of the present invention further reasoned that, as the antibody levels against E1 in chronic HCV carriers are among the lowest of all HCV antibodies, it may be beneficial to raise those antibody levels, and possibly the cellular response, to induce control or even clearance of the infection by the host. Also higher levels of cellular immunity against E1 seem to correlate with good response towards interferon therapy (Leroux-Roels et al., 1996).

Besides the importance of anti-E1 immunity in relation to interferon therapy, other indications point-out that some other parts of the HCV genome may be important to induce a specific immune response which may allow control of the infection. Also T-cell reactivity against the C-terminal region of the core protein has been observed more frequently in patients responding to interferon therapy (Leroux-Roels et al, 1996). Potentially neutralizing antibodies against the NS4B protein were demonstrated in patients clearing HCV after liver transplant (Villa et al., 1998). Also within NS3 several T-cell epitopes have been mapped which seem to correlate with clearing of HCV during the acute phase (see: PCT/EP 94/03555 to Leroux-Roels et al.; Leroux-Roels et al., 1996; Rehermann et al., 1996 and 1997; Diepolder et al., 1995and 1997). Furthermore, antibodies to NS5A, like E1 antibodies, show higher levels at baseline before interferon-alpha therapy in long term responders (LTR) as compared to non-responders.

At present, therapeutic vaccination for HCV has not been successful. Also prophylactic vaccination has only been shown to be effective against a homologous strain of HCV (Choo et al., 1994). The present invention relates to the surprising finding that administration of an HCV envelope antigen can dramatically improve the state of chronic active hepatitis in an individual infected with a heterologous strain or isolate, both in a heterologous subtype 1a or heterologous subtype 1b infection. Indeed, chronically infected chimpanzees who were administered six doses of 50 μg E1s (i.e. aa 192–326 of E1) surprisingly showed vigourous humoral and cellular immune responses, which had not been mounted over the entire period of chronic infection before the latter vaccination. Moreover, viral antigen became undetectable in the liver over a period of two to five months and remained undetectable for at least 5 months post-vaccination. Although HCV-RNA titers in the serum did not decrease, liver enzyme levels in the serum showed a clear tendency to normalize. Most importantly, liver histology improved dramatically in both vaccinees. The present invention further relates to the surprising finding that the E1 protein used for vaccination, which was expressed as a single HCV protein without its hydrophobic anchor, forms stable particles. It should also be noted that, to avoid induction of an immune response against non-relevant epitopes, the E1 protein used for vaccination was constructed as a consensus sequence of individual clones derived from a single serum sample from one chronic carrier. In addition, the present application relates to the finding that the induction of such anti-E1 responses may be increased by using antigens of a different genotype than the ones of the infection present in the host. Moreover, the present application relates to the finding that when cysteines of HCV envelope proteins are alkylated, for instance, by means of N-(iodoethyl)-trifluoroacetamide, ethylenimine or active halogens, such as iodoacetamide, the oligomeric particles as described above display an even higher immunogenicity. Finally, the present invention relates also to the finding that mutation of cysteines of HCV envelope proteins to any other naturally occuring amino acid, preferentially to methionine, glutamic acid, glutamine or lysine, in the oligomeric particles as described above also results in higher immunogenicity, compared to the originals envelope proteins.

AIMS OF THE INVENTION

It is clear from the literature that there is an urgent need to develop reliable vaccines and effective therapeutic agents for HCV. Therefore, the present invention aims at providing an antigen preparation, which is able to induce specific humoral and cellular immunity to HCV envelope proteins, even (but not solely) in chronic HCV carriers. The same antigens can be used for diagnosis of the immune response.

More specifically, the present invention aims at providing an antigen preparation as defined above, which consists of stable particles of single envelope proteins of HCV. It should be clear that, at present, such particles or a method to prepare such particles, are not known in the art. Moreover, there is no indication in the art that any antigen preparation, including such stable particles or such purified single HCV envelope proteins, could successfully be used as (heterologous) prophylactic or therapeutic vaccine against HCV. The present invention thus also aims at providing a method to produce stable particles, which can be successfully used as a prophylactic or therapeutic agent against HCV, in addition to provide DNA vaccines encoding HCV antigens. More specifically, the present invention aims at providing a method to produce the latter particles based on detergent-assisted particle formation (see further). Furthermore, the present invention aims at providing methods to prepare particles consisting of antigens obtained from different HCV genotypes.

Moreover, the present invention aims at providing an antigen which is a consensus sequence from individual clones, which may allow a more correct folding of the proteins. This in order to avoid stimulation of immunity against non-relevant epitopes.

Furthermore, the present invention aims at providing an antigen formulation, in particular for therapeutic vaccination, based on the genotype of HCV by which the chronic carrier is infected. In this regard, the present invention aims at providing an envelope protein of either a different or a homologous genotype or subtype compared to the genotype or subtype of the chronic carrier.

A further aim of the invention is to provide a method for treating or therapeutically vaccinating chronically infected patients using the above-indicated antigens or DNA vaccines, possibly in combination with other compounds. The present invention also aims to provide a method to prophylactically vaccinate humans against HCV.

Another aim of the invention is to provide oligomeric particles which have a superior immunogenicity, due to the mutation of at least one cysteine residue of HCV envelope protein into a natural occuring amino acid, preferentially methionine, glutamic acid, glutamine or lysine. Alternatively, alkylation of at least one cysteine residue of HCV envelope protein may be performed. In particular, the latter protein can be alkylated by means of ethylenimine, N-(iodoethyl)trifluoroacetamide or active halogens. In this regard, the instant invention aims to provide the additional use of oligomeric particles as vehicles for presenting non-HCV epitopes efficiently.

It is a further aim of the present invention to provide a method to treat patients, acutely or chronically infected, with an anti-envelope antibody, such as anti-E1 antibody, e.g. anti-E1 V2 region antibody, either alone or in combination with other treatments.

Another aim of the invention is to provide a T cell stimulating antigen such as Core, E1, E2, P7, NS2, NS3, NS4A, NS4B, NS5A, or NS5B along with the envelope proteins of the invention.

All the aims of the present invention are considered to have been met by the embodiments as set out below.

BRIEF DESCRIPTION OF TABLES AND DRAWINGS

Table 1 provides sequences of E1 clones obtained from a single chronic carrier, the E1 construct used for production of a vaccine is the consensus of all these individual clones. V1–V5, variable regions 1–5; C4, constant domain 4; HR, hydrophobic region; HCV-B con, consensus sequence at positions that are variable between clones and HCV-J.

Table 2 provides sequences of the E1 vaccine protein and the E1 protein as found in the infected chimpanzees Phil and Ton. The subtype 1b isolate of Phil differed by 5.92% from the vaccine strain. The difference between the vaccine and the subtype 1a isolate of Ton was 20.74%.

Table 3 provides a schematic overview of the changes induced by therapeutic vaccination in two chronically infected chimpanzees (Ton and Phil). Analysis was performed as explained for FIGS. 8 and 11. In addition, histology and inflammation were scored from the liver biopsies.

Table 4 provides sequences of peptides used to map the B-cell epitopes. Note that HR overlaps with V4V5.

Table 5 shows the rearrangement of NS3 in order to make a shorter protein carrying all major epitopes correlating with viral clearance.

Table 6 shows the reactivity in LIA of E1s-acetamide versus E1s-maleimide with sera of chronic HCV carriers. Proteins were immobilized on the LIA membranes. E1s-acetamide was sprayed as such on the LIA strips while E1s-maleimide (also containing biotin-maleimide) was complexed with streptavidin before spraying. Antigens were bound to LIA-membranes, and strips were processed essentially as described in Zrein et al. (1998). Human antibodies directed against these antigens were visualized using a human-anti-IgG conjugated with alkaline phosphatase. NBT and BCIP were used for color development of the strip. Staining was scored from 0.5 to 4, as explained in Zrein et al. (1998). Using a cut-off for this assay of 0.5 the number of positive samples (#pos) and percentage (%pos) is mentioned at the bottom of the table.

FIG. 1. Superimposed size exclusion chromatography profiles in PBS/3% Empigen-BB of E1s and E2s proteins expressed and purified according to Maertens et al. (PCT/EP95/03031)

Figure 2:
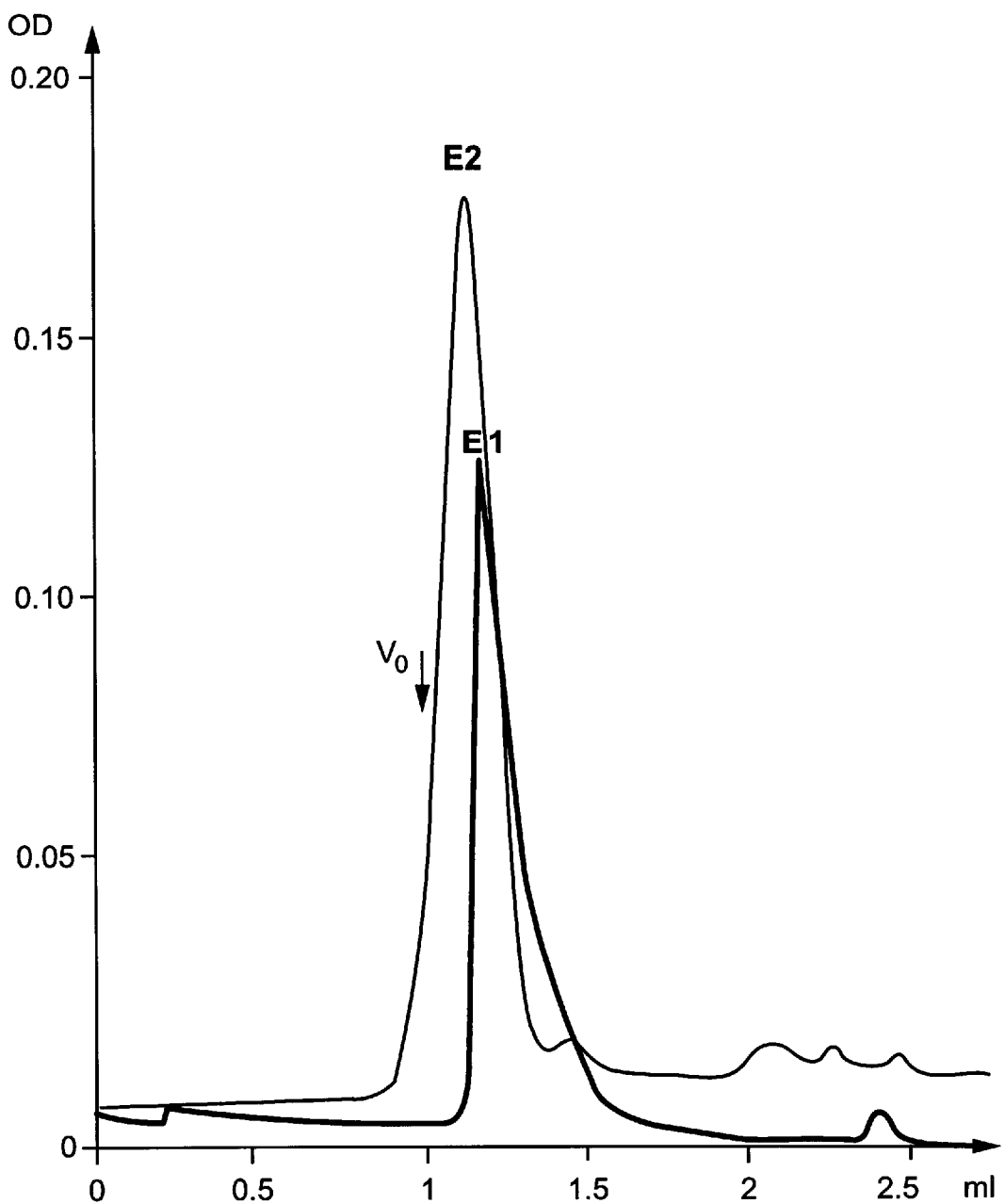

FIG. 2. Superimposed size exclusion chromatography (SEC) profiles of E1s and E2s proteins expressed and purified according to Maertens et al. (PCT/EP95/03031), and submitted to another run on the same SEC column in PBS/0.2% CHAPS, to obtain specific oligomeric structures of an estimated apparent molecular weight of 250–300 kDa. Similar degrees of association can be obtained by using 3% betaine.

Figure 3:
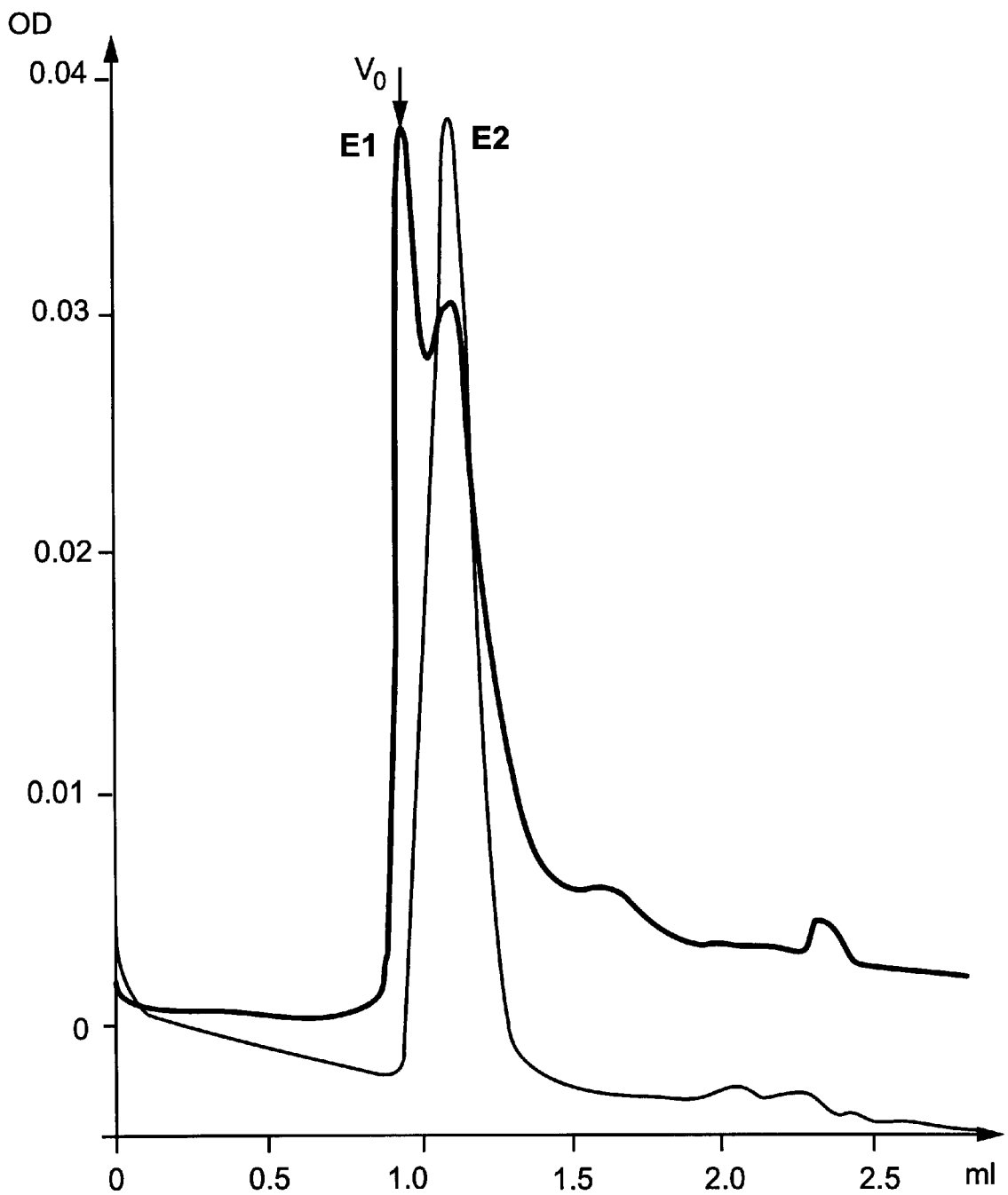

FIG. 3. Superimposed size exclusion chromatography profiles of E1s and E2s proteins expressed and purified according to Maertens et al. (PCT/EP95/03031), submitted to a second run in 0.2% CHAPS or 3% betaine to obtain specific oligomeric structures as shown in FIG. 2, and submitted to a third run on the same SEC column in 0.05% CHAPS, to obtain specific homo-oligomeric structures with an estimated apparent molecular weight of 250–300 kDa (E2s) and >600 kDa (E1s). Similar degrees of association can be obtained by using 0.1 or 0.5% betaine.

Figure 4:
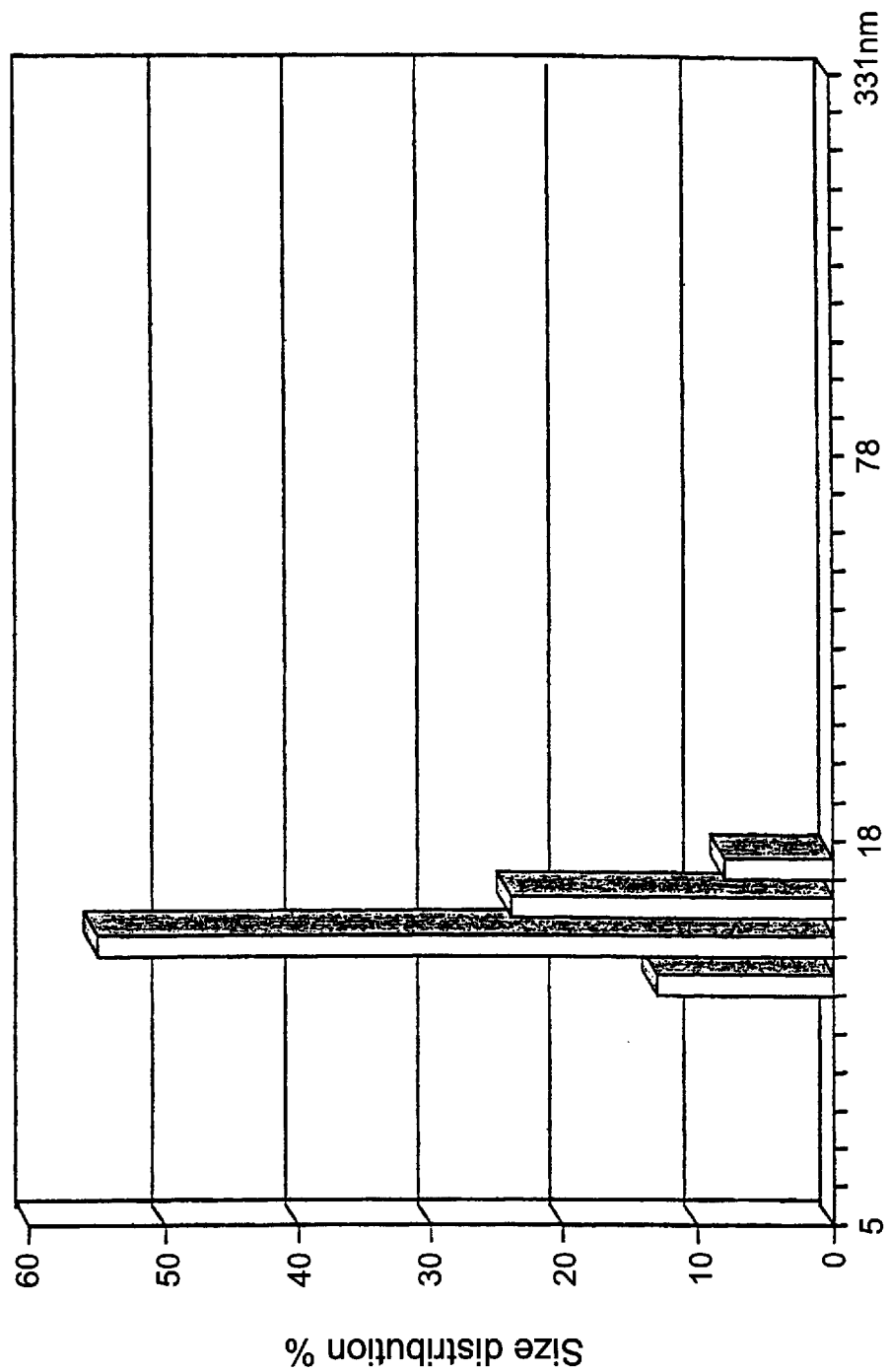

FIG. 4 Dynamic light scattering analysis, expressed as percentage of the number of particles in relation to the observed diameter in nm, of E1s in PBS/0.05% CHAPS.

Figure 5:
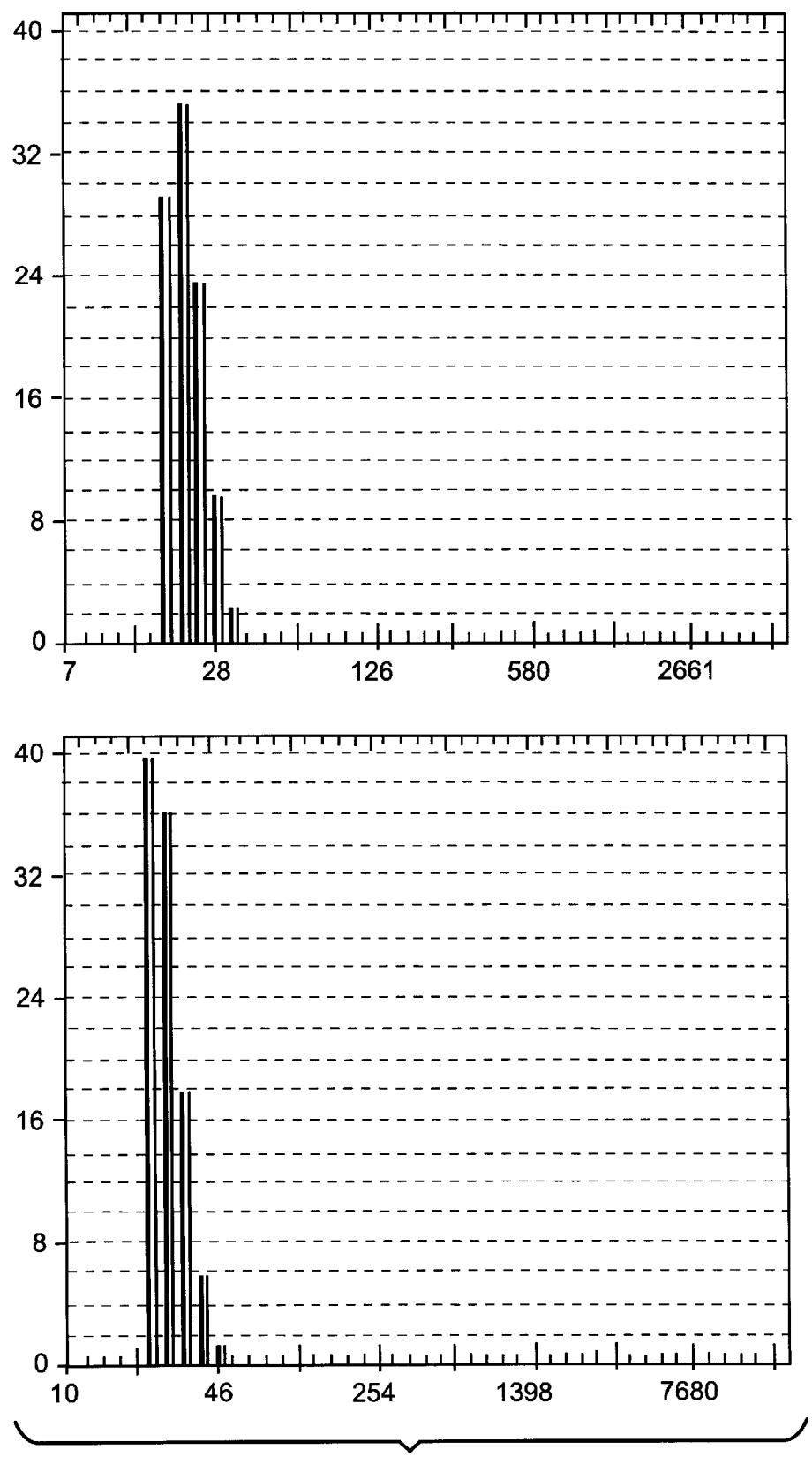

FIG. 5 Dynamic light scattering analysis, expressed as percentage of the number of particles in relation to the observed diameter in nm, of E1s in PBS/0.1% betaine (top) or 0.5% betaine (bottom).

Figures 6A, 6B:
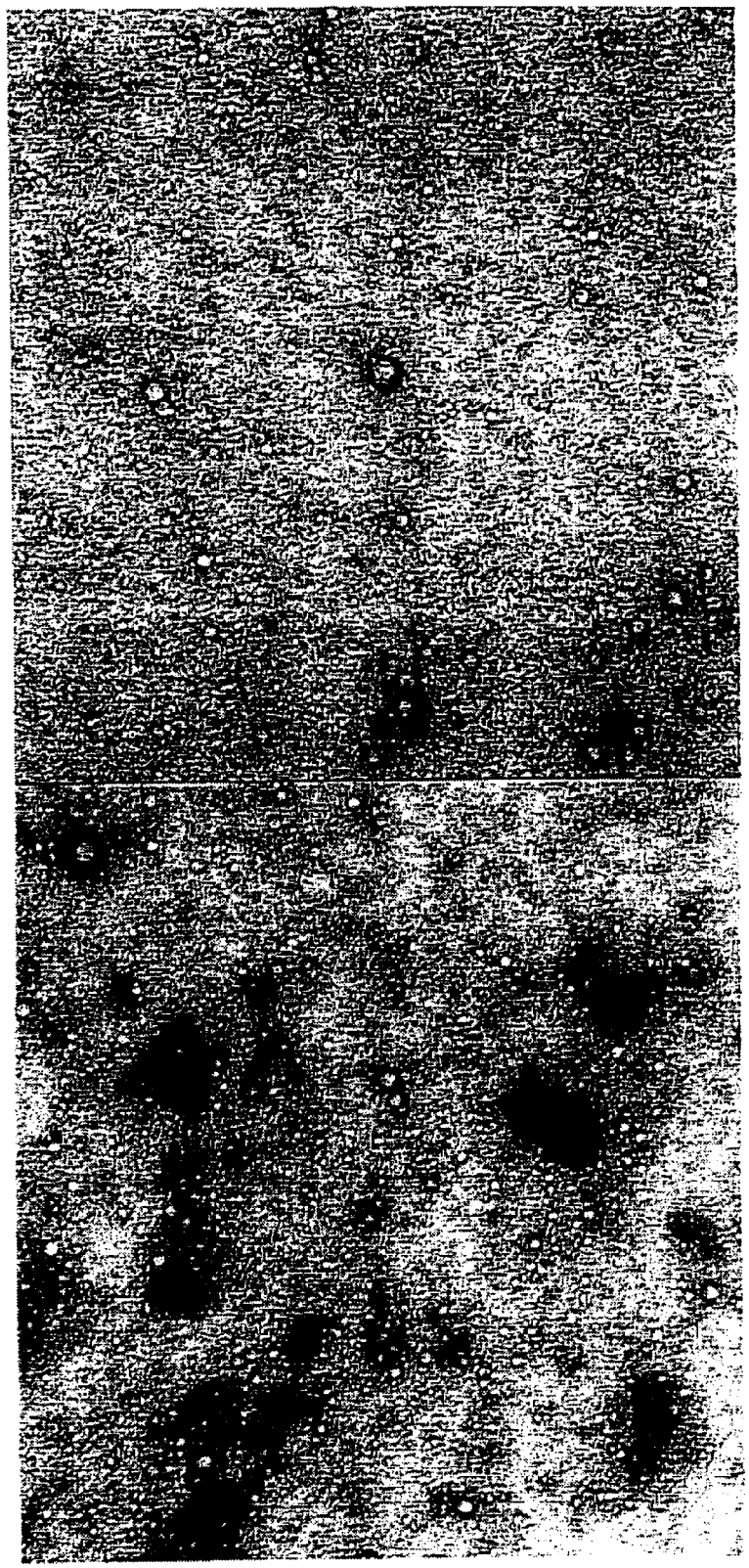

FIG. 6 EM staining of (A) E1s in PBS/0.05% CHAPS and (B) E1s in PBS/3% betaine.

Figure 7:
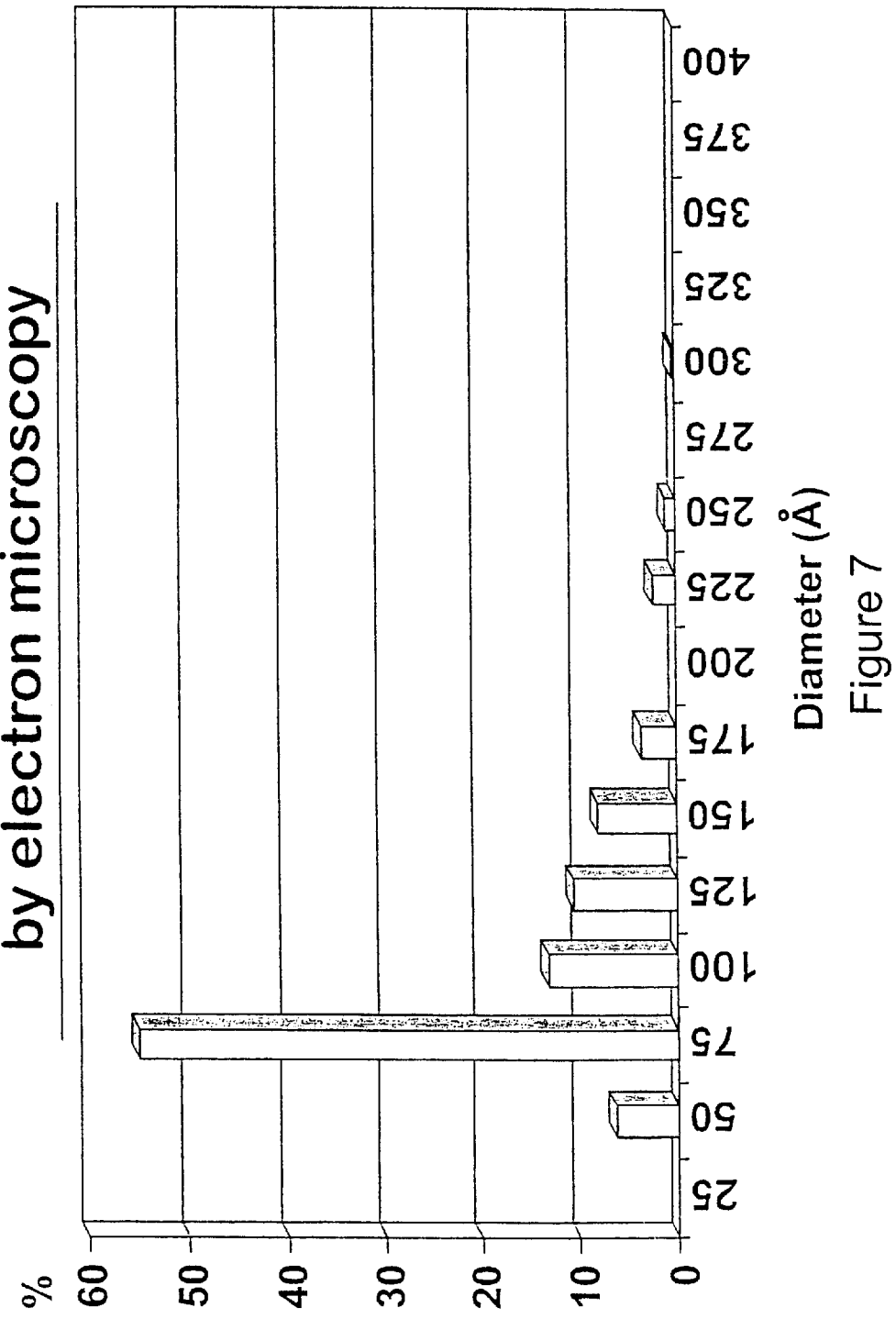

FIG. 7 Size distribution of particles of E1s in PBS/0.05% CHAPS.

Figure 8:
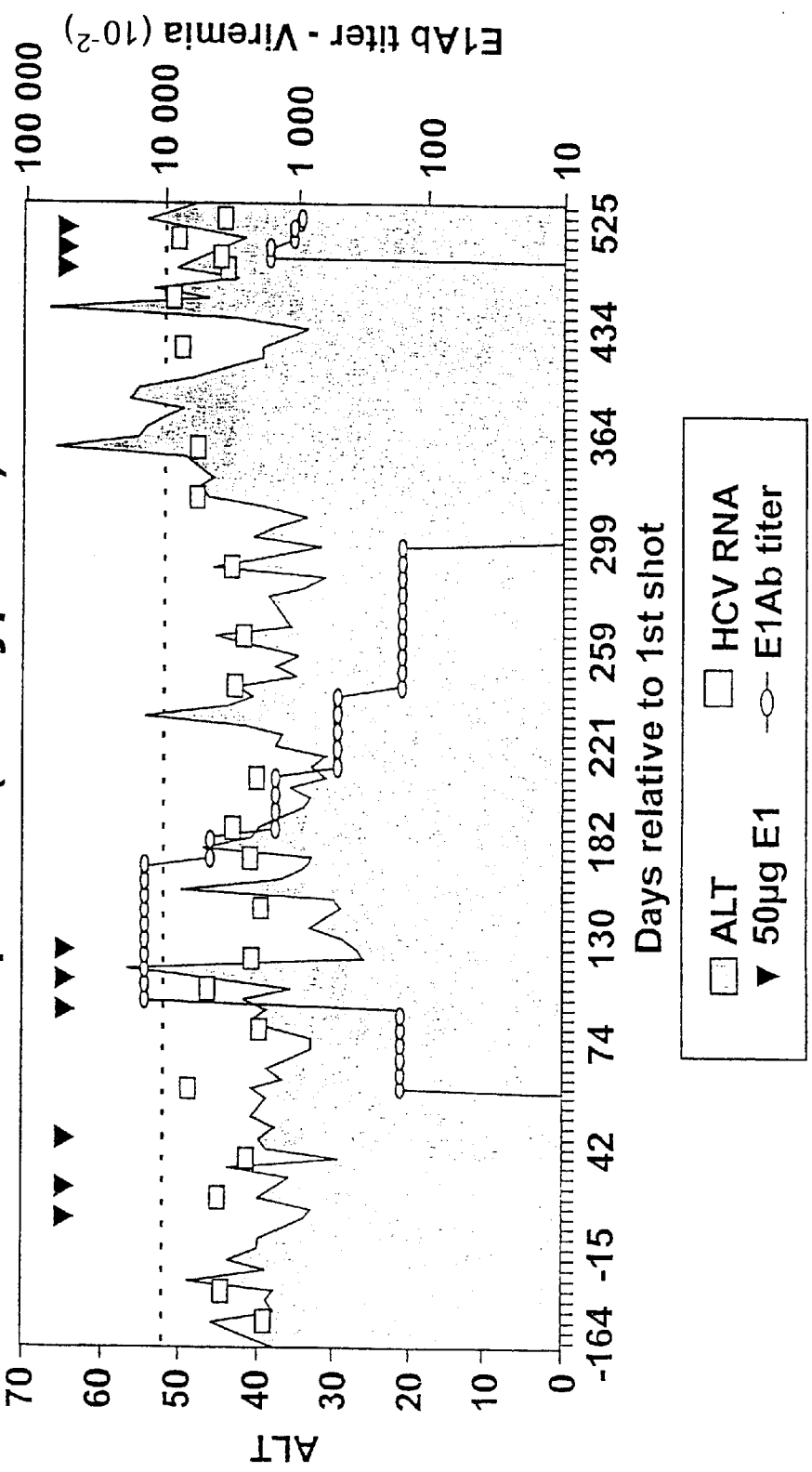

FIG. 8 Evolution of anti-E1 antibodies induced by six consecutive and 3 boost immunizations (indicated by small arrows) in a 1b infected chimpanzee (Phil), and the evolution of ALT, HCV RNA, and anti-E1 antibodies. Anti-E1 antibodies binding to solid phase E1 were detected using an anti-human IgG specific secondary antiserum conjugated with peroxidase. TMB was used as substrate for colour development. The results are expressed as end-point titer. ALT levels were determined with a clinical analyser, and are expressed as U/l. HCV RNA in serum was determined using HCV Monitor (Roche, Basel, Switzerland). Viral load in the liver was determined by semi-quantitative determination of the amount of E2 antigen stained in the liver biopsy using a specific monoclonal (ECACC accession number 98031215 as described in EP application No 98870060.5).

Figure 9:
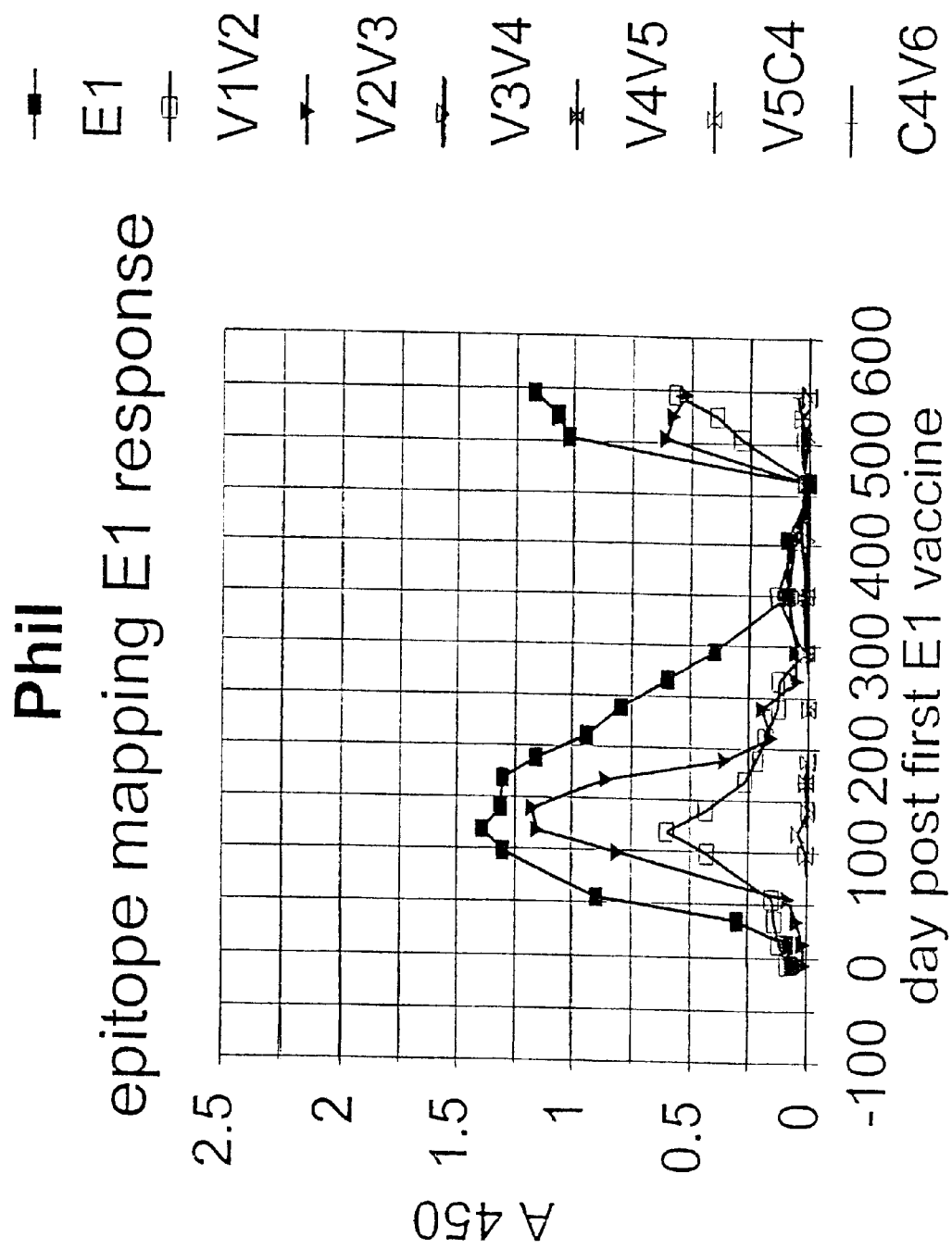

FIG. 9 Epitope mapping of the antibody responses induced by immunization with E1 in chimpanzee Phil. Antibodies reactivity towards the various peptides was measured by an indirect ELISA in which biotinylated peptides (see also Table 4) are adsorbed on the microtiterplates via streptavidin. Specific antibodies are detected using an anti-human IgG specific secondary antiserum conjugated with peroxidase. TMB was used as substrate for colour development.

Figure 10:
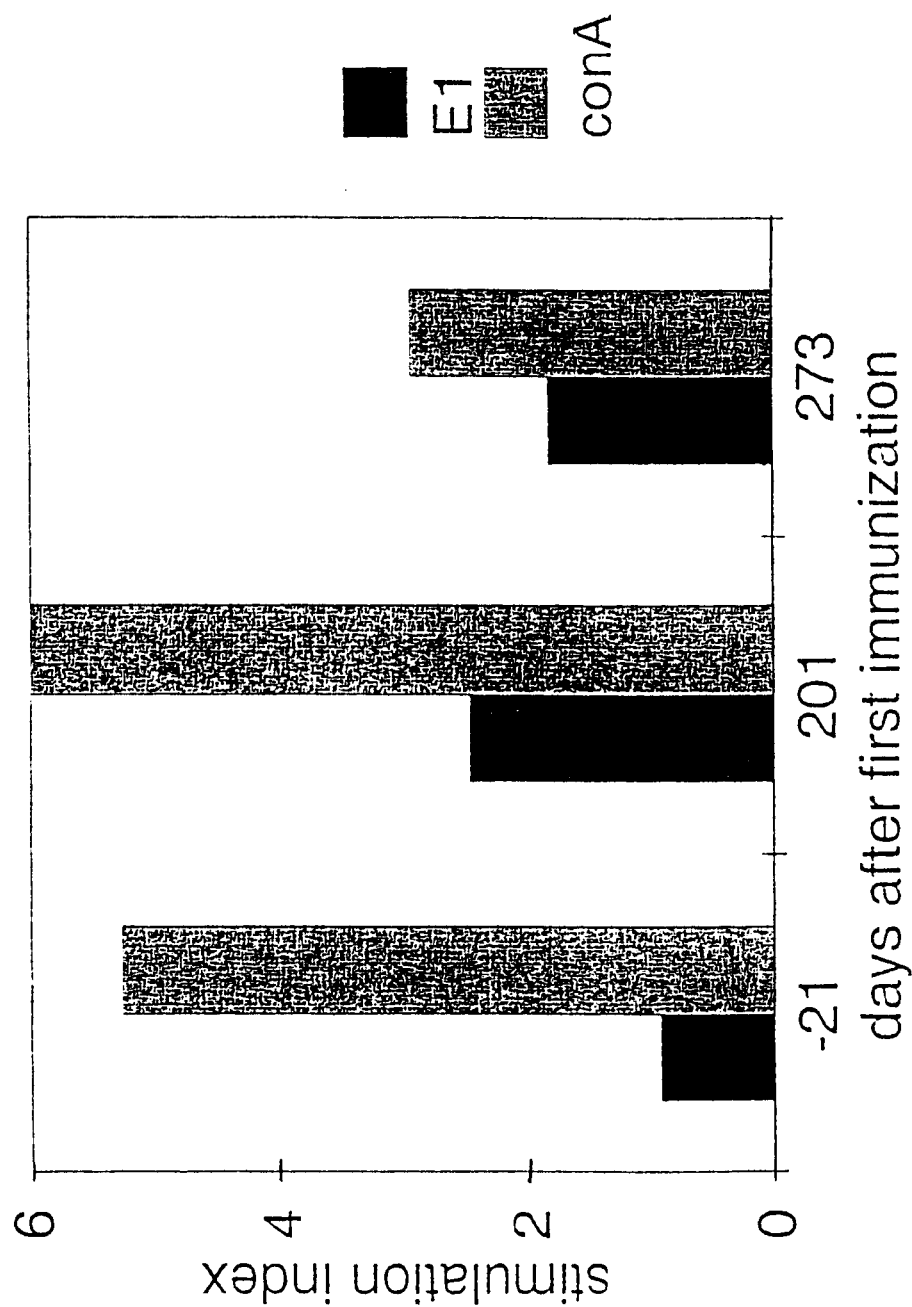

FIG. 10 Results of the lymphocyte proliferation assay before and after vaccination in chimpanzee Phil. Frozen PBMC were thawed and stimulated in triplicate with different antigens. Negative control was medium alone, while concanavalin A was used as positive control at a concentration of 5 $\mu$g/ml. PBMC at a concentration of 2–4×10$^5$ cells/well in a total volume of 150 $\mu$l were cultured in RPMI 1640 medium supplemented with 10% heat-inactivated FCS in U-shaped 96-well microtiterplates together with the controls or 1 $\mu$g/ml of E1 for 90h at 37° C. in a humidified atmosphere containing 5% $CO_2$. During the last 18 h the cells were pulsed with 0.5 $\mu$Ci ($^3$H) thymidine per well. Subsequently, the cultures, were harvested on glass fibre filters and label uptake was determined. Results are expressed as Stimulation Indices (SI): mean cpm antigen/ mean cpm medium alone of triplicate determinations.

Figure 11:
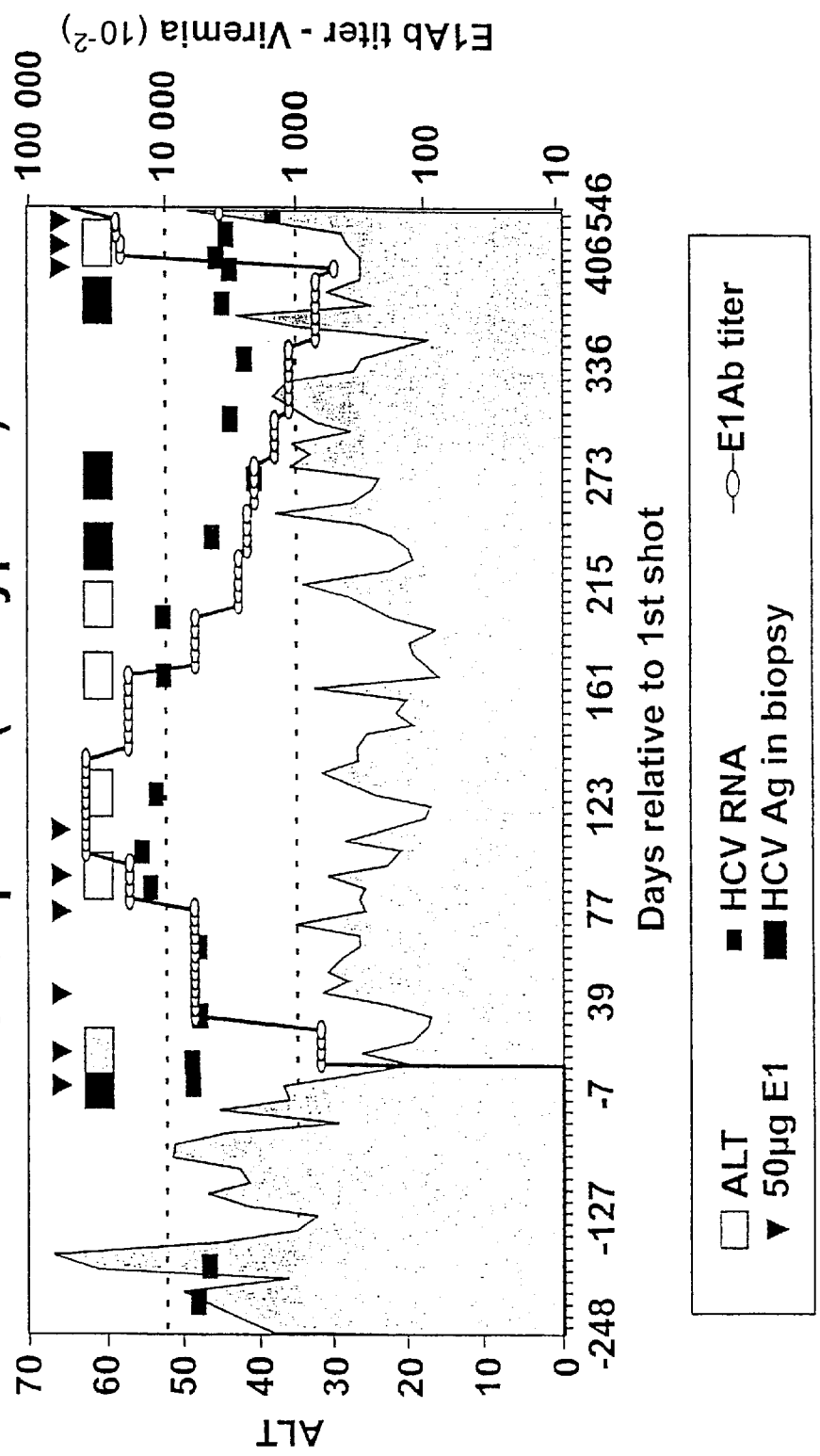

FIG. 11 Evolution of anti-E1 antibodies induced by six consecutive and 3 boost immunizations (indicated by small arrows) in HCV subtype 1a infected chimpanzee Ton. Evolution of ALT, HCV RNA in serum and determination of HCV antigen in liver are shown. Anti-E1 antibodies were determined by means of an indirect ELISA: specific antibodies binding to solid phase-coated E1 are detected using a anti-human IgG specific secondary antiserum conjugated with peroxidase. TMB was used as substrate for color development. The results are expressed as end-point titres. ALT levels were determined with a clinical analyser, and are expressed as U/l. HCV RNA was determined using HCV Monitor (Roche, Basel, Switzerland). E2 antigen was stained in the liver biopsy using a specific monoclonal (ECACC accession number 98031215 as described in EP application No. 98870060:5). The semi-quantitative scoring is indicated by black squares for clearly positive staining in the majority of the cells, by grey squares for clear staining in the minority of the cells and by white squares for biopsies showing no detectable staining. HCV RNA is indicated by small black boxes. Staining of E2 could be confirmed by Core and E1 staining (data not shown).

FIG. 12 Epitope mapping of the antibody response induced by immunization with E1 in Ton. Antibodies reactivity towards the various peptides was measured by an indirect ELISA in which biotinylated peptides (see also Table 4) are adsorbed on the microtiterplates via streptavidin. Specific antibodies are detected using an anti-human IgG specific secondary antiserum conjugated with peroxidase. TMB was used as substrate for color development.

FIG. 13 Analysis of E1 antibody responses to subtype 1a and subtype 1b E1 proteins in chimpanzee Ton. For this purpose an E1 genotype 1a, derived from the HCV-H sequence, recombinant vaccinia virus was generated expressing the same part of E1 as for genotype 1b (see infra). E1 was derived from crude lysates from vaccinia virus infected RK13 cells (prepared as described in Maertens et al. (PCT/EP95/03031)). Antibody reactivity was measured by an indirect ELISA in which E1 was adsorbed on the microtiterplates via the high-mannose binding Galanthus nivalis agglutinin (GNA). Specific antibodies were detected using an anti-human IgG specific secondary antiserum conjugated with peroxidase. TMB was used as substrate for colour development. The results are expressed as differential OD (OD of well with adsorbed E1 minus OD of well without adsorbed E1).

Figure 14:
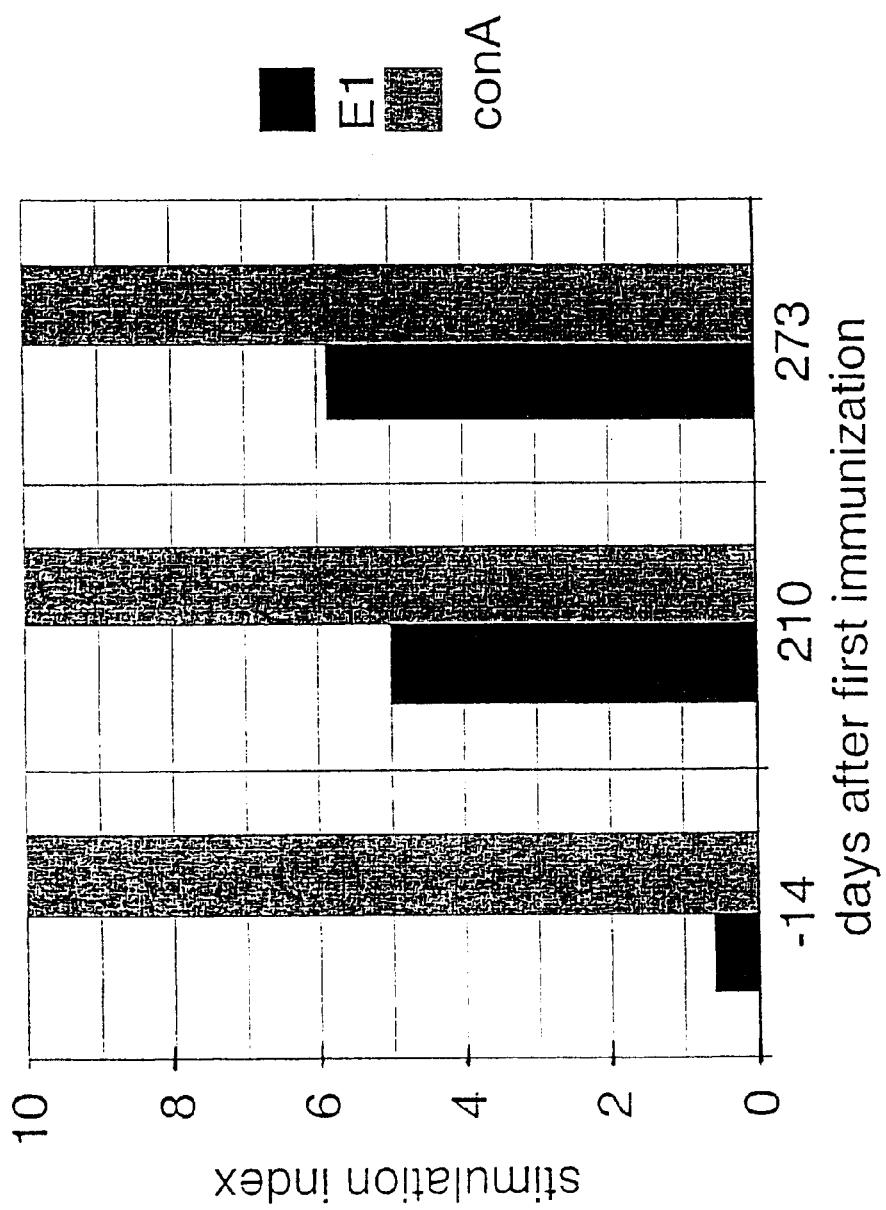
Figure 15A:
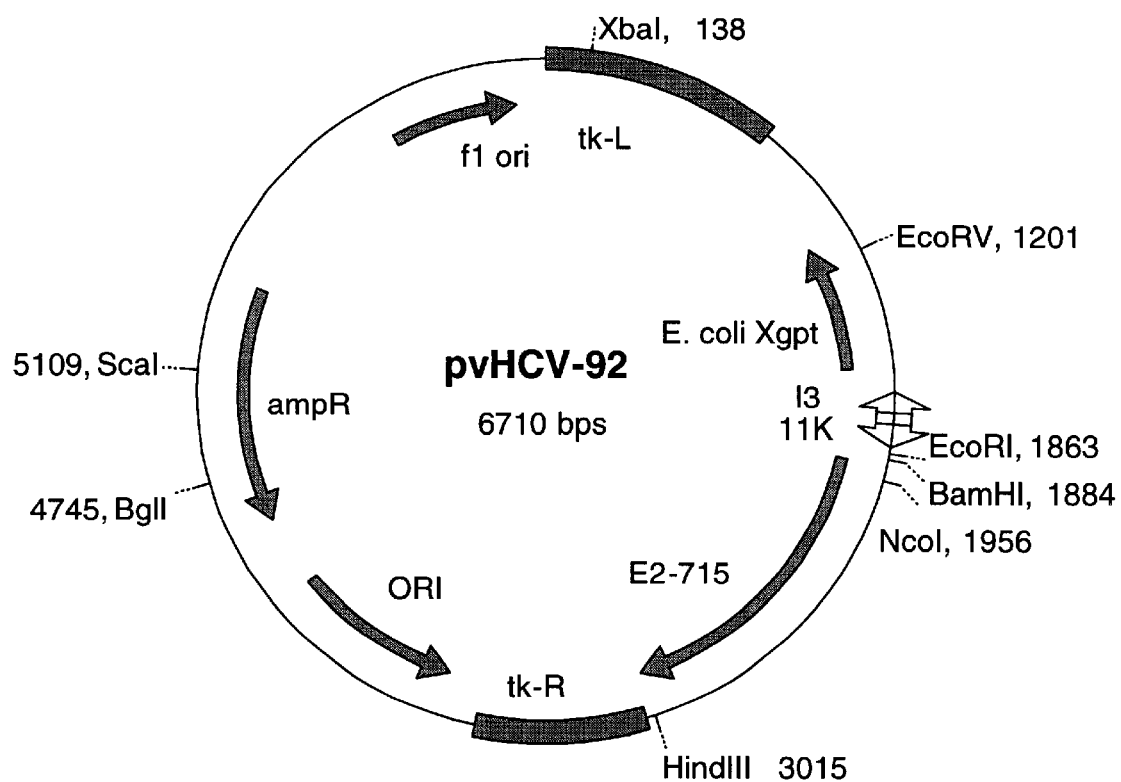
Figure 15B:
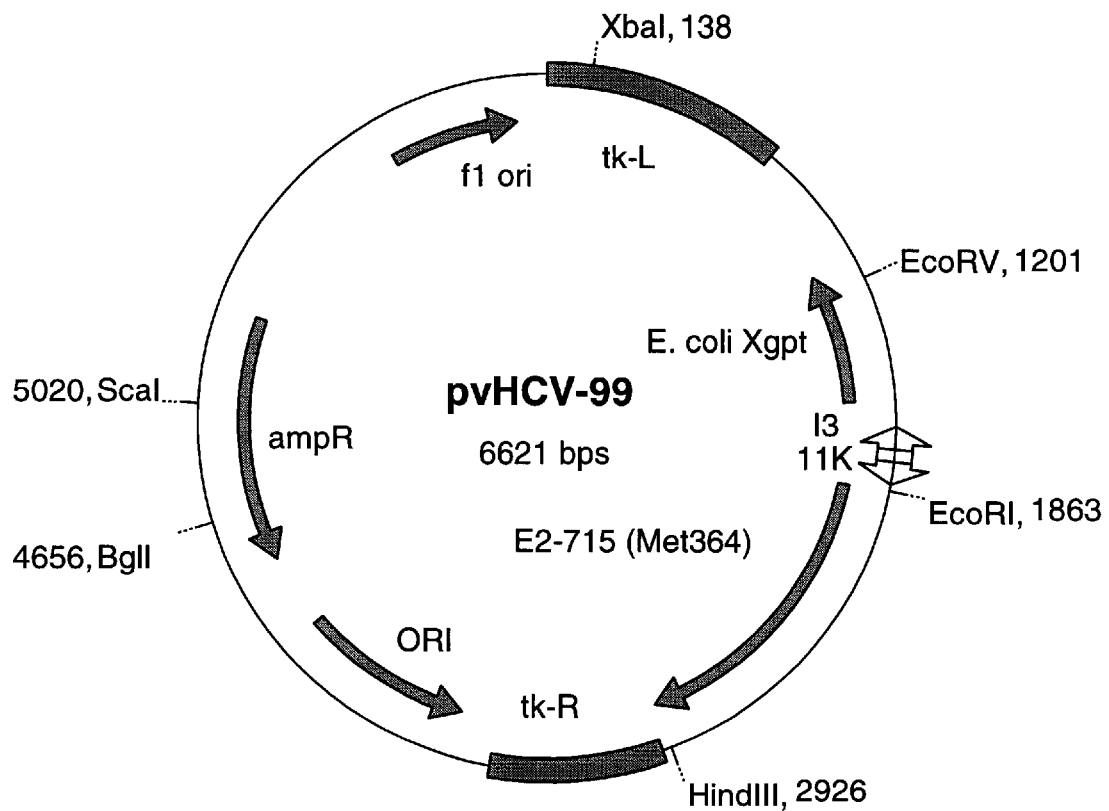
Figure 15C:
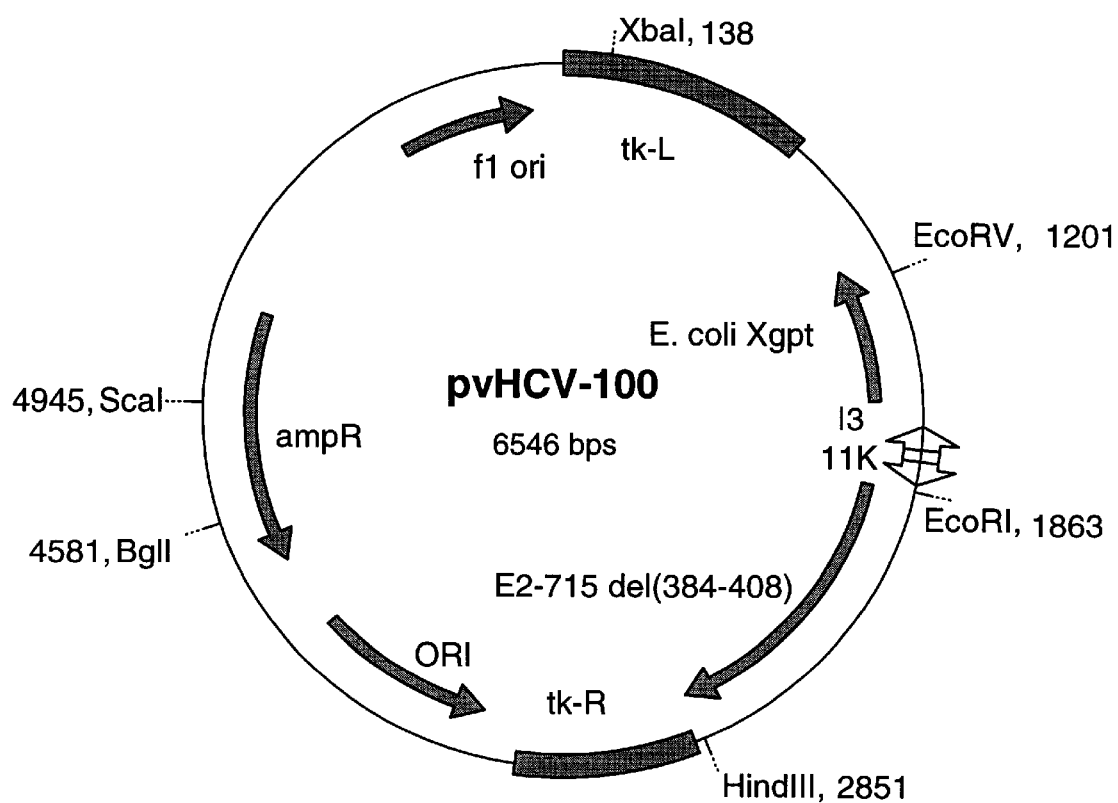
Figure 15D:
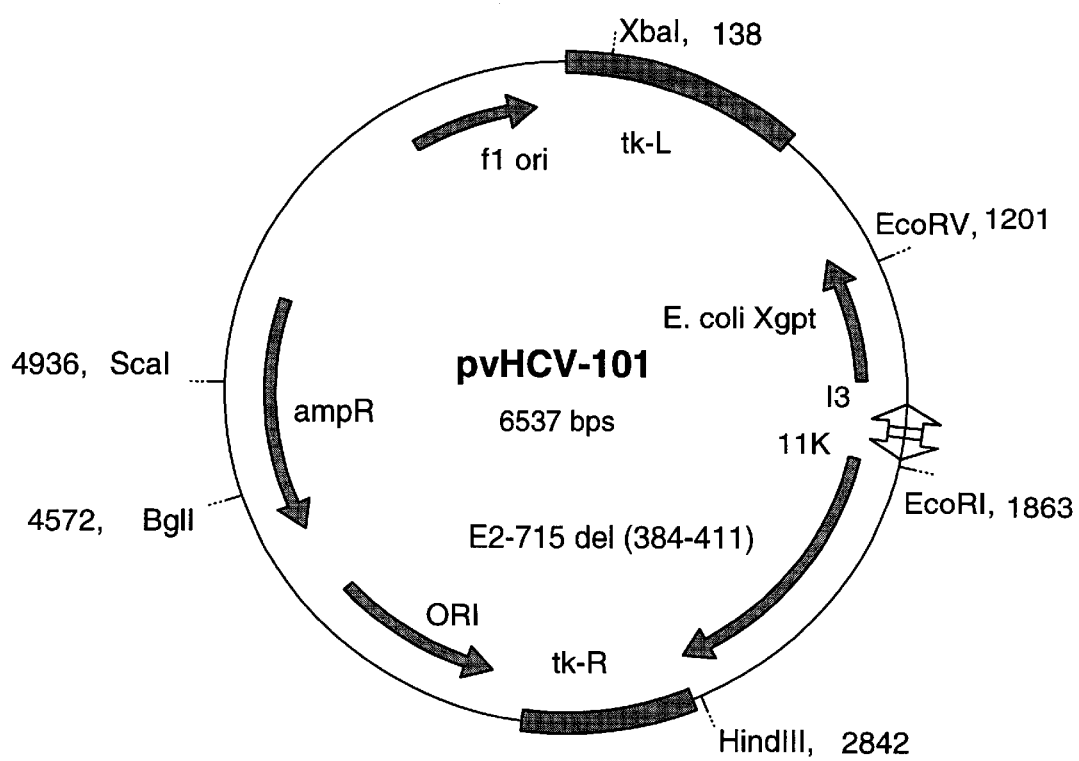

FIG. 14 Results of the lymphocyte proliferation assay before and after vaccination of chimpanzee Ton. Frozen PBMC were thawed and stimulated in triplicate with different antigens. Negative control was medium alone, while concanavalin A was used as positive control at a concentration of 5 $\mu$g/ml. PBMC at a concentration of 2–4 10$^5$ cells/well in a total volume of 150 $\mu$l were cultured in RPMI 1640 medium supplemented with 10% heat-inactivated PCS in U-shaped 96-well microtiterplates together with the controls or 1 $\mu$g/ml of E1 for 90h at 37° C. in a humidified atmosphere containing 5% $CO_2$. During the last 18 h the cells are pulsed with 0.5 $\mu$Ci ($^3$H) thymidine per well. Subsequently, the cultures, are harvested on glass fibre filters and label uptake is determined. Results are expressed as Stimulation Indices (SI): mean cpm antigen/mean cpm medium alone of triplicate determinations.

FIG. 15 Maps of the constructs used to obtain expression of an E2 protein with its N-terminal hypervariable region deleted. Constructs pvHCV-92 and pvHCV-99 are intermediate constructs used for the construction of the deletion mutants pvHCV-100 and pvHCV-101.

FIG. 16 Sequence (nucleotides: A(SEQ ID NO:28); translation: B(SEQ ID NO:29)) corresponding with the constructs depicted in FIG. 15 (see above).

Figure 17:
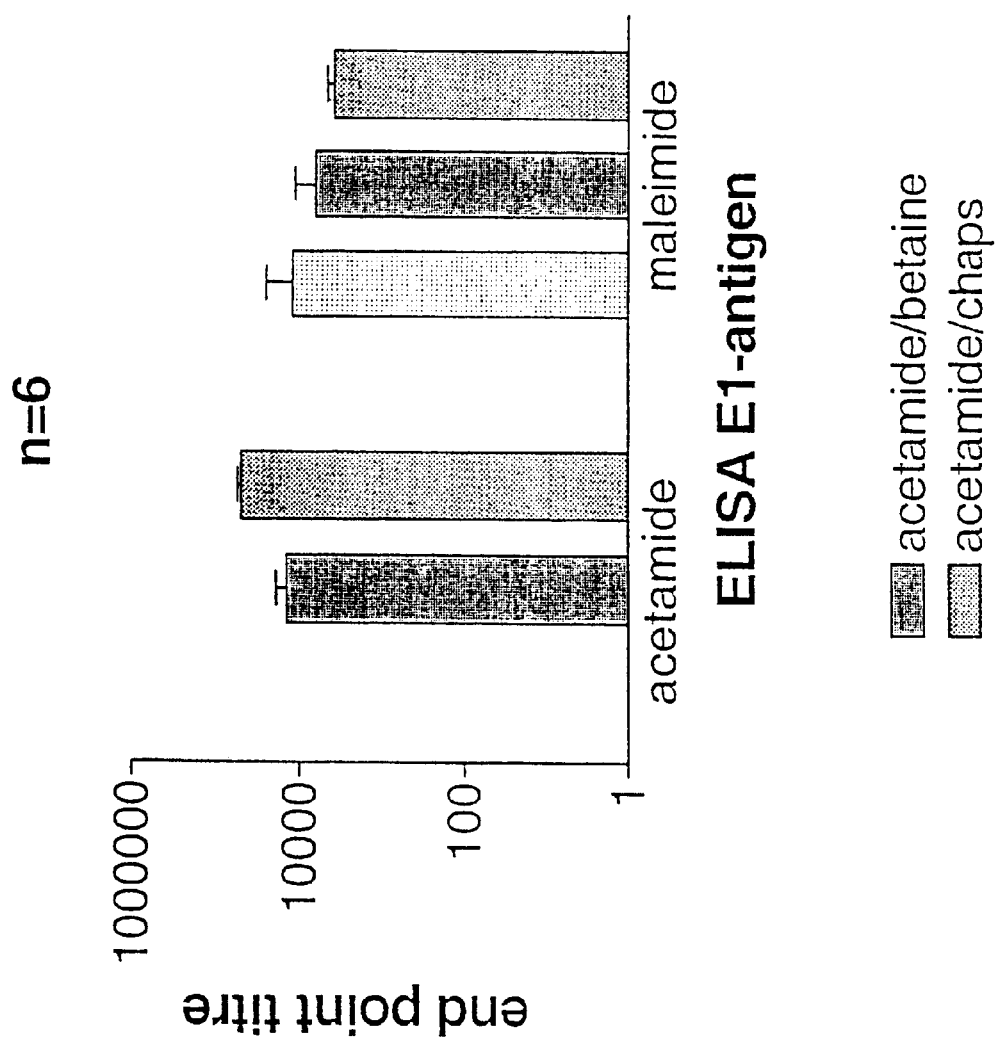

FIG. 17 Antibody titers obtained in mice upon immunization with different E1 preparations as described in example 9. Titers were determined by means of ELISA: murine sera were diluted 1/20 and further on (0.5 $\log_{10}$) and incubated on E1s (either acetamide or maleimide modified) coated on microtiterplates. After washing binding antibodies are detected using an anti-mouse IgG specific secondary antiserum conjugated with peroxidase. TMB was used as substrate for colour development. The results are expressed as end-point titer and standard deviations are shown (n=6).

Figure 18:
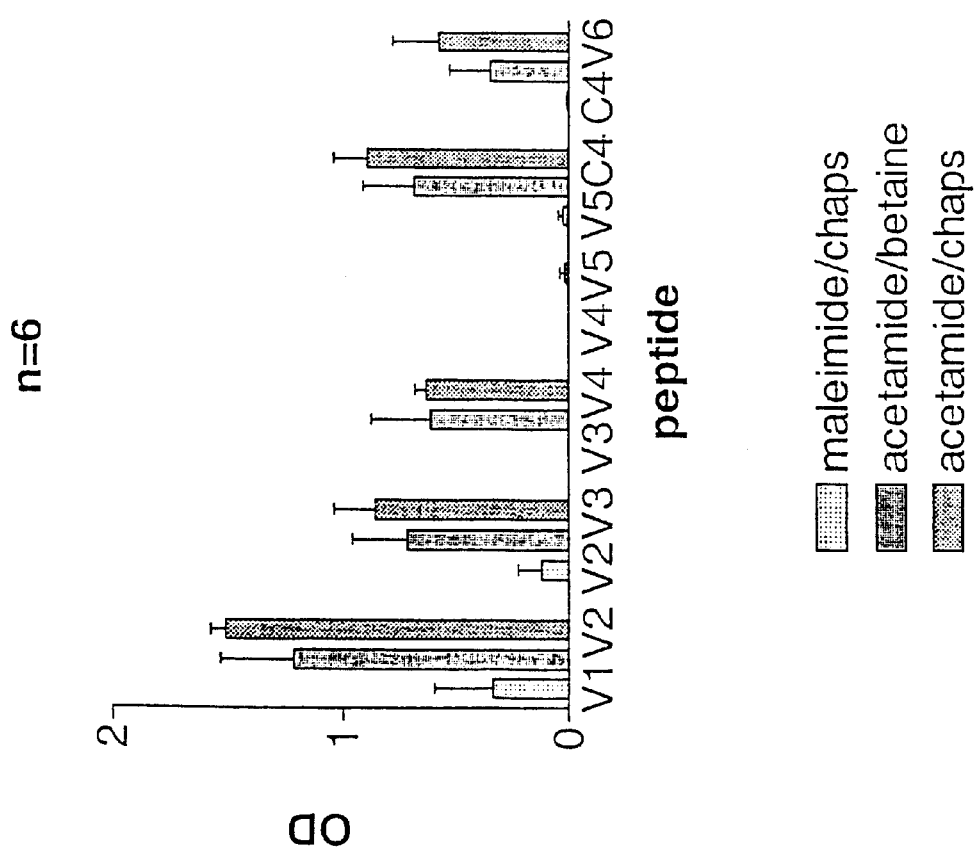

FIG. 18 Epitope mapping of the antibody response induced by immunization with different E1s preparations in mice. Antibody reactivity towards the various peptides was measured by an indirect ELISA, in which biotinylated peptides (listed in Table 4) are adsorbed on the microtiterplates via streptavidin. Murine sera were diluted 1/20 and specific antibodies are detected using an anti-mouse-IgG specific secondary antiserum conjugated with peroxidase. TMB was used as substrate for colour development.

Figure 19:
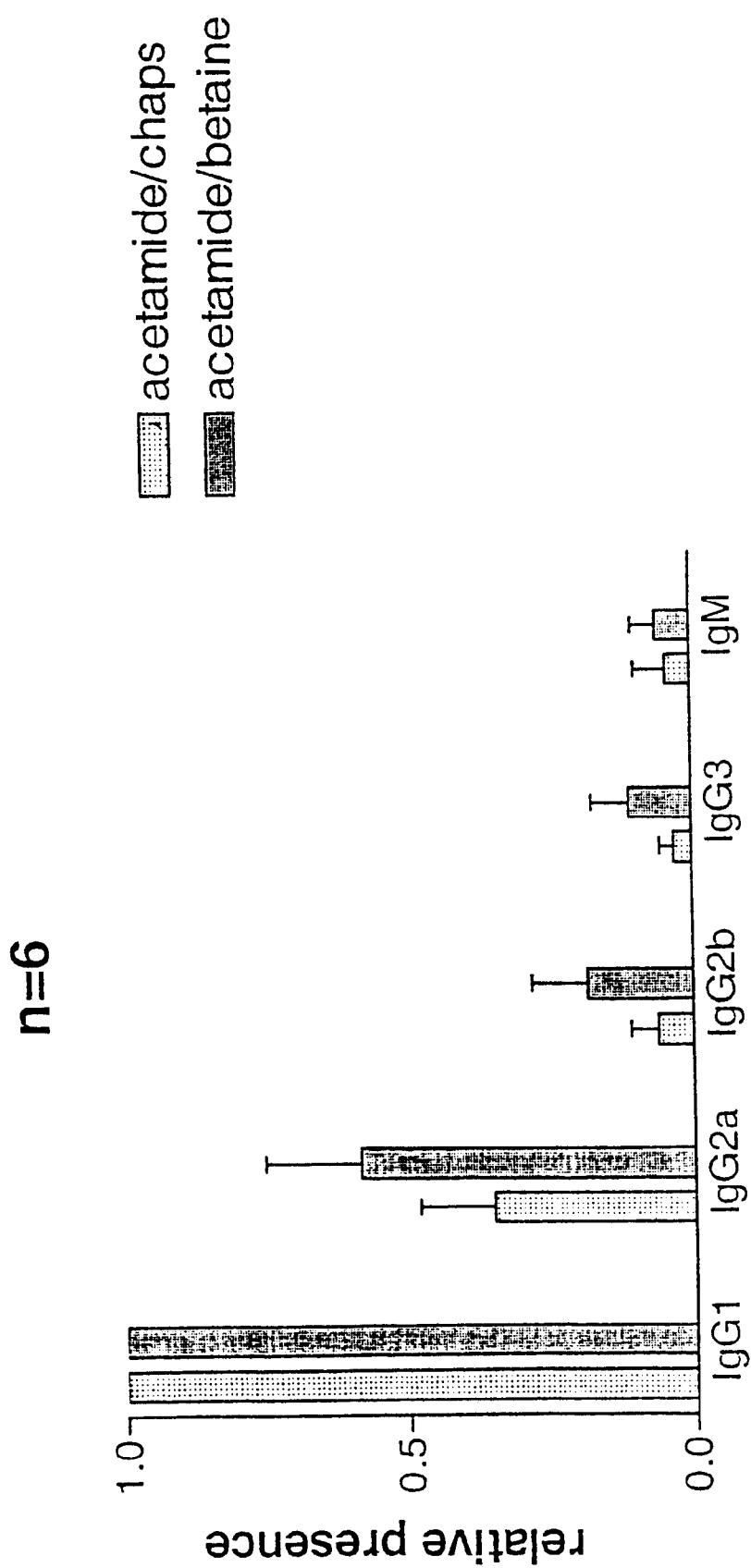

FIG. 19 Immunoglobulin isotyping profile of mice immunized with different E1s preparations. Specific Ig class and subclass antibodies were adsorbed at the microtiterplate. After capturing of the murine Ig out of immune sera diluted 1/500, E1s was incubated at 1 $\mu$g/ml. The formed immunecomplexes were further incubated with a polyclonal rabbit antiserum directed against E1. Finally, the rabbit antibodies were detected using a goat-anti-rabbit Ig secondary antiserum conjugated with peroxidase. TMB was used as substrate for color development. The results were normalized for $IgG_1$ (ie the $IgG_1$ signal was for each animal separately considered to be 1 and all the results for the other isotypes were expressed relative to this $IgG_1$ result).

Figure 20:
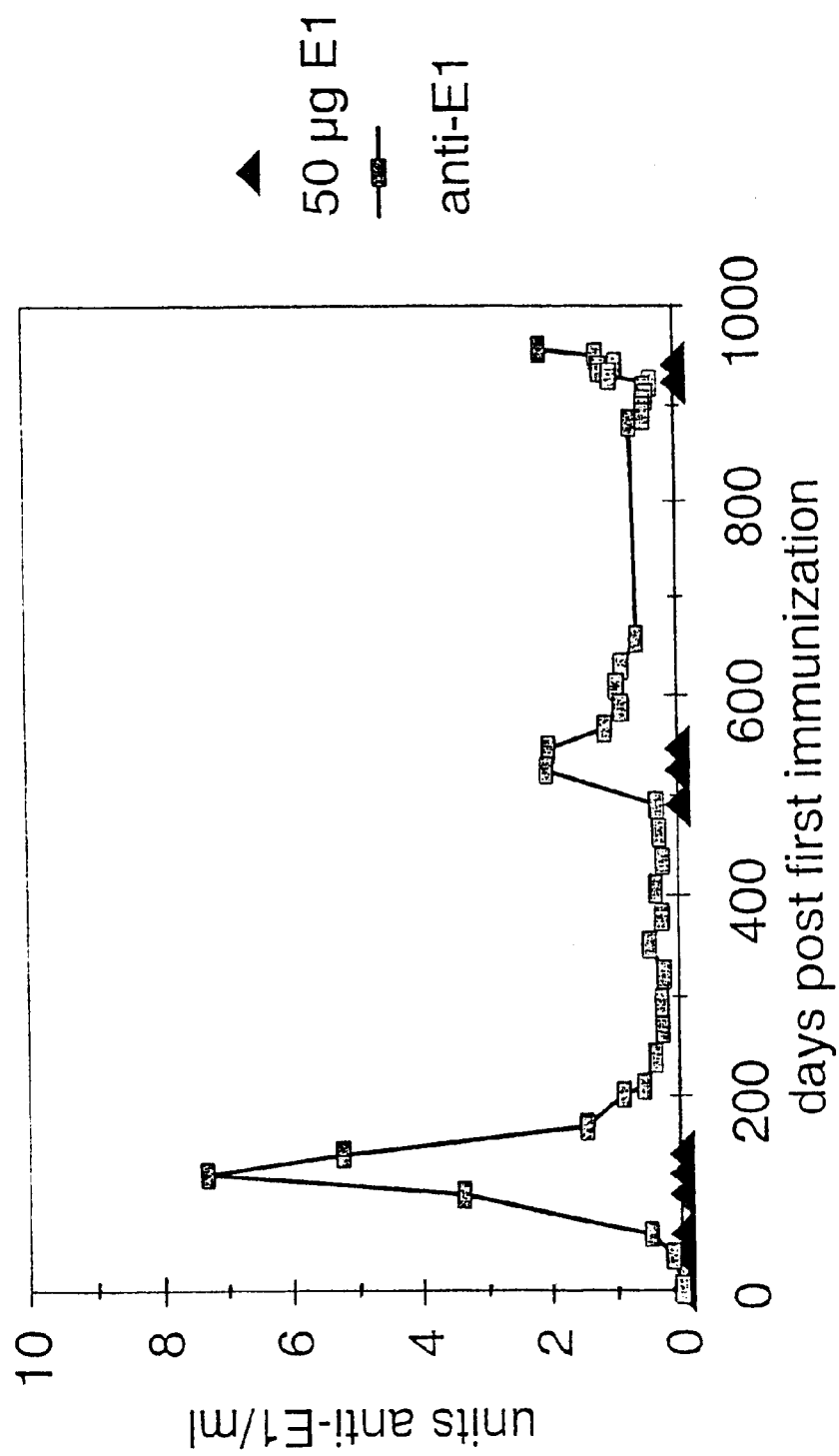

FIG. 20 Antibody titers induced by two immunizations around day 1000 with E1s-acetamide in chimp Phil. Anti-E1 antibodies were determined by means of an indirect ELISA: specific antibodies binding to solid phase E1 are detected using anti-human IgG specific secondary antiserum conjugated with peroxidase. The titer is expressed in units/ml, these units refer to an in house standard which is based on human sera.

Figure 21:
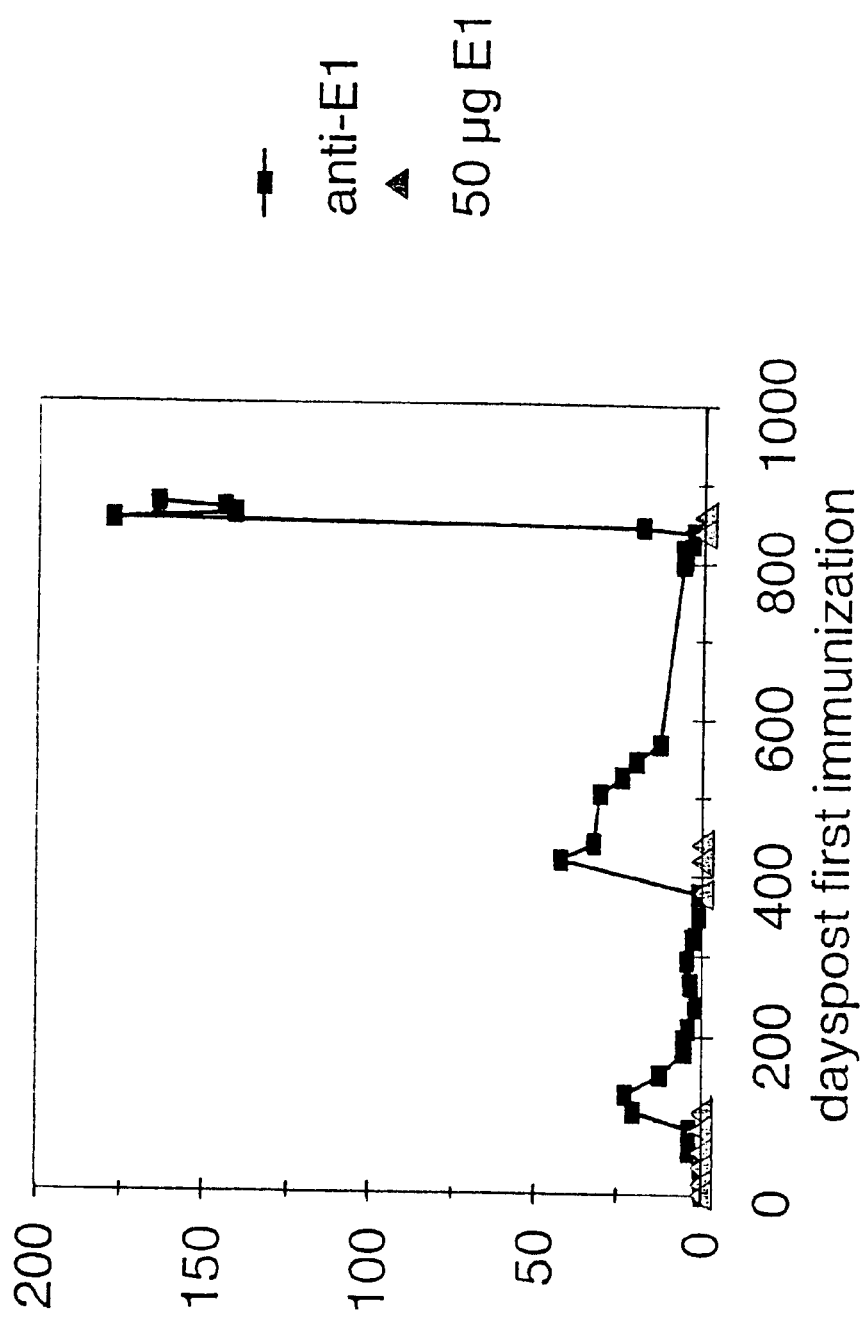

FIG. 21 Antibody titers induced by two immunizations around day 900 with E1s-acetamide in chimp Ton. Anti-E1 antibodies were determined by means of an indirect ELISA: specific antibodies binding to solid phase E1 are detected using anti-human IgG specific secondary antiserum conjugated with peroxidase. The titer is expressed in units/ml, these units refer to an in house standard which is based on human sera.

Figure 22A:
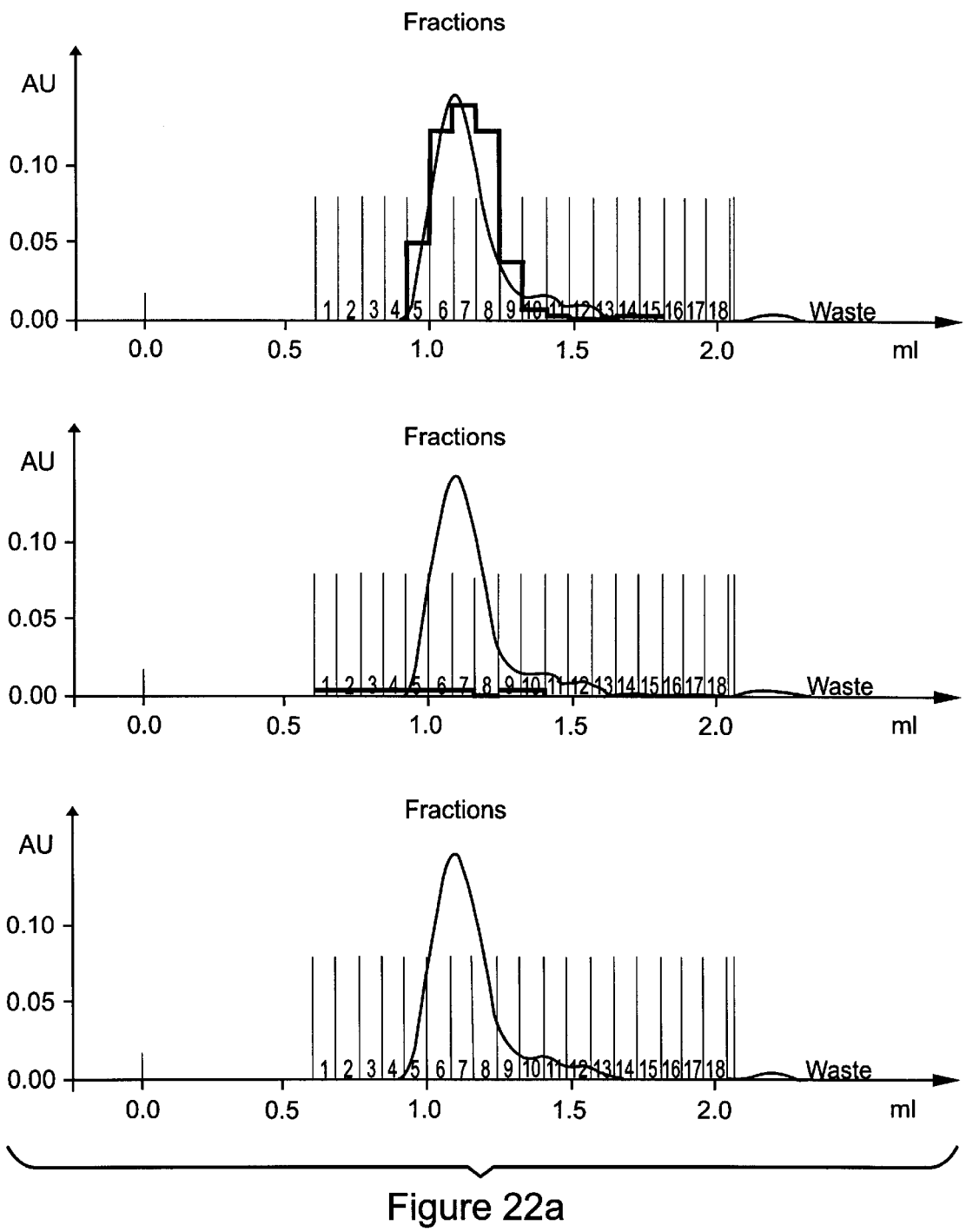
Figure 22B:
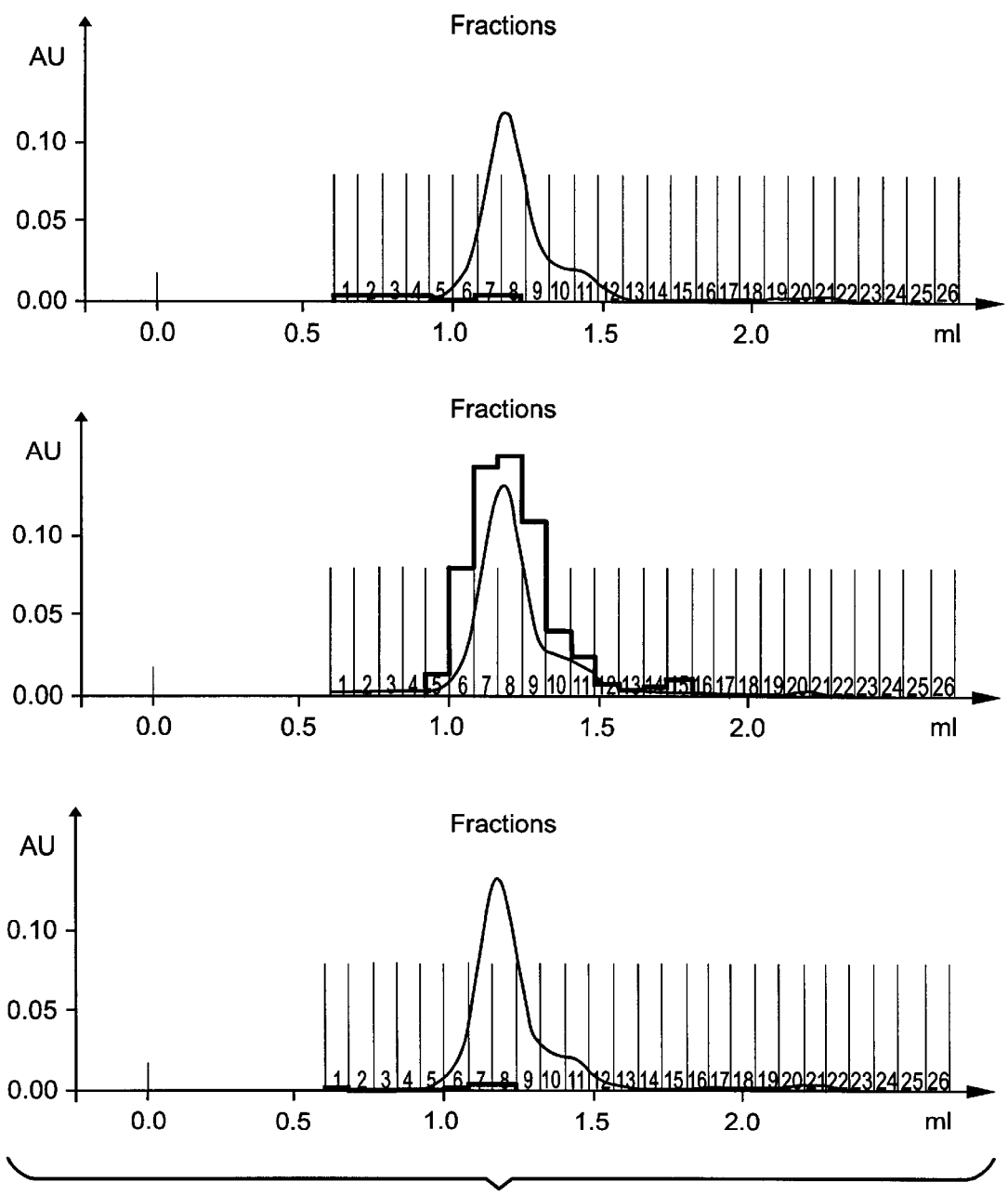
Figure 22C:
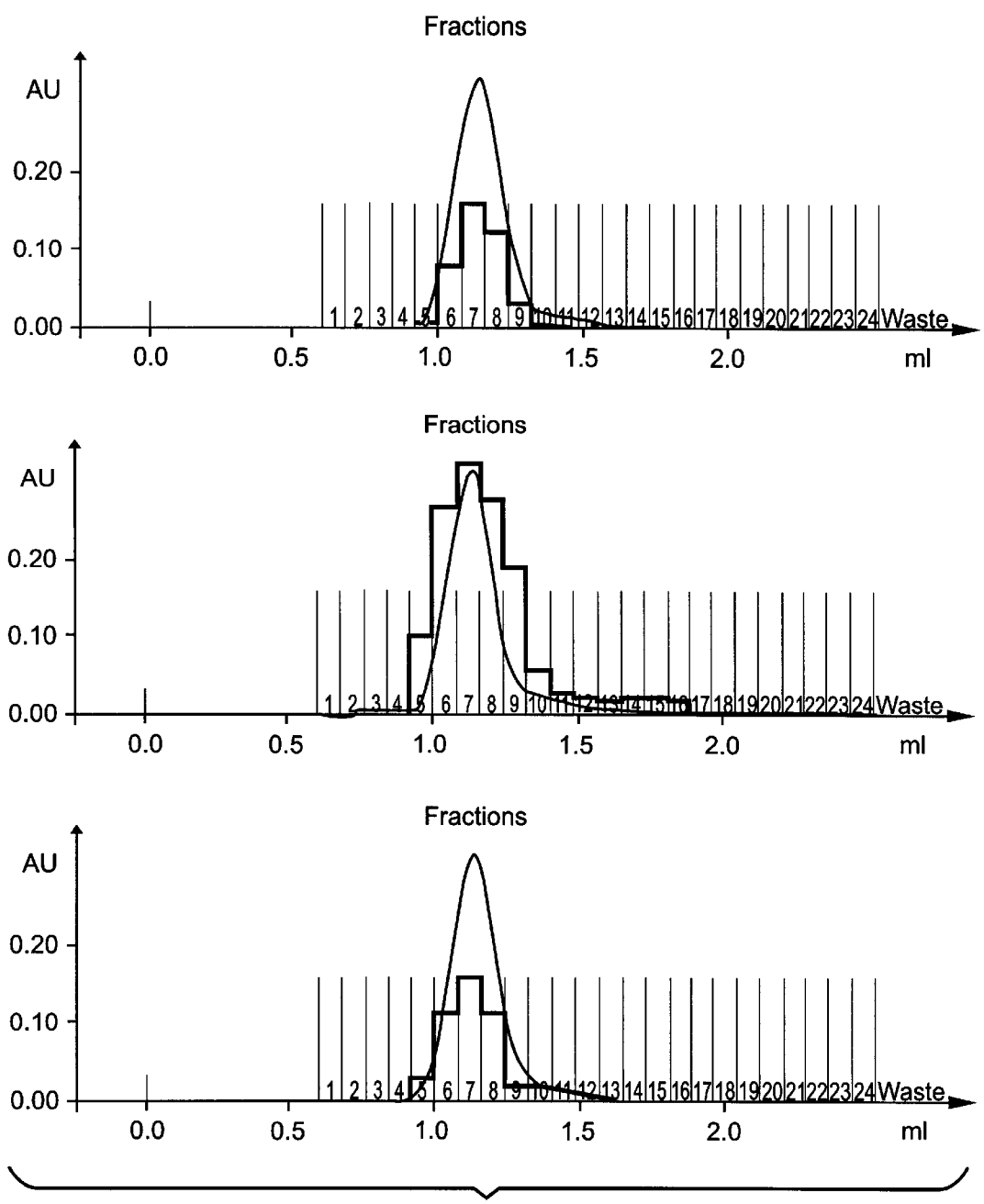

FIG. 22 SEC profile of the final detergent reduction step (0.2 to 0.05% CHAPS): E1 alone particle (A), E2 alone particle (B) or an equimolar mixture of E1 and E2; mixed particle (C). The figure also shows an overlay of the OD values of an ELISA specifically detecting E1 only (top), E2 only (middle) and an ELISA detecting only mixed particles (bottom).

Figure 23:
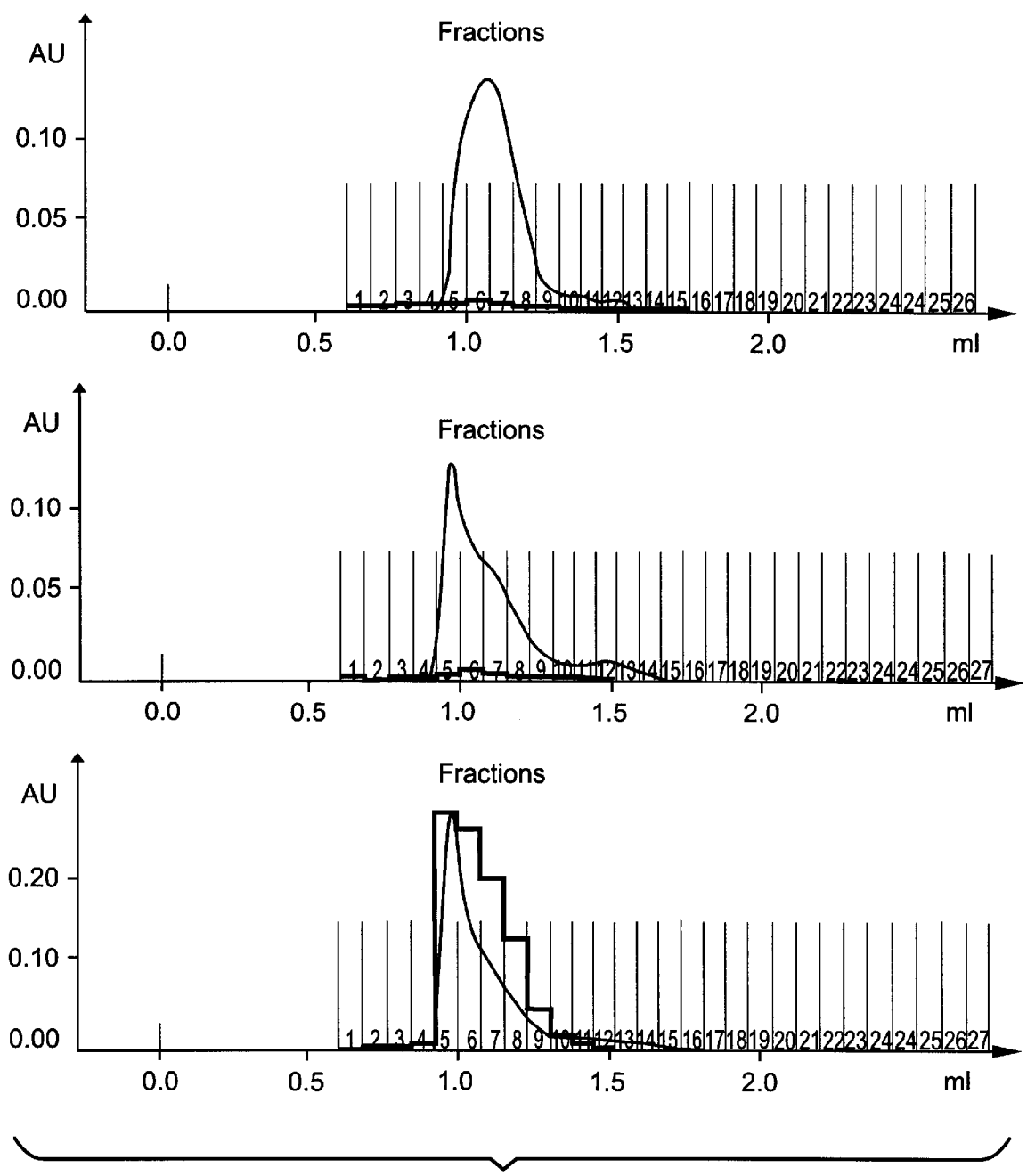

FIG. 23 SEC profile of the final detergent reduction step (0.2 to 0.05% CHAPS): E1 genotype 1b alone particle (top), E1 genotype 4 alone particle (middle) or an equimolar mixture of E1 genotype 1b and 4, mixed particle (bottom). The figure also shows an overlay of the OD values of an ELISA specifically detecting only mixed particles (see also FIG. 22).

DETAILED DESCRIPTION OF THE INVENTION

The invention described herein draws on previously published work and pending patent applications. By way of example, such work consists of scientific papers, patents or pending patent applications. All these publications and applications, cited previously or below are hereby incorporated by reference.

The present invention relates to HCV vaccination. For the first time successful immunotherapy of chimpanzees with severe chronic active hepatitis C could be achieved by vaccination with an HCV antigen. The vaccine not only induced high immune responses, but also induced clearance of viral antigen from the liver, and considerable improvement of the histological activity and of liver disease. The present invention further relates to purified single HCV envelope proteins and in particular to oligomeric particles. The oligomeric particles consist essentially of HCV envelope proteins and have a diameter of 1 to 100 nm as measured by dynamic light scattering or possibly electron microscopy. In this regard it should be stressed that the particles can be formed by E1 and/or E2 proteins only, or parts thereof (see infra). Therefore, the oligomeric particles of the present invention differ fundamentally with the HCV-like particles described in WO 98/21338, which necessarily consist of E1 and E2 and Core and P7. The terms "oligomeric particles consisting essentially of HCV envelope proteins" are herein defined as structures of a specific nature and shape containing several basic units of the HCV E1 and/or E2 envelope proteins, which on their own are thought to consist of one or two E1 and/or E2 monomers, respectively. It should be clear that the particles of the present invention are defined to be devoid of infectious HCV RNA genomes. The particles of the present invention can be higher-order particles of spherical nature which can be empty, consisting of a shell of envelope proteins in which lipids, detergents, the HCV core protein, or adjuvant molecules can be incorporated. The latter particles can also be encapsulated by liposomes or apolipoproteins, such as, for example, apolipoprotein B or low density lipoproteins, or by any other means of targeting said particles to a specific organ or tissue. In this case, such empty spherical particles are often referred to as "viral-like particles" or VLPs. Alternatively, the higher-order particles can be solid spherical structures, in which the complete sphere consists of HCV E1 or E2 envelope protein oligomers, in which lipids, detergents, the HCV core protein, or adjuvant molecules can be additionally incorporated, or which in turn may be themselves encapsulated by liposomes or apolipoproteins, such as, for example, apolipoprotein B, low density lipoproteins, or by any other means of targeting said particles to a specific organ or tissue, e.g. asialoglycoproteins. The particles can also consist of smaller structures (compared to the empty or solid spherical structures indicated above) which are usually round (see further)-shaped and which usually do not contain more than a single layer of HCV envelope proteins. A typical example of such smaller particles are rosette-like structures which consist of a lower number of HCV envelope proteins, usually between 4 and 16. A specific example of the latter includes the smaller particles obtained with E1s in 0.2% CHAPS as exemplified herein which apparently contain 8–10 monomers of E1s. Such rosette-like structures are usually organized in a plane and are round-shaped, e.g. in the form of a wheel. Again lipids, detergents, the HCV core protein, or adjuvant molecules can be additionally incorporated, or the smaller particles may be encapsulated by liposomes or apolipoproteins, such as, for example, apolipoprotein B or low density lipoproteins, or by any other means of targeting said particles to a specific organ or tissue. Smaller particles may also form small spherical or globular structures consisting of a similar smaller number of HCV E1 or E2 envelope proteins in which lipids, detergents, the HCV core protein, or adjuvant molecules could be additionally incorporated, or which in turn may be encapsulated by liposomes or apolipoproteins, such as, for example, apolipoprotein B or low density lipoproteins, or by any other means of targeting said particles to a specific organ or tissue. The size (i.e. the diameter) of the above-defined particles, as measured by the well-known-in-the-art dynamic light scattering techniques (see further in examples section), is usually between 1 to 100 nm, more preferentially between 2 to 70 nm, even more preferentially between 2 and 40 nm, between 3 to 20 nm, between 5 to 16 nm, between 7 to 14 nm or between 8 to 12 nm.

The invention further relates to an oligomeric particle as defined above, wherein said envelope proteins are selected from the group consisting of HCV E1, HCV E1s, HCV E2 proteins, SEQ ID No 13 or SEQ ID No 14, or parts thereof. The proteins HCV E1 and HCV E2, and a detailed description of how to purify the latter proteins, are well-described and characterized in PCT/EP 95/03031 to Maertens et al. HCV E1s, SEQ ID No 13 or SEQ ID No 14, or parts thereof, can be purified similarly as described for HCV E1 or HCV E1s in PCT/EP 95/03031 to Maertens et al.

It should be stressed that the whole content, including all the definitions, of the latter document is incorporated by reference in the present application. The protein HCV E1s refers to amino acids 192 to 326 of E1, and represents the E1 protein without its C-terminal hydrophobic anchor. The term "or parts thereof" refers to any part of the herein-indicated proteins which are immunogenic, once they are part of a particle of the present invention.

The invention further pertains to oligomeric particles as described herein, wherein at least one cysteine residue of the HCV envelope protein as described above is alkylated, preferably alkylated by means of alkylating agents, such as, for example, active halogens, ethylenimine or N-(iodoethyl)trifluoroacetamide. In this respect, it is to be understood that alkylation of cysteines refers to cysteines on which the hydrogen on the sulphur atom is replaced by $(CH_2)_nR$, in which n is 0, 1, 2, 3 or 4 and R=H, COOH, $NH_2$, $CONH_2$, phenyl, or any derivative thereof. Alkylation can be performed by any method known in the art, such as, for example, active halogens $X(CH_2)_nR$ in which X is a halogen such as I, Br, Cl or F. Examples of active halogens are methyliodide, iodoacetic acid, iodoacetamide, and 2-bromoethylamine. Other methods of alkylation include the use of ethylenimine or N-(iodoethyl)trifluoroacetamide both resulting in substitution of H by $—CH_2—CH_2—NH_2$ (Hermanson, 1996). The term "alkylating agents" as used herein refers to compounds which are able to perform alkylation as described herein. Such alkylations finally result in a modified cysteine, which can mimic other aminoacids. Alkylation by an ethylenimine results in a structure resembling lysine, in such a way that new cleavage sites for trypsine are introduced (Hermanson 1996). Similarly, the usage of methyliodide results in an amino acid resembling methionine, while the usage of iodoacetate and iodoacetamide results in amino acids resembling glutamic acid and glutamine, respectively. In analogy, these amino acids are preferably used in direct mutation of cysteine. Therefore, the present invention pertains to oligomeric particles as described herein, wherein at least one cysteine residue of the HCV envelope protein as described herein is mutated to a natural amino acid, preferentially to methionine, glutamic acid, glutamine or lysine. The term "mutated" refers to site-directed mutagenesis of nucleic acids encoding these amino acids, ie to the well kown methods in the art, such as, for example, site-directed mutagenesis by means of PCR or via oligonucleotide-mediated mutagenesis as described in Sambrook et al. (1989).

The term "purified" as applied herein refers to a composition wherein the desired components, such as, for example, HCV envelope proteins or oligomeric particles, comprises at least 35% of the total components in the composition. The desired components preferably comprises at least about 40%, more preferably at least about 50%, still more preferably at least about 60%, still more preferably at least about 70%, even more preferably at least about 80%, even more preferably at least about 90%, even more preferably at least about 95%, and most preferably at least about 98% of the total component fraction of the composition. The composition may contain other compounds, such as, for example, carbohydrates, salts, lipids, solvents, and the like, without affecting the determination of the percentage purity as used herein. An "isolated" HCV oligomeric particle intends an HCV oligomeric particle composition that is at least 35% pure. In this regard it should be clear that the term "a purified single HCV envelope protein" as used herein, refers to isolated HCV envelope proteins in essentially pure form. The terms "essentially purified oligomeric particles" and "single HCV envelope proteins" as used herein refer to HCV oligomeric particles or single HCV envelope proteins such that they can be used for in vitro diagnostic methods and therapeutics. These HCV oligomeric particles are substanially free from cellular proteins, vector-derived proteins or other HCV viral components. Usually, these particles or proteins are purified to homogeneity (at least 80% pure, preferably 85%, more preferably 90%, more preferably 95%, more preferably 97%, more preferably 98%, more preferably 99%, even more preferably 99.5%, and most preferably the contaminating proteins should be undetectable by conventional methods such as SDS-PAGE and silver staining).

The present invention also relates to an oligomeric particle as defined above wherein said envelope proteins are any possible mixture of HCV E1, HCV E1s, HCV E2, SEQ ID No 13 and/or SEQ ID No 14, or parts thereof, such as, for example, a particle of the present invention can substantially consist of HCV E1- and HCV E2 proteins, HCV E1- and HCV E1s proteins, HCV E1s - and HCV E2 proteins, and HCV E1-, HCV E1s- and HCV E2 proteins. Furthermore, the present invention also relates to an oligomeric particle as defined above wherein said proteins are derived from different HCV strains, subtypes or genotypes, such as, for example, said proteins are derived from genotype 1b and genotype 4, or are a mixture consisting of HCV envelope proteins from one strain or genotype of HCV and at least one other strain or genotype of HCV. The different HCV strains or genotypes are well-defined and characterized in PCT/EP 95/04155 to Maertens et al. It is stressed again that the whole content, including all the definitions, of the latter document is incorporated by reference in the present application. Thus, the present invention relates to oligomeric particles comprising envelope proteins derived from any HCV strain or genotype known in the art or to particles comprising a mixture of proteins derived from any HCV strain or genotype known in the art. In this regard the present invention also relates to a consensus sequences derived from individual clones as exemplified below and in the examples section (see further).

The present invention further relates to an oligomeric particle as described herein obtainable by a method, as well as to said method to produce said oligomeric particle. Said method is characterized by the following steps:

(I) Purifying HCV envelope proteins, possibly including the use of an optionally first detergent. In essence, the purification procedure of step (I) has been described extensively in PCT EP 95/03031 to Maertens et al. Importantly, according to the present invention, the blocking step in the purification procedure as described in PCT EP 95/03031, eg with NEM-biotin, is carried out with an alkylation step as described in the present application, preferentially by using iodoacetamide. Moreover, the purification procedure of step (I) can possibly include the use of a disulphide bond cleavage agent, and possibly include the use of an alkylating agent. Finally, the procedure of step (I) results in purified HCV envelope proteins in a solution.

(II) Replacing the solution of said purified HCV envelope proteins with a detergent or salt, resulting in the formation of oligomeric particles.

(III) Recovering or purifying said oligomeric particles, possibly including further reducing the concentration of the detergent or salt of step (II), which further assists the formation and stabilization of said oligomeric particles, formed after said replacing.

More preferably, the present invention relates to an oligomeric particle as defined herein, as well as the method to produce said particle, wherein said optionally first detergent is Empigen-BB. More preferably, the present invention relates to an oligomeric particle as defined herein, as well as the method to produce said particle, wherein the detergent of step (II) is CHAPS, octylglucaside or Tween, more preferably Tween-20 or Tween-80, or any other detergent. More preferably, the present invention relates to an oligomeric particle as defined herein, as well as the method to produce said particle, wherein said salt is betaine. Even more preferably, the present invention relates to an oligomeric particle as defined above, as well as the method to produce said particle, wherein said Empigen-BB is used at a concentration of 1% to 10% and wherein said CHAPS or Tween is used at a concentration of 0.01% to 10%, or said betaine is used at a concentration of 0.01% to 10%. Even more preferably, the present invention relates to an oligomeric particle as defined above, as well as the method to produce said particle, wherein said Empigen-BB is used at a concentration of 3% and wherein said CHAPS or betaine are used at concentrations of 0.2% or 0.3%, respectively, after which buffer is switched and said CHAPS or betaine are used at concentrations of 0.05% or 0.1–0.5%, respectively. It is to be understood that all percentages used in the method described above are given as weight/volume. It should be clear that the method described above (see also PCT/EP 95/03031 and the examples section of the present application) is an example of how to produce the particles of the present invention. In this regard, the present invention also concerns any other method known in the art which can be used to produce the oligomeric particles of the present invention, such as, for example, omitting the reducing agent as described in PCT/EP 95/03031 and the examples section (infra), and using instead host cells, which have an optimised redox state in the Endoplasmic Reticulum for reducing cysteine bridges. In addition, it should be clear that a whole range of alkylbetaines can be used, such as, for example, with a $C_n$ tail, in which n=a positive integer ranging from 1 to 20, as well as betaine derivatives, such as, for example, sulfobetaines.

Since for the first time successful immunotherapy of chimpanzees with severe chronic active hepatitis C was achieved by vaccination with a purified HCV antigen, the present invention also relates to purified single HCV envelope proteins, in particular E1 or E1s. Moreover, the present invention pertains to a composition comprising said single HCV envelope proteins, and the use thereof as an HCV vaccine, or for the manufacture of an HCV vaccine.

In order to avoid induction of an immune response against irrelevant epitopes, the HCV envelope protein used for vaccination is preferably constructed as a consensus sequence of individual subtypes, strains, or clones. Therefore, the present invention also pertains to the use of an HCV antigen (either in the form of peptide, protein, or a polynucleotide) for vaccination or diagnosis. Furthermore, the present invention also pertains to an oligomeric particle, as defined herein, and the use thereof, in which the HCV envelope protein is encoded by a consensus sequences based on quasispecies variability within an isolate (isolate consensus sequence) or based on the consensus sequence of different isolates within a subtype (subtype consensus sequence), type or species (type or species consensus sequence), or the complete HCV genus (genus consensus sequence). Consequently, the amino acid sequence of this consensus HCV envelope protein is a consensus sequence derived from an isolate-, subtype-, species-, or genus consensus amino acid sequence. For the connotation of the term "consensus" is particularly referred to Maertens and Stuyver (1997), and references used therein.

The oligomeric particle of the present invention displays epitopes extremely efficiently (see infra). Hence, the oligomeric particle is a means to present epitopes in such a way that they can elicit a proficient immune response. In this context, it is comprehended that the HCV envelope proteins as defined herein do not need to contain HCV epitopes exclusively. The HCV envelope proteins, which form the oligomeric particles, may contain epitopes that are derived from HCV solely, and possibly contain epitopes that are derived from other exogenous agents, such as, for example, HBV or HIV. In other words, the oligomeric particle with an HCV envelope protein backbone, can be used as a vehicle to present non-HCV epitopes, possibly in addition to HCV epitopes. Therefore, the present invention also encompasses an oligomeric particle, as defined herein but possibly without HCV epitopes, and its applications and its manufacture, possibly containing non-HCV epitopes. The term "exogenous agent" as used herein, refers to any agent, whether living or not, able to elicit an immune response, and which is not endogenous to the host, and which is not HCV. Specifically, the latter term refers to the group consisting of pathogenic agents, allergens and haptens. Pathogenic agents comprise prions, virus, prokaryotes and eukaryotes. More specifically, virus comprise in particular HBV, HIV, or Herpesvirus, but not HCV. Allergens comprise substances or molecules able to provoke an immune response in an host on their own when a host is exposed to said allergens. Haptens behave similarly to allergens with respect to the ability of provoking an immune response, but in contrast to allergens, haptens need a carrier molecule.

The present invention also relates to a composition comprising an oligomeric particle as defined above. More particularly the present invention relates to a vaccine composition. The term "vaccine composition" relates to an immunogenic composition capable of eliciting protection against HCV, whether partial or complete. It therefore includes HCV peptides, proteins, or polynucleotides. Protection against HCV refers in particular to humans, but refers also to non-human primates, trimera mouse (Zauberman et al., 1999), or other mammals.

The particles of the present invention can be used as such, in a biotinylated form (as explained in WO 93/18054) and/or complexed to *Neutralite Avidin* (Molecular Probes Inc., Eugene, Oreg., USA). It should also be noted that "a vaccine composition" comprises, in addition to an active substance, a suitable excipient, diluent, carrier and/or adjuvant which, by themselves, do not induce the production of antibodies harmful to the individual receiving the composition nor do they elicit protection. Suitable carriers are typically large slowly metabolized macromolecules such as proteins, polysaccharides, polylactic acids, polyglycolic acids, polymeric aa's, aa copolymers and inactive virus particles. Such carriers are well known to those skilled in the art. Preferred adjuvants to enhance effectiveness of the composition include, but are not limited to: aluminium hydroxide, aluminium in combination with 3-O-deacylated monophosphoryl lipid A as described in WO 93/19780, aluminium phosphate as described in WO 93/24148, N-acetyl-muramyl-L-threonyl-D-isoglutamine as described in U.S. Pat. No. 4,606,918, N-acetyl-normuramyl-L-alanyl-D-isoglutamine, N-acetylmuramyl-L-alanyl-D-isoglutamyl-L-alanine2-(1'2'dipalmitoyl-sn-glycero-3-hydroxyphosphoryloxy) ethylamine and RIBI (ImmunoChem Research Inc., Hamilton, Mont., USA) which contains monophosphoryl lipid A, detoxified endotoxin, trehalose-6,6-dimycolate, and cell wall skeleton (ML+TDM+CWS) in a 2% squalene/Tween 80 emulsion. Any of the three components MPL, TDM or CWS may also be used alone or combined 2 by 2. Additionally, adjuvants such as Stimulon (Cambridge Bioscience, Worcester, Mass., USA) or SAF-1 (Syntex) may be used, as well as adjuvants such as combinations between QS21 and 3-de-O-acetylated monophosphoryl lipid A (WO94/00153), or MF-59 (Chiron), or poly[di (carboxylatophenoxy) phosphazene]based adjuvants (Virus Research Institute), or blockcopolymer based adjuvants such as Optivax (Vaxcel, Cythx) or inulin-based adjuvants, such as Algammulin and GammaInulin (Anutech), Incomplete Freund's Adjuvant (IFA) or Gerbu preparations (Gerbu Biotechnik). It is to be understood that Complete Freund's Adjuvant (CFA) may be used for non-human applications and research purposes as well. "A vaccine composition" will further contain excipients and diluents, which are inherently non-toxic and non-therapeutic, such as water, saline, glycerol, ethanol, wetting or emulsifying agents, pH buffering substances, preservatives, and the like. Typically, a vaccine composition is prepared as an injectable, either as a liquid solution or suspension. Solid forms, suitable for solution on, or suspension in, liquid vehicles prior to injection may also be prepared. The preparation may also be emulsified or encapsulated in liposomes for enhancing adjuvant effect. The polypeptides may also be incorporated into Immune Stimulating Complexes together with saponins, for example Quil A (ISCOMS). Vaccine compositions comprise an immunologically effective amount of the polypeptides of the present invention, as well as any other of the above-mentioned components. "Immunologically effective amount" means that the administration of that amount to an individual, either in a single dose or as part of a series, is effective for prevention or treatment. This amount varies depending upon the health and physical condition of the individual to be treated, the taxonomic group of the individual to be treated (e.g. human, non-human primate, primate, etc.), the capacity of the individual's immune system to mount an effective immune response, the degree of protection desired, the formulation of the vaccine, the treating doctor's assessment, the strain of the infecting HCV and other relevant factors. It is expected that the amount will fall in a relatively broad range that can be determined through routine trials. Usually, the amount will vary from 0.01 to 1000 μg/dose, more particularly from 0.1 to 100 μg/dose. The vaccine compositions are conventionally administered parenterally, typically by injection, for example, subcutaneously or intramuscularly. Additional formulations suitable for other methods of administration include oral formulations and suppositories. Dosage treatment may be a single dose schedule or a multiple dose schedule. The vaccine may be administered in conjunction with other immunoregulatory agents. Therefore, the instant invention pertains to the use of an oligomeric particle as defined herein for prophylactically inducing immunity against HCV. It should be noted that a vaccine may also be useful for treatment of an individual as pointed-out above, in which case it is called a "therapeutic vaccine".

The present invention also relates to a composition as defined above which also comprises HCV core, E1, E2, P7, NS2, NS3, NS4A, NS4B, NS5A and/or NS5B protein, or parts thereof. E1, E2, and/or E1E2 particles may, for example, be combined with T cell stimulating antigens, such as, for example, core, P7, NS3, NS4A, NS4B, NS5A and/or NS5B. In particular, the present invention relates to a composition as defined above wherein said NS3 protein, or parts thereof, have an amino acid sequence given by SEQ ID 1 or SEQ ID 2(see further in examples section).

The purification of these NS3 proteins will preferentially include a reversible modification of the cysteine residues, and even more preferentially sulfonation of cysteines. Methods to obtain such a reversible modification, including sulfonation have been described for NS3 proteins in Maertens et al. (PCT/EP99/02547). It should be stressed that the whole content, including all the definitions, of the latter document is incorporated by reference in the present application.

It is clear from the above that the present invention also relates to the usage of an oligomeric particle as defined above or a composition as defined above for the manufacture of an HCV vaccine composition. In particular, the present invention relates to the usage of an oligomeric particle as defined herein for inducing immunity against HCV in chronic HCV carriers. More in particular, the present invention relates to the usage of an oligomeric particle as defined herein for inducing immunity against HCV in chronic HCV carriers prior to, simultaneously to or after any other therapy, such as, for example, the well-known interferon therapy either or not in combination with the administration of small drugs treating HCV, such as, for example, ribavirin. Such composition may also be employed before or after liver transplantation, or after presumed infection, such as, for example, needle-stick injury. In addition, the present invention relates to a kit containing the oligomeric particles or the single HCV envelope proteins of the present invention to detect HCV antibodies present in a biological sample. The term "biological sample" as used herein, refers to a sample of tissue or fluid isolated from an individual, including but not limited to, for example, serum, plasma, lymph fluid, the external sections of the skin, respiratory intestinal, and genitourinary tracts, oocytes, tears, saliva, milk, blood cells, tumors, organs, gastric secretions, mucus, spinal cord fluid, external secretions such as, for example, excrement, urine, sperm, and the like. Since the oligomeric particles and the single HCV envelope proteins of the present invention are highly immunogenic, and stimulate both the humoral and cellular immune response, the present invention relates also to a kit for detecting HCV related T cell response, comprising the oligomeric particle or the purified single HCV envelope protein of the instant invention. HCV T cell response can for example be measured as described in the examples section, or as described in PCT/EP 94/03555 to Leroux-Roels et al. It should be stressed that the whole content, including all the definitions, of this document is incorporated by reference in the present application.

It should be clear that the present invention also pertains to the use of specific HCV immunoglobulins for treatment and prevention of HCV infection. It is here for the first time demonstrated that sufficient levels of HCV antibodies, especially HCV envelope antibodies, induce amelioration of Hepatitis C disease. It is also demonstrated for the first time that sufficient levels of antibodies can bind circulating virus, and that the presence of Ab-complexed virus coincides with disappearance of HCV antigen from the liver, and with amelioration of liver disease. HCV envelope antibodies may be induced by vaccination or may be passively transferred by injection after the antibodies have been purified from pools of HCV-infected blood or from blood obtained from HCV vaccinees. Therefore, the present invention pertains further to specific antibodies, generated against an oligomeric particle as described above or against a composition as described above, or a single HCV envelope protein. In particular, the present invention relates to a kit comprising said antibodies for detecting HCV antigens. The term "specific antibodies" as used herein, refers to antibodies, which are raised against epitopes which are specific to the oligomeric particle as disclosed in the present invention. In other words, specific antibodies are raised against epitopes which result from the formation of, and are only present on oligomeric particles. Moreover, there are various procedures known to produce HCV peptides. These procedures might result in HCV peptides capable of presenting epitopes. It is conceivable that the HCV peptides, obtained by these various and different procedures, are capable of presenting similar epitopes. Similar epitopes are epitopes resulting from different production or purifying procedures but recognizable by one and the same antibody. However, the oligomeric particles of the instant invention present epitopes extremely efficient. Consequently, the epitopes on the oligomeric particles are highly immunogenic. Therefore, the present invention also pertains to epitopes on oligomeric particles, said epitopes are at least 10 times, preferentially at least 20 times, preferentially at least 50, preferentially at least 100 times, preferentially at least 500 times, and most preferentially at least 1000 times more immunogenic than epitopes on HCV-peptides, which are not produced according to the present invention, ie not produced by detergent-assisted particle formation. It will be appreciated by the skilled that said immunogenecity can, for example, be detected and therefore compared by immunising mammals by means of administering comparable quantities of peptides, produced by either method. Moreover, the term "specific antibody" refers also to antibodies which are raised against a purified single HCV envelope protein. As used herein, the term "antibody" refers to polyclonal or monoclonal antibodies. The term "monoclonal antibody" refers to an antibody composition having a homogeneous antibody population. The term "antibody" is not limiting regarding the species or source of the antibody, nor is it intended to be limited by the manner in which it is made. In addition, the term "antibody" also refers to humanized antibodies in which at least a portion of the framework regions of an immunoglobulin are derived from human immunoglobulin sequences and single chain antibodies, such as, for example, as described in U.S. Pat. No 4,946,778, to fragments of antibodies such as $F_{ab}$, $F_{(ab)2}$, $F_v$, and other fragments which retain the antigen binding function and specificity of the parental antibody.

Moreover, the present invention also features the use of an oligomeric particle as described above, or a composition as described above to detect antibodies against HCV envelope proteins. As used herein, the term "to detect" refers to any assay known in the art suitable for detection. In particular, the term refers to any immunoassay as described in WO 96/13590.

The terms "peptide", "polypeptide" and "protein" are used interchangeably in the present invention. "Polypeptide" refers to a polymer of amino acids (amino acid sequence) and does not refer to a specific length of the molecule. Thus, oligopeptides are included within the definition of polypeptide. It is to be understood that peptidomimics are inherent in the terms "polypeptide", "peptide" and "protein".

Also, the present invention relates to the use of an oligomeric particle as described herein for inducing immunity against HCV, characterized in that said oligomeric particle is used as part of a series of time and compounds. In this regard, it is to be understood that the term "a series of time and compounds" refers to administering with time intervals to an individual the compounds used for eliciting an immune response. The latter compounds may comprise any of the following components: oligomeric particles, HCV DNA vaccine composition, HCV polypeptides.

In this respect, a series comprises administering, either:

(I) an HCV antigen, such as, for example, an oligomeric particle, with time intervals, or (II) an HCV antigen, such as, for example, an oligomeric particle in combination with a HCV DNA vaccine composition, in which said oligomeric particles and said HCV DNA vaccine composition, can be administered simultaneously, or at different time intervals, including at alternating time intervals, or (III) either (I) or (II), possibly in combination with other HCV peptides, with time intervals.

In this regard, it should be clear that a HCV DNA vaccine composition comprises nucleic acids encoding HCV envelope peptide, including E1-, E2-, E1/E2-peptides, E1s peptide, SEQ ID No 13, SEQ ID No 14, NS3 peptide, other HCV peptides, or parts of said peptides. Moreover, it is to be understood that said HCV peptides comprises HCV envelope peptides, including E1-, E2-, E1/E2-peptides, E1s peptide, SEQ ID No 13, SEQ ID No 14, NS3 peptide, other HCV peptides, or parts thereof. The term "other HCV peptides" refers to any HCV peptide or fragment thereof with the proviso that said HCV peptide is not E1, E2, E1s, SEQ ID No 13, SEQ ID No 14, or NS3. In item II of the above scheme, the HCV DNA vaccine composition comprises preferentially nucleic acids encoding HCV envelope peptides. In item II of the above scheme, the HCV DNA vaccine composition consists even more preferentially of nucleic acids encoding HCV envelope peptides, possibly in combination with a HCV-NS3 DNA vaccine composition. In this regard, it should be clear that an HCV DNA vaccine composition comprises a plasmid vector comprising a polynucleotide sequence encoding an HCV peptide as described above, operably linked to transcription regulatory elements. As used herein, a "plasmid vector" refers to a nucleic acid molecule capable of transporting another nucleic acid to which it has been linked. Preferred vectors are those capable of autonomous replication and/or expression of nucleic acids to which they have been linked. In general, but not limited to those, plasmid vectors are circular double stranded DNA loops which, in their vector form, are not bound to the chromosome. As used herein, a "polynucleotide sequence" refers to polynucleotides such as deoxyribonucleic acid (DNA), and, where appropriate, ribonucleic acid (RNA). The term should also be understood to include, as equivalents, analogs of either RNA or DNA made from nucleotide analogs, and single (sense or antisense) and double-stranded polynucleotides. As used herein, the term "transcription regulatory elements" refers to a nucleotide sequence which contains essential regulatory elements, such that upon introduction into a living vertebrate cell it is able to direct the cellular machinery to produce translation products encoded by the polynucleotide. The term "operably linked" refers to a juxtaposition wherein the components are configured so as to perform their usual function. Thus, transcription regulatory elements operably linked to a nucleotide sequence are capable of effecting the expression of said nucleotide sequence. Those skilled in the art can appreciate that different transcriptional promoters, terminators, carrier vectors or specific gene sequences may be used succesfully.

Finally, the present invention relates to an immunoassay for detecting HCV antibody, which immunoassay comprises: (1) providing the oligomeric particle or the purified single HCV envelope protein as defined herein, or a functional equivalent thereof, (2) incubating a biological sample with said oligomeric particle, or said HCV envelope protein under conditions that allow the formation of antibody-antigen complex, (3) determining whether said antibody-antigen complex comprising said oligomeric particle or said HCV envelope protein is formed.

The present invention will now be illustrated by reference to the following examples which set forth particularly advantageous embodiments. However, it should be noted that these embodiments are merely illustrative and can not be construed as to restrict the invention in any way.

EXAMPLES

Example 1

Expression, Purification, and Detergent-assisted Homo-oligomerization of the HCV E1 Protein The HCV E1s protein (amino acids 192–326) was expressed and purified from RK13 cells using recombinant vaccinia virus pvHCV-11A according to the protocol described in Maertens et al. (PCT/EP 95/03031). In addition, the purified E1 protein in 3% Empigen-BB which displays an apparent molecular weight corresponding to an E1 homodimer (approximately about 60 kDa; FIG. 1), was pooled and the pooled fractions were again applied to a size exclusion chromatography column (according to PCT/EP 95/03031) and run in the presence of 0.2% CHAPS or 3% betaine. Surprisingly, although the E1s protein is devoid of its membrane anchor region, a homogeneous population of specifically associated E1 homo-oligomers with an apparent molecular weight of 260–280 kDa could be obtained with both detergents (FIG. 2). Such a homo-oligomeric structure could contain an approximate number of 9 E1s monomers. It should be clear that the latter is a rough estimate as the shape of the oligomer may drastically influence its apparent molecular weight as measured by size exclusion chromatography. By switching from 0.2% CHAPS to 0.05% CHAPS and repeating the same procedure, the apparent molecular weight further shifted beyond the resolution of the column (void of the column, >600 kDa, FIG. 3), suggesting the formation of particles. Switching from 3% betaine to 0.1% betaine yielded a population of E1s oligomers with a similar behaviour (data not shown). Other detergents could be chosen by means of which similar detergent-assisted oligomerization could be achieved. The oligomerization leading to the particle formation is not unique for CHAPS or betaine, since similar results were obtained by using Tween-20 or Tween-80, or octylglucaside. Moreover, further removal of the detergent may be possible which may allow to generate even larger particles. The presence of detergent may, therefore, not longer be needed to obtain particles. The particles may be obtained by e.g. SCC, without any detergent. Notably, an E1 monomer is approximately 31 kDa, while an E2 monomer is approximately 70 kDa. These values, however, may differ depending on the glycosylation status of the protein.

Example 2

Analysis of the Higher Order Oligomeric Structures of E1s by Means of Dynamic Light Scattering In order to confirm the unexpected result that particles have been created, E1s preparations in 0.05% CHAPS and 0.1% betaine, prepared according to example 1, or in 0.1% betaine, prepared by dilution of preparations in 0.5% betaine, were subjected to analysis by means of dynamic light scattering (DLS).

The dynamic light scattering technique measures Brownian motion and relates this to the size of particles. The larger the particle, the slower the Brownian motion will be. The velocity of the Brownian motion is defined by a property known as the diffusion coefficient (usually given by the symbol D). The size of the particle is calculated from the diffusion coefficient by using the Stokes-Einstein equation: $d(H)=kT/3\pi\eta D$, in which d(H) is the hydrodynamic diameter, k is the Boltzmann constant, T is the absolute temperature, $\eta$ is the viscosity. Notebly, the measured diameter is a value which refers to how a particle diffuses within a fluid. So, it is referred to as hydrodynamic diameter. The diffusion coefficient is derived from an autocorrelation function (variation of intensity fluctuation of light with time). The instrument uses a computer-controlled correlator to calculate the intensity of the autocorrelation function automatically.

For measuring size distributions, the above autocorrelation function is corrected to obtain linear curves and the instrument is equipped with a computer program for analysis of the size distribution. However, the technique has restrictive assumptions similar to those of the technique called multi angle laser light scattering (MALLS) and neither method can be considered to yield absolute data. The results of size distributions from DLS have to be interpreted as semi-quantitative indicators of polydispersity, rather than as a true representation of the distribution.

Samples containing E1s particles (80–400 $\mu$g E1s/ml PBS-0.05% CHAPS, 0.1% or 0.5% betaine) were pipetted in the measuring cell of an LSP 3.53 DLS instrument equipped with a 10 mW HeNe Laser (PolymerLabs). A readout of the analysis is provided in FIGS. 4 (E1s in 0.05% CHAPS) and 5 (E1s in 0.1% or 0.5% betaine).

These analyses indeed confirmed the unexpected result that the obtained E1s structures were spherical, monodisperse particles. The E1s particles in PBS/0.1% betaine showed an average size distribution of 21.3±4 nm, in PBS/0.5% betaine: 27.9±5 nm, whereas a diameter of 12.5 was obtained for E1s in PBS/0.05% CHAPS.

Example 3

Size and Shape Analysis by Means of Electron Microscopy

Ten $\mu$l of E1s (226 $\mu$g/ml in PBS/0.05% CHAPS; and 143 $\mu$g/ml in PBS 3% betaine) was visualized with a standard negative staining with 1% uranyl acetate on carbon stabilized formvar grids. The sample was applied for 30 seconds and then rinsed with dH$_2$O before staining for 5 seconds and photography (FIG. 6).

Statistical analysis yielded the following results: the E1s particle in CHAPS had a mean diameter of 8.7±0.27 nm (range 4.3–29.0; 95% CI 5.4) and that the E1s particle in betaine was less homogeneous with a mean diameter of 9.7±0.55 nm (range 4.3–40.5; 95% CI 11.0). Surprisingly, the 3% betaine preparation, which initially showed a MW of 250–300 kDa as analysed by SEC even shows larger particles than the 0.05% CHAPS preparation, which initially showed a MW of >600 kDa. We therefore hypothesized that intermediate homo-oligomeric forms of E1s obtained by 3% betaine may have formed higher order particles over time. This surprising effect points to other possibilities for obtaining higher-order particles. A size distribution of the particles (FIG. 7) shows that the CHAPS preparation is monodisperse, although a tailing to larger size particles is observed (up to 29 nm for 0.05% CHAPS). Since larger structures are overestimated in DLS analyses, the presence of these larger particles, although less in number, may explain the larger diameter obtained by DLS analysis (example 2). The difference in diameter may also be explained by the fact that DLS measures a particle in motion, while electron microscopy measures static particles. It should be clear that the immunogenicity of these preparations as shown in the examples below is due to the entirety of the preparation, and may be due to the average, smaller, or larger particles, or to the mixture thereof.

Example 4

Immunization of a Chimpanzee Chronically Infected with HCV Subtype 1b

A chimpanzee (Phil) already infected for over 13 years (5015 days before immunization) with an HCV subtype 1b strain was vaccinated with E1 (aa 192–326) which was derived from a different strain of genotype 1b, with a 95.1% identity on the amino acid level (see also Table 2), and which was prepared as described in examples 1–3. The chimpanzee received in total 6 intramuscular immunizations of each 50 µg E1 in PBS/0.05% CHAPS mixed with RLBI R-730 (MPLA+TDM+CWS) according to the manufacturer's protocol (Ribi Inc. Hamilton, Mont.). The 6 immunizations were given in two series of three shots with a three week interval and with a lag period of 6 weeks between the two series. Starting 150 days prior to immunization, during the immunization period and until 1 year post immunization (but see below) the chimpanzee was continuously monitored for various parameters indicative for the activity of the HCV induced disease. These parameters included blood chemistry, ALT, AST, gammaGT, blood chemistry, viral load in the serum, viral load in the liver and liver histology. In addition, the immune answer to the immunization was monitored both on the humoral and cellular level. During this period the animal was also monitored for any adverse effects of the immunization, such as change in behaviour, clinical symptoms, body weight, temperature and local reactions (redness, swelling, indurations). Such effects were not detected.

Clearly, ALT (and especially gammaGT, data not shown) levels decreased as soon as the antibody level against E1 reached its maximum (FIG. 8). ALT rebounded rather rapidly as soon as the antibody levels started to decline, but gammaGT remained at a lower level as long as anti-E1 remained detectable.

E2 antigen in the liver decreased to almost undetectable levels during the period in which anti-E1 was detectable and the E2 antigen rebounded shortly after the disappearance of these antibodies. Together with the Core and E2 antigen becoming undetectable in the liver, the inflammation of the liver markedly decreased (see also Table 3). This is a major proof that the vaccine induces a reduction of the liver damage, probably by clearing, at least partially, the viral antigens from its major target organ, the liver.

The viraemia level, as measured by Amplicor HCV Monitor (Roche, Basel, Switzerland), remained approximately unchanged in the serum during the whole study period.

More detailed analyses of the humoral response revealed that the maximum end-point titer reached 14.5×10$^3$ (after the sixth immunization) and that this titer dropped to undetectable 1 year post immunization (FIG. 8). FIG. 9 shows that the main epitopes, which can be mimicked by peptides, recognized by the B-cells are located at the N-terminal region of E2 (peptides V1V2 and V2V3, for details on the peptides used see Table 4). Since the reactivity against the recombinant E1 is higher and longer lasting, it can also be deduced from this figure, that the antibodies recognizing these peptides represent only part of the total antibody population against E1. The remaining part is directed against epitopes which cannot be mimicked by peptides, i.e discontinuous epitopes. Such epitopes are only present on the complete E1 molecule or even only on the particle-like structure. Such an immune response against E1 is unique, at least compared to what is normally observed in human chronic HCV carriers (WO 96/13590 to Maertens et al.) and in chimpanzees (van Doorn et al., 1996), who raise anti-E1 antibodies in their natural course of infection. In those patients, anti-E1 is in part also directed to discontinuous epitopes but a large proportion is directed against the C4 epitope (±50% of the patient sera), a minor proportion against V1V2 (ranging from 2–70% depending on the genotype), and reactivity against V2V3 was only exceptionally recorded (Maertens et al., 1997).

Analysis of the T-cell reactivity indicated that also this compartment of the immune system is stimulated by the vaccine in a specific way, as the stimulation index of these T-cells rises from 1 to 2.5, and remains somewhat elevated during the follow up period (FIG. 10). It is this T cell reactivity that is only seen in Long term responders to interferon therapy (see: PCT/EP 94/03555 to Leroux-Roels et al.; Leroux-Roels et al., 1996).

Example 5

Immunization of a Chronic HCV Carrier with Different Subtype

A chimpanzee (Ton) already infected for over 10 years (3809 days before immunization) with HCV from genotype 1a was vaccinated with E1 from genotype 1b, with only a 79.3% identity on the amino acid level (see also Table 2), and prepared as described in the previous examples. The chimpanzee received a total of 6 intramuscular immunizations of 50 µg E1 in PBS/0.05% CHAPS each mixed with RIBI R-730 according to the manufacturer's protocol (Ribi Inc. Hamilton, Mont.). The 6 immunizations were given in two series of three shots with a three week interval and with a lag period of 4 weeks between the two series. Starting 250 days prior to immunization, during the immunization period and until 9 months (but see below) post immunization the chimpanzee was continuously monitored for various parameters indicative for the activity of the HCV induced disease. These parameters included blood chemistry, ALT, AST, gammaGT, viral load in the serum, viral load in the liver and liver histology. In addition, the immune answer to the immunization was monitored both on the humoral and cellular level. During this period the animal was also monitored for any adverse effects of the immunization, such as change in behaviour, clinical symptoms, body weight, temperature and local reactions (redness, swelling, indurations). Such effects were not detected.

Clearly, ALT levels (and gammaGT levels, data not shown) decreased as soon as the antibody level against E1 reached its maximum (FIG. 11). ALT and gammaGT rebounded as soon as the antibody levels started to decline, but ALT and gammaGT remained at a lower level during the complete follow up period. ALT levels were even significantly reduced after vaccination (62±6 U/l) as compared to the period before vaccination (85±11 U/l). Since less markers of tissue damage were recovered in the serum, these findings were a first indication that the vaccination induced an improvement of the liver disease.

E2 antigen levels became undetectable in the period in which anti-E1 remained above a titer of $1.0 \times 10^3$, but became detectable again at the time of lower E1 antibody levels. Together with the disappearance of HCV antigens, the inflammation of the liver markedly decreased from moderate chronic active hepatitis to minimal forms of chronic persistent hepatitis (Table 3). This is another major proof that the vaccine induces a reduction of the liver damage, probably by clearing, at least partially, the virus from its major target organ, the liver.

The viraemia level, as measured by Amplicor HCV Monitor (Roche, Basel, Switzerland), in the serum remained at approximately similar levels during the whole study period. More detailed analysis of the humoral response revealed that the maximum end-point titer reached was $30 \times 10^3$ (after the sixth immunization) and that this titer dropped to $0.5 \times 10^3$ nine months after immunization (FIG. 11). FIG. 12 shows that the main epitopes, which can be mimicked by peptides and are recognized by the B-cells, are located at the N-terminal region (peptides V1V2 and V2V3, for details on the peptides used see Table 4). Since the reactivity against the recombinant E1 is higher and longer lasting, it can also be deduced from this figure, that the antibodies recognizing these peptides represent only part of the total antibody population against E1. The remaining part is most likely directed against epitopes which cannot be mimicked by peptides, i.e. discontinuous epitopes. Such epitopes are probably only present on the complete E1 molecule or even only on the particle-like structure. Such an immune response against E1 is unique, at least compared to what is normally observed in human chronic HCV carriers, which have detectable anti-E1. In those patients, anti-E1 is in part also discontinuous, but a large proportion is directed against he C4 epitope (50% of the patient sera), a minor proportion against $V_1V2$ (ranging from 2–70% depending on the genotype) and exceptionally reactivity against V2V3 was recorded (Maertens et al., 1997). As this chimpanzee is infected with an 1a isolate the antibody response was also evaluated for cross-reactivity towards a E1-1a antigen. As can be seen in FIG. 13, such cross-reactive antibodies are indeed generated, although, they form only part of the total antibody population. Remarkable is the correlation between the reappearance of viral antigen in the liver and the disappearance of detectable anti-1a E1 antibodies in the serum.

Analysis of the T-cell reactivity indicated that also this compartment of the immune system is stimulated by the vaccine in a specific way, as the stimulation index of these T-cells rises from 0.5 to 5, and remains elevated during the follow up period (FIG. 14).

Example 6

Reboosting of HCV Chronic Carriers with E1

As the E1 antibody titers as observed in examples 4 and 5 were not stable and declined over time, even to undetectable levels for the 1b infected chimp, it was investigated if this antibody response could be increased again by additional boosting. Both chimpanzees were immunized again with three consecutive intramuscular immunization with a three week interval (50 µg E1 mixed with RIBI adjuvant). As can be judged from FIGS. 8 and 11, the anti-E1 response could indeed be boosted, once again the viral antigen in the liver decreased below detection limit. The viral load in the serum remained constant although in Ton (FIG. 11). A viremia level of $<10^5$ genome equivalents per ml was measured for the first time during the follow up period.

Notable is the finding that, as was already the case for the first series of immunizations, the chimpanzee infected with the subtype 1b HCV strain (Phil) responds with lower anti-E1 titers, than the chimpanzee infected with subtype 1a HCV strain (maximum titer in the first round $14.5 \times 10^3$ versus $30 \times 10^3$ for Ton and after additional boosting only $1.2 \times 10^3$ for Phil versus $40 \times 10^3$ for Ton). Although for both animals the beneficial effect seems to be similar, it could be concluded from this experiment that immunization of a chronic carrier with an E1 protein derived from another subtype or genotype may be especially beneficial to reach higher titers, maybe circumventing a preexisting and specific immune suppression existing in the host and induced by the infecting subtype or genotype. Alternatively, the lower titers observed in the homologous setting (1b vaccine+1b infection) may indicate binding of the bulk of the antibodies to virus. Therefore, the induced antibodies may possess neutralizing capacity.

Example 7a

Construction of a NS3 Protein Combining the Major Epitopes Known to Correlate with Control of Infection Also other epitopes besides the ones in E1 may be linked with clearing of HCV during acute phase or by interferon therapy. Several of these epitopes are localized within NS3 (Leroux-Roels et al., 1996; Rehermann et al., 1996 and 1997; Diepolder et al., 1995 and 1997). Two of the major epitopes are the CTL epitope mapped by Rehermann and coworkers (aa 1073–1081), and the T-cell (CD4) epitope mapped by Diepolder and coworkers (aa 1248–1261). Unfortunately, these epitopes are scattered all over the, NS3 protein. In order to have at least those epitopes available, a relatively large protein would be needed (aa 1073–1454). Producing such a large protein usually results in low yields, and may result upon vaccination in a response which is only for a small part targeted to the important epitopes. Therefore, production of a smaller protein would be a more suitable solution to this problem. In order to do so, some of the epitopes need to be repositioned within such a smaller protein. By taking advantage of the knowledge that exists, ie another CTL epitope (aa 1169–1177) which is not linked with HCV clearance (Rehermann et al. 1996, 1997), an NS3 molecule was designed to start at aa 1166 and to end at aa 1468 (Table 5). This construct already includes the epitopes described by Weiner and coworkers, and Diepolder and coworkers. By mutating the region 1167 to 1180 to the sequence of the region 1071 to 1084, the non-relevant CTL epitope was changed to the epitope Rehermann and coworkers found to be linked with viral clearance. The construct was additionally modified to contain a methionine at position 1166 to allow initiation of translation. This methionine will be cleaved off in *E. coli* since it is followed by an alanine. In this way, the introduction of new epitopes, which are not present in the natural NS3, is limited to a minimum. Alternatively, if the expression of this protein would be cumbersome, the CTL epitope may be linked to the C-terminus at aa 1468 as depicted in detail in Table 5.

The coding sequence of an HCV NS-3 fragment was isolated and expressed as described in Maertens et al. (PCT/EP99/02547; clone 19b; HCV aa 1188–1468 was used as starting material). The CTL epitope as described by Rehermann, and not present in the 19b NS-3 fragment was fused to this fragment. Both N-terminal and C-terminal fusions were constructed, since effects of the fusion on expression levels, susceptibility to proteolytic breakdown and functionality may be affected by the position of the epitope.

Using the pIGRI2NS-3 plasmid, which is an *E. coli* expression plasmid expressing the NS-3 19b fragment under control of the leftward promotor of phage lambda, as a template for PCR, NS3 19b coding sequences, fused respectively N- and C-terminally with the Rehermann CTL epitope (named NS-3 19bTn and NS-3 19bTc, respectively), were first subcloned into the pGEM-T (Promega) cloning vector giving rise to vectors pGEM-TNS-3 19bTn and pGEM-TNS-3 19bTc. The PCR-amplified sequences were verified by DNA sequence analysis.

In the case of fusing the T-cell epitope sequence to the N-terminal region of NS-3, PCR was carried out with a long sense primer carrying the CTL epitope and a short antisense primer homologous to sequences 3' of the NS-3 19b stop-codon. Primer sequences are depicted below.

Primer 9038 (Sense)

5'-GCCATGGCGACCTGCATCAACGGTGGCTGGA
CCGTTACCACGGTCGTGC GGCTGTTTGCA
CCCGTGGGGTTGCGAAGGCGGTGG-3' (SEQ ID NO 5)

Primer 1901 (Antisense) 5'-TTTTATCAG ACCGCTTCTGCG-3' (SEQ ID NO 6)

In the case of the C-terminally fused NS-3, PCR was carried out with a short sense primer homologous to sequences 5' of the NS-3 19b startcodon and a long antisense primer carrying the CTL epitope followed by in-frame stopcodons. Primer sequences are depicted below.

Primer 1052 (Sense)

5'-AGCAAACCACCAAGTGGA-3' (SEQ ID NO 7)

Primer 9039 (Antisense)

5'-CTCTAGACTATTAACCGTGGTAAACGGTCCAG
CAAACACCGTTGATGCAGGTC
GCCAGGCTGAAGTCGACTGTCTGG-3' (SEQ ID NO 8)

Starting from the coding sequences cloned into the pGEM-T vectors, the NS-3 19bT sequences are inserted into the pIGRI2 *E.coli* expression vector. For the N-terminally fused NS-3 19bT, the NS-3 19bT coding sequence was isolated as a 379 bp NcoI/SnaBI fragment and ligated with SnaBI/AllwNI and AlwNI/NcoI fragments from vector pIGRI2NS-3, resulting in the vector pIGRI2NS-3Tn. For the C-terminally fused NS-3 19bT, the NS-3 19bT coding sequence was isolated as a 585 bp SnaBI/SpeI fragment and inserted into the SnaBI/SpeI opened vector pIGRI2NS-3, resulting in the vector pIGRI2NS-3Tc.

Both pIGRI2NS-3Tn and pIGRI2NS-3Tc vectors were subsequently transformed to the *E.coli* expression strain MC1061(pAcI) and after temperature induction of the lambda $P_L$ promotor, expression levels were analysed on SDS-PAGE and Western blot, using a polyclonal rabbit anti NS-3 serum.

Amino Acid Sequence of the NS-3 19bTn Protein

MATCINGVCWTVYHGRAAVCTRG-
VAKAVDFVPVESMETTMRSPVFIDNSSP-
PAVPQTF QVAHLHAPTGSGKSTKV-
PAAYAAQGYKVLVLNPSVAATLGFGAYMSKAH
GVDPNIRTG VRTITTGAPITYSTYGKFLADGGC-
SGGAYDIIICDECHSIDSTSILGIGTV-
LDQAETAGARL VVLATATPPGSVTVPHPNIE-
EVALSSTGEIPFYGKAIPIEVIKGGRHLIFCHSKK
KCDELAA KLSGFGINAVAYYRGLDVSVIPTSGD-
VVVVATDALMTGFTGDFDSVIDCNTCVTQTVDF
S (SEQ ID NO 1)

Amino Acid Sequence of the NS-3 19bTc Protein

MGVAKAVDFVPVESMETTMRSPVFTDNS-
SPPAVPQTFQVAHLHAPTGSGKSTKVPAAY
AAQGYKVLVLNPSVAATLGFGAYMSKAH-
GVDPNIRTGVRTITTGAPITYSTYGKFLADG
GCSGGAYDIHCDECHSIDSTSILGIGTV-
LDQAETAGARLVVLATATPPGSVTVPHPNIEEV
ALSSTGEIPFYGKAIPIEVIKG-
GRHLIFCHSKKKCDELAAKLSGFGI-
NAVAYYRGLDVSVIP TSGDVVVATDALMTGFT-
GDFDSVIDCNTCVTQTVDFSLATCINGVCWTV
YHG (SEQ ID NO 2)

Nucleotide Sequence of the NS-3 19bTn Coding Region

ATGGCGACCTGCATCAACGGT-
GTTTGCTGGACCGTTTACCACGGTCGT-
GCGGCTGTT TGCACCCGTGGGGTTGCGAAG-
GCGGTGGACTTTGTACCCGTAGAGTCTATGG
AAACC ACCATGCGGTCCCCGGTCTTTACG-
GATAACTCATCTCCTCCGGCCGTACCG-
CAGACA TTCCAAGTGGCCCATCTACACG
CCCCCACTGGTAGTGGCAAGAGCAC-
TAAGGTGCCG GCTGCATATGCAGCCCAAGGG-
TACAAGGTACTTGTCCTGAACCCATC-
CGTTGCCGCC
ACCTTAGGATTCGGGGCGTATAT-
GTCTAAAGCACATGGTGTCGACCCTAA-
CATTAGA ACTGGGGTAAGGACCATCAC-
CACGGGCGCCCCCATTACGTACTCCACCTAC
GGCAA GTTTCTTGCCGACGGTGGT-
TGCTCTGGGGGCGCTTACGACATCAT-
AATATGTGATGA GTGCCACTCGATTGACT-
CAACCTCCATCTTGGGCATCGGCACCGTCCT
GGATCAGGC GGAGACGGCTGGAGCGCGGCT-
TGTCGTGCTCGCCACTGCTACACCTC-
CGGGGTCGGT CACCGTGCCACATCCCAA-
CATCGAGGAGGTGGCTCTGTCCAGCACTGGA
GAGATCCC CTTTATGGCAAAGCCATCCCCATC-
GAGGTCATCAAAGGGGGGAGGCACCTCATTTT
CTGCCATTCCAAGAAGAAATGTGAC-
GAGCTCGCCGCAAAGCTATCGGGCTTCGGAA
TCAACGCTGTAGCGTATTACCGAGGCCT-
TGATGTGTCCGTCATACCGACTAGCGGAG
ACGTCGTTGTTGTGGCAACA-
GACGCTCTAATGACGGGCTTTACCGGC-
GACITTGACT CAGTGATCGACTGTAACACAT-
GCGTCACCCAGACAGTCGACTTCAGCTAA
(SEQ ID NO 3)

Nucleotide Sequence of the NS-3 19bTc Coding Region

ATGGGGGTTGCGAAGGCGGTGGACTTTG-
TACCCGTAGAGTCTATGGAAACCACC ATGCG-
GTCCCCGGTCTTTACGGATAACT-
CATCTCCTCCGGCCGTACCGCAGACAT
TCCAAGTGGCCCATCTACACGC-
CCCCACTGGTAGTGGCAAGAGCACTAAGGTGC
CGGCTGCATATGCAGCCCAAGGGTA-
CAAGGTACTTGTCCTGAACCCATCCGTTGC

CGCCACCTTAGGATTCGGGGCGTATAT-
GTCTAAAGCACATGGTGTCGACCCTAAC ATTA-
GAACTGGGGTAAGGACCATCAC-
CACGGGCGCCCCATTACGTACTCCACCT
ACGGCAAGTTTCTTGCCGACGGTGGT-
TGCTCTGGGGGCGCTTACGACATCATAAT
ATGTGATGAGTGCCACTCGATTGACT-
CAACCTCCATCTTGGGCATCGGCACCGTC CTG-
GATCAGGCGGAGACGGCTGGAGCGCG-
GCTTGTCGTGCTCGCCACTGCTACA
CCTCCGGGGTCGGTCACCGTGCCACATC-
CCAACATCGAGGAGGTGGCTCTGTCCA
GCACTGGAGAGATCCCCTTTTATG-
GCAAAGCCATCCCCATCGAGGTCATCAAAGG
GGGGAGGCACCTCATTTCTGCCATTC-
CAAGAAGAAATGTGACGAGCTCGCCGC
AAAGCTATCGGGCTTCGGAATCAACGCT-
GTAGCGTATTACCGAGGCCTTGATGTG TCCGT-
CATACCGACTAGCGGAGACGTCGTTGT-
TGTGGCAACAGACGCTCTAATGA
CGGGCTTTACCGGCGACTTTGACTCAGT-
GATCGACTGTAACACATGCGTCACCCA
GACAGTCGACTTCAGCCTGGCGACCTG-
CATCAACGGTGTTTGCTGGACCGTTTAC CACG-
GTTAA (SEQ ID NO 4)

Example 7b

Purification of the NS-3 19bTn and NS-3 19bTc Proteins

E. coli cell pasts from erlenmeyer cultures were broken by a cell disrupter (CSL, model B) at 1.4 kbar in 50 mM TRIS, pH 8. This lysate was cleared by centrifugation (15000 g, 30 min, 4° C.). The supernatant was discarded, since both for the N- and the C-terminal construct NS3 was recovered in the pellet. This pellet turned out to be highly stable for the N-terminal construct allowing thorough washing (first wash with 2% sarcosyl, 0.5 M guanidiniumchloride and 10 mM DTT, second and third wash with 1% Triton X-100, 0.5 M guanidiniumchloride and 10 mM EDTA) before solubilisation. This was not the case for the C-terminal construct. Purification was further pursued on the N-terminal construct. The washed pellet was finally dissolved in 6 M guanidiniumchloride/50 mM Na$_2$BPO$_4$, at pH 7.2 and was sulfonated as described in Maertens et al. (PCT/EP99/02547). The sulfonated pellet was first desalted on a Sephadex G25 column to 6 M Urea/50 mM triethanolamine, pH 7.5, and finally purified by two sequential anion-exchange chromatographies in the same buffer composition. The first anion-exchange was performed on a Hyper DQ (50 µm) column (BioSpra Inc. Marlborough, Mass. USA) and the NS3 was recovered between 0.11 and 0.19 M NaCl. After dilution, these fractions were applied to a second Hyper DQ (20 µm) column (BioSpra Inc. Marlborough, Mass. USA) and the NS3 was recovered in the fractions containing 0.125 M NaCl. These fractions were desalted to 6 M Urea in PBS, pH 7.5. The final purity was estimated >90% based on SDS-PAGE followed by silver staining. The N-terminal sequencing by EDMAN degradation showed that this NS3 has an intact N-terminus, in which the desired epitope is present in the correct sequence. It was also confirmed that the methionine used for the start of translation was cleaved of as predicted.

Example 8

Construction of an E2 Protein Without Hypervariable Region I

An immunodominant homologous response has been noted to the HVR I region of E2. This response will be of little use in a vaccine approach, since a vaccine approach is a heterologous set-up (the vaccine strain is always different from the field strains). Therefore, deletion of this region would be necessary to have an E2 protein inducing antibodies against the more conserved, but less immunogenic regions of E2. By carefully analyzing the E2 leader sequence and the E2 hypervariable region the most ideal construct for expression of an E2 protein without HVR I was designed. This construct allows expression of an E2 peptide starting at position aa 409 instead of aa 384. As a leader sequence the C-terminal 20 amino acids of E1 were used. However, since the delineation of this HVR is not unambiguous, a second version was made (starting at aa 412), which has also a high probability to be cleaved at the right position.

Intermediate Construct pvHCV-99 (see also FIGS. 15 and 16)

In the expression cassette, the coding sequence of E2-715 should be preceded by an E1 leader signal peptide, starting at Met364. Therefore, in plasmid pvHCV-92 (FIG. 15), which contains the coding sequence for E2-715 HCV type 1b with the long version of the E1 signal peptide (starting at Met347), a deletion was made by a double-digestion with EcoRI and NcoI, followed by a 5'-overhang fill-in reaction with T4 DNA polymerase. Ligation of the obtained blunt ends (recirculization of the 6621 bp-fragment), resulted in plasmid pvHCV-99, which codes for the same protein (E2-715) with a shorter E1 leader signal peptide (starting at Met364). pvHCV-99 was deposited in the strain list as ICCG 3635. It should be clear that HCV or heterologous signal sequences of variable length may be used.

The plasmids pvHCV-100 and -101 should contain a deletion in the E2 sequence, i.e. a deletion of the hypervariable region I (HVR-I). In plasmid pvHCV-100, amino acids 384(His)-408(Ala) were deleted, while in plasmid pvHCV-101 aminoacids 384(His)-411(Ile) were deleted.

Construction pvHCV-100

For the construction of pvHCV-100, two oligonucleotides were designed:

HCV-pr 409 [8749]:
  5'-CTT TGC CGG CGT CGA CGG GCA GAA AAT CCA GCT CGT AA-3' (SEQ ID NO 9)

HCV-pr 408 [8750]:
  5'-TTA CGA GCT GGA TTT TCT GCC CGT CGA CGC CGG CAA AG -3' (SEQ ID NO 10)

PCR amplification (denaturation 5 min 95° C., 30 cycles of amplification consisting of annealing at 55° C., polymerization at 72° C., and denaturation at 95° C. for 1 min each, elongation for 10 min at 72° C.) of the pvHCV-99 template with Gpt-pr [3757] and HCV-pr 408 [8750] resulted in a 221 bp fragment, while amplification with HCV-pr 409 [8749] and TKr-pr [3756] resulted in a 1006 bp fragment. Both PCR fragments overlap one another by 19 nucleotides. These two fragments were assembled and amplified by PCR with the Gpt-pr [3757] and TKr-pr [3756] primers. The resulting 1200 bp fragment was digested with EcoRI and HinDIII and ligated into the EcoRI/HinIII digested pgsATA18 [ICCG 1998] vector (5558 bp).This construct, pvHCV-100, was analysed by restriction and sequence analysis, and deposited in the strainlist as ICCG 3636.

Construction pvHCV-101

For the construction of pvHCV-101, two oligonucleotides were designed:

HCV-pr 411 [8747]:
  5'-CTT TGC CGG CGT CGA CGG GCA GCT CGT AAA CAC CAA CG-3' (SEQ ID NO 11)

HCV-pr 410 [8748]:
  5'-CGT TGG TGT TTA CGA GCT GCC CGT CGA CGC CGG CAA AG-3' (SEQ D NO 12)

PCR amplification of the pvHCV-99 template with Gpt-pr [3757] and HCV-pr 410 [8748] resulted in a 221 bp fragment, while amplification with HCV-pr 411 [8747] and TKr-pr [3756] resulted in a 997 bp fragment. Both PCR fragments overlap one another by 19 nucleotides. These two fragments were assembled and amplified by PCR with the Gpt-pr [3757] and TKr-pr [3756]. The resulting 1200 bp fragment was digested with EcoRI and HinDIII and ligated into the EcoRI/HinDIII digested pgsATA18 [ICCG 1998] vector (5558 bp). This construct, pvHCV-101, was analysed by restriction and sequence analysis, and deposited in the strainlist as ICCG 3637.

All plasmids were checked by sequence analysis and deposited in the Innogenetics strainlist. For each plasmid two mini-DNA preparations (PLASmix) were made under sterile conditions and pooled. DNA concentration was determined and QA was performed by restriction analysis. Purified DNA was used to generate recombinant vaccinia virus as described in Maertens et al. (PCT/EP95/03031). The recombinant viruses vvHCV-100 and vvHCV-101 were, however, generated on WHO certified Vero cells. After two rounds of plaque purification the expression product was analysed by means of Western-blot analysis as described in Maertens et al. (PCT/EP95/03031). Proteins were visualised by a specific anti-E2 monoclonal antibody (IGH 212, which can be obtained from the inventors at Innogenetics N. V., Zwijnaarde, Belgium) of an estimated molecular weight of 69 and 37 kDa for vvHCV-100 and of 68 and 35 kDa for vvHCV-101. These molecular weights indicate the presence of both a glycosylated and non-glycosylated E2-protein, which was confirmed by treatment of the samples prior to Western-blot analysis with PNGaseF. This treatment results in the detection of only one single protein of 37 kDa and 35 kDa for vvHCV-100 and vvHCV-101, respectively. Amino Acid Sequence of the Mature E2, Derived from pvHCV-100

QKIQLVNTNGSWHINRTALNCNDSLQTG-
FFAALYKHFNSSGCPERLASCRSIDKFAQG
WGPLTYTEPNSSDQRPYCWHYAPRPC-
GIVPASQVCGPVYCFTPSPVVVGTTDRFGVPTY
NWGANDSDVLILNNTRPPRGNWFGCTWM-
NGTGFTKTCGGPPCNIGGAGNNTLTCPTDC
FRKHPEATYARCGSGPWLTPRCMVHY-
PYRLWHYPCTVNTFTIFKVRMYVGGVEHRFEAA
CNWTRGERCDLEDRDRSELSPLLSTTEW-
QILPCSFTTLPALSTGLIHLHQNIVDVQYLYG
VGSAVVSLVIK (SEQ ID NO 13)

Amino Acid Sequence of the Mature E2 Derived from pvHCV-101

QLVNTNGSWHJNRTALNCNSLQTGF-
FAALFYKHKFNSSGCPERLASCRSIDKFAQGWG
PLTYTEPNSSDQRPYCWHYAPRPCGIV-
PASQVCGPVYCFTPSPVVVGTTDRFGVPTYNW
GANDSDVLUNNTRPPRGNWFGCTWMNGT-
GFTKTCGGPPCNIGGAGNETNTLTCPTDCFR
KHPEATYARCGSGPWLTPRCMVHYPYRL-
WHYPCTVNFIFKVRMYVGGVEHRFEAAC
NWTRGERCDLEDRDRSELSPLLLSTTEW-
QILPCSFTTLPALSTGLIHLHQNIVDVQYLYGV
GSAVVSLVIK (SEQ ID NO 14)

Example 9

An E1 Particle with Further Improved Immunogenicity

As set out in example 1, the E1s protein was purified according to the protocol described in PCT/EP 95/03031 to Maertens et al. This protocol includes covalent modification of cysteines (free cysteines and cysteines involved in intermolecular bridging, the latter after reduction of these cysteine bridges using DTT) using maleimide derivates (N-ethyl maleimide and biotin-maleimide, both obtained from Sigma). As an alternative method for maleimide blocking, active halogens were also evaluated. These compounds, ie the active halogens, block free cysteines by means of alkylation. By way of example, an active halogen (iodoacetamide, Merck) was evaluated. The same protocol was used to purify E1 as described in Maertens et al. (PCT/EP 95/03031), but instead of maleimide compounds, iodoacetemide was used. The E1s protein obtained by this procedure behaved throughout the complete purification procedure similarly as the maleimide-blocked proteins. Upon final lowering of the detergent concentration to 0.05% CHAPS or switching to 0.5% betaine as described in example 1, similar particles were obtained as determined by DLS. The surprising effect was found, however, upon immunization of mice with this acetamide-modified E1s.

In total three series of 6 mice each were immunized with E1s using three injections with a three week interval, each injection consisting of 5 μg E1s at 100 μg/ml PBS and mixed with an equal volume of RIBI adjuvant (R-700). A first series received E1-maleimide formulated in 0.05% CHAPS, a second series received E1-acetamide also formulated in 0.05% CHAPS, while a third series received E1-acetamide formulated with 0.12% betaine. Finally, all mice were bled 10 days after the third immunization. End point titers (defined as the dilution of the serum still resulting in a OD 2 times higher then background values) for each animal individually were determined against E1-maleimide and E1-acetamide. FIG. 17 shows these end-point titers, presented as mean with standard deviations. Mice that received E1-maleimide mounted only an antibody response which is able to recognize maleimide-containing epitopes (no reactivity at all on E1-acetamide), mice that received E1-acetamide clearly mount an antibody response against true E1 epitopes, since the antibodies are reactive against both E1-acetamide and E1-maleimide. This was clearly demonstrated in an additional experiment, in which antibodies for specific regions of E1 were determined using peptides which were neither modified with acetamide nor with maleimide. The results, as shown in FIG. 18, demonstrate that the mice immunized with E1-acetamide (CHAPS and betaine formulated) do mount an antibody response which is able to recognize the peptides V1V2, V2V3, V3V4, V5C4, C4V6. As V6 was not part of E1s, we can conclude that antibodies were mounted against C4, V3 (V3V4 is positive while V4V5 is not) and V1V2. Mice immunized with E1s-maleimide mount only a very low response against the V1V2 and V2V3 peptides. This stresses once more the fact that the reasonably high titer measured for these mouse antibodies against the maleimide-E1s is mainly directed against maleimide-dependent epitopes. In addition, we were able to prove that the E1s-acetamide induced response is partially of the Th1 type, since a substantial amount of the induced antibodies is of the IgG2(a+b) subtype. The amount of IgG2 is even higher for the betaine formulation compared to the CHAPS formulation (FIG. 19). From these results it is concluded that HCV envelope proteins, in which at least one cysteine (but potentially more than one cysteine) is alkylated, are extremely immunogenic proteins.

Consequently, the acetamide-modified E1 formulated in betaine was also used to reboost the chimpanzees Phil and Ton. Both chimpanzees were immunized again with two consecutive intramuscular immunisations with a three week time interval (50 μg E1 mixed with RIBI adjuvant as for the examples 4 and 5). As can be judged from FIGS. 20 and 21, the anti-E1 response could indeed be boosted again, and this to higher levels than obtained in the previous immunisations after two injections. This titration was performed against a standard, which is a mixture of three human high titre anti-E1 sera (obtained from chronic HCV carriers). The anti-E1 titer of these sera was defined as one unit/ml. In chimpanzee Phil (FIG. 20), titers twice as high as in human carriers were induced only after two immunizations. In chimpanzee Ton (FIG. 21), titers up to 140-fold higher were induced. This stresses once more the high immunogenecity of these E1-particles.

Example 10

Alkylated E1 has Superior Qualities for Diagnostic use

The E1s-acetamide as described in example 9 was further evaluated as antigen for the detection of anti-E1 antibodies in serum samples from human chronic HCV carriers. By way of example these antigens were bound to LIA-membranes, and strips were processed essentially as described in Zrein et al. (1998). Serum samples from 72 blood donors were evaluated first, in order to determine the optimal concentration of the E1 antigen which can be used in the assay in order to exclude "false" positives. For E1s-maleimide, this concentration proved to be 8 μg/ml, while for E1s-acetamide a concentration up to 50 μg/ml did not result in false positive results (no samples showing a relative color staining above 0.5). Using 8 and 50 μg/ml, respectively, for E1s-maleimide and E1s-acetamide 24 sera of HCV chronic carriers were screened for antibodies against E1s. As shown in Table 6, the E1s-acetamide clearly results in more samples scoring positive (67% versus 38% for E1s-maleimide). No sample was found which only scored positive on E1s-maleimide. For samples scoring positive both on E1s-maleimide and on E1s-acetamide, the reactivity on the latter is higher. From this example it can be concluded that alkylated envelope proteins of HCV are better antigens to detect human antibodies than maleimide-modified envelope proteins.

Example 11

Production of Mixed Particles Containing E1 and E2

E1s and E2s (vvHCV-44) were produced and purified as described in Maertens et al. PCT/EP95/030301 except for the fact the maleimide-modificiation was replaced by alkylation using iodoacetamide. E1s and E2s in 3% empigen alone or as an equimolar mixture were injected on a Superdex-200 PC 3.2/30 column equilibrated in PBS/0.2% CHAPS. This column is designed to use with the SMART™ HPLC equipment from Pharmacia LKB (Sweden). The fractions were screened by means of three different sandwich ELISAs. For these ELISAs, E1-(IGH 207) and E2-(IGH 223) specific monoclonals were coated at 2 μg/ml. Fractions of the gel filtration were incubated in a 1/2500 dilution. Two other E1 (IGH 200) and E2 (IGH 212) monoclonals, conjugated with biotin were used for detection of the bound antigen. The streptavidin-HRP/TMB system was used to develop the bound biotin into a yellow color which was measured at 450 nm.

This ELISA system was used in a homologous (anti-E1 coating/anti-E1 detection or anti-E2 coating/anti-E2 detection) and a heterologous set-up (anti-E1 coating/anti-E2 detection). The latter theoretically only detects particles in which both E1 and E2 are incorporated. The reactive fractions were pooled, concentrated on a 10 kDa filter, and again chromatographed on Superdex-200 in PBS/0.05% CHAPS. All these fractions were tested for reactivity by using the different ELISA set-ups. As can be judged from FIG. 22, the addition of E2 to E1 does not result in a major shift in the retention time, compared to E1 alone, indicating that particles are indeed still present. These particles contain both E1 and E2, since only in this set-up the heterologous ELISA scores positive.

Example 12

Production of Mixed Particles Containing E1 from 2 Different Genotypes

E1s of genotype 1b and of genotype 4 (vvHCV-72) were produced and purified as described in Maertens et al., PCT/EP95/030301 except for the fact the maleimide-modificiation was replaced by alkylation using iodoacetamide for the genotype 1b. E1s-1b and E1s-4 in 3% empigen alone or as an equimolar mixture were injected on a Superdex-200 PC 3.2/30 column equilibrated in PBS/0.2% CHAPS. This column is designed to use with the SMART™ BPLC equipment from Pharmacia LKB (Sweden). The major protein containing fractions were pooled, concentrated on a 10 kDa filter, and again chromatographed on Superdex-200 in PBS/0.05% CHAPS. All these fractions were tested for reactivity by using an ELISA set-up which should only detect particles containing E1 from both genotypes. For this ELISA streptavidin was coated at 2 μg/ml. Fractions of the gel filtration were incubated in a 1/2500 dilution. An E1 monoclonal antibody (IGH 200) which only recognizes E1 from genotype 1 and 10 was used for detection of the bound antigen. The goat-anti-mouse-HRP/TMB system was used for development of the assay into a yellow color which was measured at 450 nm. As can be judged from FIG. 23, the addition of E1-4 to E1-1b does not result in a major shift in the retention time of the proteins, indicating that particles are indeed still present. These particles contain both E1 proteins, ie E1s of genotype 1b and genotype 4, since only in this set-up the ELISA scores positive.

LIST OF REFERENCES

Deleersnyder V., Pillez A., Wychowski C., Blight K., Xu J., Hahn Y. S., Rice C. M., Dubuisson J. Formation of native hepatitis C virus glycoprotein complexes. J. Virol. 1997: 71: 697–704.

Diepolder H M, Zachoval R, Hoffmann R M, Wierenga E A, Santantonio T, Jung M C, Eichenlaub D, Pape G R. Possible mechanism involving T-lymphocyte response to non-structural protein 3 in viral clearance in acute hepatitis C virus infection. Lancet 1995: 346: 1006–1007.

Diepolder H M, Gerlach J T, Zachoval R, Hoffmann R M, Jung M C, Wierenga E A, Scholz S, Santantonio T, Houghton M, Southwood S, Sette A, Pape G R. Immunodominant CD4+T-cell epitope within nonstructural protein 3 in acute hepatitis C virus infection. J. Virol., 1997: 71: 6011–6019.

Fancy, D. A., Melcher, K., Johnston, S. T. and Kodadek, T. New chemistry for the study of multiprotein complexes: the six-histidine tag as a receptor for a protein crosslinking reagent. Chem Biol (1996) 3: 551–559.

G. T. Hermanson in Bioconjugate Techniques (1996) Part I section 1.43 and section 2.2.1, Academic Press San Diego Calif., USA.

Houghton M. Immunity to HCV: The case for vaccine development. 4th International meeting on hepatitis C Virus and related viruses. Sattelite Symposium: New appraoch to prevention and therapy of HCV infection. Mar. 7, 1997, Kyoto, Japan.

Leroux-Roels G, Esquivel C A, DeLeys R, Stuyver L, Elewaut A, Philippe J, Desombere I, Paradijs J, Maertens G Lymphoproliferative responses to hepatitis C virus core, E1, E2, and NS3 in patients with chronic hepatitis C infection treated with interferon alfa. Hepatology 1996: 23: 8–16.

Maertens G. and Stuyver L. Genotypes and genetic variation of hepatitis C virus. In: The molecular medicine of viral hepatitis. Ed: Harrison T. J. and Zuckerman A. J. 1997.

Major M. E. and Feinstone S. M. The molecular virology of hepatitis C. Hepatology 1997: 25:1527–1538.

Maertens G., Depl a E., Ducatteeuw A., Vandeponseele P., Bosman F., Venneman A., de Martynoff G., Stuyver L., Dekeyser F., Vandeperre B., Zrein M. And Buyse M.-A. Hepatology 1997:26: 186A.

Rehermann B, Chang K M, McHutchinson J, Kokka R, Houghton M, Rice C M, Chisari F V. Differential cytotoxic T-lymphocyte responsiveness to the hepatitis B and C viruses in chronically infected patients. J Virol 1996 70: 7092–7102.

Rehermann B, Takaki A, Liebetrau A, Luda S, Seifert U, Salha K, Manns M, Wiese M. Characterization of the cytotoxic and helper T cell response in patients 18 years after a single source outbreak of HCV infection. Hepatology, 1997:26: 406A Sambrook, J., Fritsch, E. F. and Maniatis, T. (1989) Molecular Cloning, a laboratory manual, second edition. Cold Spring Harbor University Press, Cold Spring Harbor, N.Y. USA van Doorn L J, Kleter B. Pike I, Quint W. Analysis of hepatitis C virus isolates by serotyping and genotyping. J Clin Microbiol 1996; 34: 1784–1787.

Villa E., Buttafoco P., Grottola A., Scarcelli A., Giannini F., Manerti F. Neutrtalizing antibodies against HCV: liver transplant as an experimental model. J. Hepatol. 1998: 28:

Weiner A J, Erickson A L, Kansopon J, Crawford K, Muchmore E, Houghton M, Walker C M Association of cytotoxic T lymphocyte (CTL) escape mutations with persistent hepatitis C virus (HCV) infection. Princess Takamatsu Symp, 1995: 25: 227–235.

Yi M., Nakamoto Y., Kaneko S., Yamashita T., Murakami S. Delineation of regions important for heteromeric association of Hepatitis C virus E1 and E2. Virol. 1997a: 231: 119–129.

Zauberman, A., Nussbaum, O., Ilan, E., Eren, R., Ben-Moshe, O., Arazi, Y., Berre, S., Lubin, I., Shouval, D., Galun, E., Reisner, Y. and Dagan, S. The trimera mouse system: a mouse model for hepatitis C infection and evaluation of therapeutic agents. Jun. 6–9, 1999; Oral 4.3. In: 6th International Symposium on Hepatitis C & Related Viruses. Bethesda USA Zrein, M., Louwagie, J., Boeykens, H., Govers, L., Hendrickx, G., Bosman, F., Sablon, E., Demarquilly, C., Boniface, M. and Saman, E. (1998) Assessment of a new immunoassay for serological confirmation and discrimination of human T-cell lymphotropic virus infections. Clin. Diagn. Lab. Imm. 5: 45–49.

TABLE 1

The E1s consensus sequence of HCV-B

| AA Position* | 200 | 233 | 235 | 251 | 253 | 271 | 293 | 298 | 304 | 313 | 314 | 322 |
|---|---|---|---|---|---|---|---|---|---|---|---|---|
| Region | V1 | V3 | V3 | V4 | V4 | HR | HR | V5 | C4 | C4 | C4 | C4 |
| HCV-J | I | S | F | S | I | L | F | Y | — | V | S | — |
| HCV-B con | M | N | S | A | V | F | I | H | C | I | T | M |
| HCCl9A | — | — | — | — | — | L | — | — | — | — | — | — |
| HCCl9B | — | D | — | — | — | — | — | — | Y | — | — | — |
| HCCl9C | — | — | — | — | — | — | — | — | — | — | — | T |
| HCCl10A | — | — | — | — | — | — | — | — | — | — | — | — |
| HCCl10B | — | D | — | — | I | — | — | — | — | — | — | — |
| HCCl11A | — | — | — | — | — | — | — | — | — | — | — | — |
| HCCl11B | — | — | — | — | — | — | — | — | — | — | — | — |
| HCCl14 | — | — | — | — | — | — | — | — | — | — | — | — |
| HCCl17 | — | — | — | — | I | — | — | — | — | — | — | — |

*Positions between aa 192 and 326 of E1s which are completely conserved are not indicated

TABLE 2

The E1s vaccine sequence aligned with the HCV sequence of the virus present in the chronic carriers

```
           192                                                         259
Ton (1a)   YQVRNSTGLYHVTNDCPNSSIVYEAADAILHTPGCVPCVREGNASRCWVAMTPTVATRDGKLPTTQLR
              *  ** *     *      * *           * *    *   * * ****   **
E1 vaccin  YEVRNVSGMYHVTNDCSNSSIVYEAADMIMHTPGCVPCVRENNSSRCWVALTPTLAAPNASVPTTTIR
              *          *                    *           *            *
Phil (1b)  YEVRNVSGVYHVTNDCSNASIVYEAADMIMHTPGCVPCVREGNSSRCWVALTPTLAARNVSVPTTTIR
           260                                                         326
Ton (1a)   RHIDLLVGSATLCSALYVGDLCGSVFLVGQLFTFSPRRHWTTQECNCSMYPGHITGHRMAWDMMMNW  (SEQ ID NO 15)
              *    * **  *                 *       * * *   *
E1 vaccin  RHVDLLVGAAAFCSAMYVGDLCGSVFLVSQLFTISPRRHETVQDCNCSIYPGHITGHRMAWDMMMNW  (SEQ ID NO 16)
              *                               *                **
Phil (1b)  RHVDLIVGAAAFCSAMYVGDLCGSVFLVSQLFTFSPRRHETVQDCNCSIYPGHVSGHRMAWDMMMNW  (SEQ ID NO 17)
```

TABLE 3

Changes induce by therapeutic vaccination (6 × 50 μg E1s)

| | Ton (subtype 1a) Before | After | Phil (subtype 1b) Before | After |
|---|---|---|---|---|
| Serum | | | | |
| E1Ab titer | 0 | 30000 | 0 | 14500 |
| HCV RNA titer (10⁵) | 2–3 | no change | 2–4 | no change |
| ALT(IU) | 85 ± 11 | 62 ± 6 | 44 ± 4 | 37 ± 6 |
| Liver | | | | |
| Antigen staining | strongly positive | negative | strongly positive | negative |
| Histology | CAH | CPH | CAH | CPH |
| Portal inflammation | light | none | severe | moderate |
| Lobular hepatitis | moderate | minimal | severe | moderate |
| Interface hepatitis | + | − | + | − |
| Histological activity | 4 | 1–2 | 6–8 | 2–3 |

TABLE 4

| E1 peptides | SEQ ID NO | Geno-type | name | # | aa |
|---|---|---|---|---|---|
| YEVRNVSGIYHVTNDC SNSSIVYEAADMIMHT PGC | 18 | 1b | V1V2 | 888 | 192–226 |
| IVYEAADMIMHTPGCV PCVRENNSSRCWV | 19 | 1b | V2V3 | 1036 | 212–244 |
| VRENNSSRCWVALTPLA ARNASVPTTTIRRHVD | 20 | 1b | V3V4 | 1022 | 230–263 |
| HVDLLVGAAAFCSAMY VGDLCGSVFLVSQL | 21 | 1b | HR | 1150 | 261–290 |
| SQLFTISPRRHETVQDCN CSIYPGHITGHRMAWD MMMNWS | 22 | 1b | V5C4 | 1176 | 288–327 |
| SIYPGHITGHRMAWDM MMNWSPTTALVVSQLL RI | 23 | 1b | C4V6 | 1039 | 307–340 |

TABLE 5 aa 1188
\*
MATCINGVCWTVYHGRAAVC        (SEQ ID NO 24)
TRGVAK . . . proposed sequence
GGPLLCPAGHAVGIFRAAVC        (SEQ ID NO 25)
TRGVAK . . . natural sequence
double underlined: minimal CTL epitope
single underlined: additional surrounding
natural amino acids

TABLE 5-continued

At the C-terminus the epitope and its
surrounding may be linked directly.

VDFSLATCINGVCWTVYHG        Proposed sequence (SEQ ID NO 26)

VDFSLDPTFTIETITLPQD        Natural sequence (SEQ ID NO 27)

\*
aa 1468

TABLE 6

| antigen μg/nil | E1s-maleimide 8 | E1s-acetamide 50 |
|---|---|---|
| 17758 | 2 | 4 |
| 17761 | 0 | 0.5 |
| 17763 | 0 | 0.5 |
| 17766 | 0 | 1 |
| 17767 | 0 | 1 |
| 17771 | 0.5 | 2 |
| 17773 | 0 | 0 |
| 17775 | 0 | 0.5 |
| 17776 | 0 | 0.5 |
| 17777 | 0.5 | 2 |
| 17779 | 0 | 0 |
| 17784 | 3 | 4 |
| 17785 | 0.5 | 2 |
| 17786 | 0 | 2 |
| 17789 | 2 | 4 |
| 17790 | 2 | 4 |
| 17794 | 2 | 4 |
| 17795 | 0 | 1 |
| 17796 | 0 | 0 |
| 17798 | 0 | 0.5 |
| 17820 | 2 | 4 |
| 17825 | 2 | 3 |
| 17827 | 2 | 4 |
| 17842 | 1 | 2 |
| #pos | 9 | 16 |
| % pos | 38 | 67 |

What is claimed is:

1. An oligomeric particle having a diameter of 1 to 100 nanometer and consisting of HCV envelope proteins, or parts thereof, wherein at least one cysteine of said HCV envelope proteins, or part thereof, is alkylated.

2. Oligomeric particle according to claim 1 having a diameter of 2 to 40 nanometer.

3. Oligomeric particle according to claim 1, in which the amino acid sequence of the HCV envelope protein, or parts thereof is derived from an isolate-, subtype-, species-, or genus-consensus amino acid sequence.

4. Oligomeric particle according to claim 1, wherein said envelope proteins are HCV E1 proteins or parts thereof.

5. An oligomeric particle of claim 1, wherein said envelope proteins are HCV E1s proteins or parts thereof.

6. An oligomeric particle of claim 1, wherein said envelope proteins are HCV E2 proteins or parts thereof.

7. An oligomeric particle consisting essentially of HCV envelope proteins and having a diameter of 1 to 100 nanometer, wherein said envelope proteins are SEQ ID No 13 and/or SEQ ID No 14, or parts thereof.

8. Oligomeric particle according to claim 1, wherein said envelope proteins are encoded by an isolate nucleotide consensus sequence, subtype nucleotide consensus sequence, species nucleotide consensus sequence, or genus nucleotide consensus sequence, or parts thereof.

9. An oligomeric particle consisting essentially of HCV envelope proteins and having a diameter of 1 to 100 nanometer, wherein said envelope proteins are a mixture of HCV E1, HCV E1s, HCV E2 proteins and/or SEQ ID No 13 and/or SEQ ID No 14, or parts thereof.

10. An oligomeric particle consisting essentially of HCV envelope proteins and having a diameter of 1 to 100 nanometer, wherein said envelope proteins, or parts thereof, are derived from different HCV strains or genotypes.

11. An oligomeric particle consisting essentially of HCV envelope proteins and having a diameter of 1 to 100 nanometer, wherein said envelope proteins, or parts thereof, are a mixture consisting of HCV envelope proteins from one strain or genotype of HCV and at least one other strain or genotype of HCV.

12. The oligomeric particle according to any of claims 5, 7, 9, 10 and 11 wherein at least one cysteine of said HCV envelope protein or part thereof is alkylated.

13. A composition comprising an oligomeric particle according to claim 12 and a carrier.

14. A method of inducing immunity against HCV in a chronic HCV carrier comprising administering an oligomeric particle according to claim 1 to said carrier.

15. The oligomeric particle according to claim 1, or composition containing the same, for inducing immunity against HCV in chronic HCV carriers.

16. Composition comprising an oligomeric particle of claim 1, 7, 9, 10, or 11, and at least one of an excipient, diluent, carrier or adjuvant.

17. Composition according to claim 16, which also comprises HCV core, P7, E1, E2, NS2, NS3, NS4A, NS4B, NS5A and/or NS5B protein, or parts thereof.

18. Composition according to claim 17 wherein said NS3 protein, or parts thereof, have an amino acid sequence given by SEQ ID No 1 or SEQ D No 2.

19. A method of manufacturing an HCV vaccine composition comprising mixing an oligomeric particle according to claim 1 and a diluent.

20. A method of inducing immunity against HCV in chronic HCV carriers comprising administering an oligomeric particle consisting essentially of HCV envelope proteins and having a diameter of 1 to 100 nanometer to said carrier.

21. The oligomeric particle or the composition according to claim 1 for use as an HCV vaccine.

22. An oligomeric particle consisting essentially of HCV envelope proteins and having a diameter of 1 to 100 nanometer or composition containing the same for inducing immunity against HCV in chronic HCV carriers.

23. An oligomeric particle consisting essentially of HCV envelope proteins and having a diameter of 1 to 100 nanometer, obtainable by a method characterized by the following steps:

I purifying HCV envelope proteins in solution, with an alkylating agent, and optionally, at least one of a disulphide bond cleavage agent and a first detergent, II replacing said solution of said purified HCV envelope proteins with a second detergent or salt, resulting in oligomeric particles, III purifying the oligomeric particles formed after step II, and optionally further reducing the concentration of the second detergent or salt of step II.

24. Oligomeric particle according to claim 23, wherein said optionally first detergent is Empigen-BB, wherein the second detergent of step II is CHAPS, octylglucoside, Tween, or any other detergent, and wherein said salt is betaine.

25. Oligomeric particle according to claim 24, wherein said Empigen-BB is used at a concentration of 1% to 10% and wherein said CHAPS or Tween is used at a concentration of 0.01% to 10%, or said betaine is used at a concentration of 0.01% to 10%.

26. Method to produce an oligomeric particleconsisting essentially of HCV envelope proteins and having a diameter of 1 to 100 nanometer, characterized by the following steps:

I purifying HCV envelope proteins in solution with an alkylating agent, and, optionally, at least one of a disulphide bond cleavage agent and a first detergent, II replacing said solution of said purified HCV envelope proteins with a second detergent or salt, resulting in oligomeric particles.

III purifying the oligomeric particles formed after step II, and optionally further reducing the concentration of the second detergent or salt of step II.

27. Method to produce an oligomeric particle according to claim 26, wherein said optionally first detergent is Empigen-BB, wherein the second detergent of step II is CHAPS, octylglucoside, Tween, or any other detergent, and wherein said salt is betaine.

28. Method to produce an oligomeric particle according to claim 26, wherein said Empigen-BB is used at a concentration of 1% to 10% and,wherein said CHAPS or Tween is used at concentrations of 0.01% to 10%, or said betaine is used at a concentration of 0.01% to 10%.

* * * * *

UNITED STATES PATENT AND TRADEMARK OFFICE
CERTIFICATE OF CORRECTION

PATENT NO.    : 6,635,257 B1
DATED         : October 21, 2003
INVENTOR(S)   : Depla et al.

It is certified that error appears in the above-identified patent and that said Letters Patent is hereby corrected as shown below:

Title page,
Item [75], Inventors, delete "Opwiik" after "Bosman" and insert --Opwijk -- therefor.
Item [73], Assignee, delete "Innogentics" and insert -- Innogenetics -- therefor.

Column 6,
line 49, delete "PCS" and insert -- FCS -- therefor.

Column 11,
line 28, delete "octylglucaside" and insert -- octylglucoside -- therefor.

Column 17,
line 67, delete "octylglucaside" and insert -- octylglucoside -- therefor.

Column 18,
Line 29, delete "Notebly" and insert -- Notably -- therefor.

Column 19,
line 41, delete "RLBI" and insert -- RIBI -- therefor.

Column 21,
line 53, delete "V1" and insert -- V1 -- therefor.

Column 23,
SEQ ID NO 5, line 34, delete "GCCATGGCGACCTGCATCAACGGTGGCTGGA" and insert -- GCCATGGCGACCTGCATCAACGGTGTTTGCTGGA -- therefor.
SEQ ID NO 5, line 35, delete "CCGTTACCACGGTCGTGCGGCTGTTTGCA " and insert -- CCGTTTACCACGGTCGTGC GGCTGTTTGCA -- therefor.

Column 24,
SEQ ID NO 1, line 3, delete "VAKAVDFVPVESMETTMRSPVFIDNSSP" and insert -- VAKAVDFVPVESMETTMRSPVFTDNSSP -- therefor.
SEQ ID NO 2, line 18, delete "GCSGGAYDIHCDECHSIDSTSILGIGTV" and insert -- GCSGGAYDIIICDECHSIDSTSILGIGTV -- therefor.
SEQ ID NO 2, line 21, delete "NAVAYYRGLDVSVIPTSGDVVVATDALMTGFT" and insert -- NAVAYYRGLDVSVIPTSGDVVVVATDALMTGFT -- therefor.
SEQ ID NO 3, line 48, delete "GAGATCCCCTTTATGGCAAAGCCATCCCCATC" and insert -- GAGATCCCCTTTTATGGCAAAGCCATCCCCATC -- therefor.
SEQ ID NO 3, line 56, delete "GACITTGACTCAGTGATCGACTGTAACACAT" and insert -- GACTTTGACTCAGTGATCGACTGTAACACAT -- therefor.

UNITED STATES PATENT AND TRADEMARK OFFICE
CERTIFICATE OF CORRECTION

PATENT NO. : 6,635,257 B1
DATED : October 21, 2003
INVENTOR(S) : Depla et al.

It is certified that error appears in the above-identified patent and that said Letters Patent is hereby corrected as shown below:

Column 25,
line 29, delete "pasts" and insert -- pastes -- therefor.
line 42, delete "Na$_2$BP0$_4$" and insert -- Na$_2$HP0$_4$ -- therefor.

Column 26,
line 55, delete "Hinlll" and insert -- HinDlll -- therefor.

Column 27,
SEQ ID NO 13, line 45, delete "CNWTRGERCDLEDRDRSELSPLLSTTEW " and insert -- CNWTRGERCDLEDRDRSELSPLLLSTTEW -- therefor.

Column 27,
SEQ ID NO 14, line 50, delete "QLVNTNGSWHJNRTALNCNSLQTGF" and insert -- QLVNTNGSWHINRTALNCNSLQTGF -- therefor.
SEQ ID NO 14, line 54, delete "GANDSDVLUNNTRPPRGNWFGCTWMNGT" and insert -- GANDSDVLILNNTRPPRGNWFGCTWMNGT -- therefor.
SEQ ID NO 14, line 55, delete "GFTKTCGGPPCNIGGAGNETNTLTCPTDCFR" and insert -- GFTKTCGGPPCNIGGAGNNTLTCPTDCFR -- therefor.
SEQ ID NO 14, line 56, delete "WHYPCTVNFIFKVRMYVGGVEHRFEAAC" and insert-- WHYPCTVNFTIFKVRMYVGGVEHRFEAAC -- therefor.

Column 30,
line 26, delete "BPLC" and insert -- HPLC -- therefor.

Column 31,
line 16, delete "Depl a" and insert -- Depla -- therefor.

Columns 31/32,
TABLE 2 (line 2),delete
"YEVRNVSGMYHVTNDCSNSSIVYEAADMIMHTPGCVPCVRENNSSRCWVALTPT
LAAPNASVPTTTIR" and insert -- YEVRNVSGMYHVTNDCSNSSIVYEAAD
MIMHTPGCVPCVRENNSSRCWVALTPTLAARNASVPTTTIR -- therefor.

Column 33,
TABLE 4 (line 6), delete "VRENNSSRCWVALTPLA " and
insert -- VRENNSSRCWVALTPTLA -- therefor

UNITED STATES PATENT AND TRADEMARK OFFICE
CERTIFICATE OF CORRECTION

PATENT NO. : 6,635,257 B1
DATED : October 21, 2003
INVENTOR(S) : Depla et al.

It is certified that error appears in the above-identified patent and that said Letters Patent is hereby corrected as shown below:

Columns 33/34,
TABLE 5, delete "MATCINGVCWTVYHGRAAVCTRGVAK" of SEQ ID NO 24, and insert therefor -- M<u>ATCINGVCWTV</u>Y<u>HG</u>RAAVCTRGVAK -- therefor.

Column 34,
TABLE 6, delete "VDFSLATCINGVCWTVYHG" of SEQ ID NO 26, and insert therefor -- VDFS<u>LATCI NGVCWTVYHG</u> -- therefor.
TABLE 6, delete "nil" in the heading, and insert -- ml -- therefor.

Signed and Sealed this

Seventh Day of September, 2004

JON W. DUDAS
*Director of the United States Patent and Trademark Office*

UNITED STATES PATENT AND TRADEMARK OFFICE
CERTIFICATE OF CORRECTION

PATENT NO.    : 6,635,257 B1
DATED         : October 21, 2003
INVENTOR(S)   : Depla et al.

It is certified that error appears in the above-identified patent and that said Letters Patent is hereby corrected as shown below:

Title page,
Item [75], Inventors, delete "Opwiik" after "Bosman" and insert --Opwijk -- therefor.
Item [73], Assignee, delete "Innogentics" and insert -- Innogenetics -- therefor.

Column 6,
line 49, delete "PCS" and insert -- FCS -- therefor.

Column 11,
line 28, delete "octylglucaside" and insert -- octylglucoside -- therefor.

Column 17,
line 67, delete "octylglucaside" and insert -- octylglucoside -- therefor.

Column 18,
Line 29, delete "Notebly" and insert -- Notably -- therefor.

Column 19,
line 41, delete "RLBI" and insert -- RIBI -- therefor.

Column 21,
line 53, delete "V1" and insert -- V1 -- therefor.

Column 23,
SEQ ID NO 5, line 34, delete "GCCATGGCGACCTGCATCAACGGTGGCTGGA" and insert -- GCCATGGCGACCTGCATCAACGGTGTTTGCTGGA -- therefor.
SEQ ID NO 5, line 35, delete "CCGTTACCACGGTCGTGCGGCTGTTTGCA " and insert -- CCGTTTACCACGGTCGTGC GGCTGTTTGCA -- therefor.

Column 24,
SEQ ID NO 1, line 3, delete "VAKAVDFVPVESMETTMRSPVFIDNSSP" and insert -- VAKAVDFVPVESMETTMRSPVFTDNSSP -- therefor.
SEQ ID NO 2, line 18, delete "GCSGGAYDIHCDECHSIDSTSILGIGTV" and insert -- GCSGGAYDIIICDECHSIDSTSILGIGTV -- therefor.
SEQ ID NO 2, line 21, delete "NAVAYYRGLDVSVIPTSGDVVVATDALMTGFT" and insert -- NAVAYYRGLDVSVIPTSGDVVVVATDALMTGFT -- therefor.
SEQ ID NO 3, line 48, delete "GAGATCCCCTTTATGGCAAAGCCATCCCCATC" and insert -- GAGATCCCCTTTTATGGCAAAGCCATCCCCATC -- therefor.
SEQ ID NO 3, line 56, delete "GACITTGACTCAGTGATCGACTGTAACACAT" and insert -- GACTTTGACTCAGTGATCGACTGTAACACAT -- therefor.

UNITED STATES PATENT AND TRADEMARK OFFICE
CERTIFICATE OF CORRECTION

PATENT NO. : 6,635,257 B1
DATED : October 21, 2003
INVENTOR(S) : Depla et al.

It is certified that error appears in the above-identified patent and that said Letters Patent is hereby corrected as shown below:

Column 25,
line 29, delete "pasts" and insert -- pastes -- therefor.
line 42, delete "Na$_2$BP0$_4$" and insert -- Na$_2$HP0$_4$ -- therefor.

Column 26,
line 55, delete "Hinlll" and insert -- HinDlll -- therefor.

Column 27,
SEQ ID NO 13, line 45, delete "CNWTRGERCDLEDRDRSELSPLLSTTEW " and insert -- CNWTRGERCDLEDRDRSELSPLLLSTTEW -- therefor.

Column 27,
SEQ ID NO 14, line 50, delete "QLVNTNGSWHJNRTALNCNSLQTGF" and insert -- QLVNTNGSWHINRTALNCNSLQTGF -- therefor.
SEQ ID NO 14, line 54, delete "GANDSDVLUNNTRPPRGNWFGCTWMNGT" and insert -- GANDSDVLILNNTRPPRGNWFGCTWMNGT -- therefor.
SEQ ID NO 14, line 55, delete "GFTKTCGGPPCNIGGAGNETNTLTCPTDCFR" and insert -- GFTKTCGGPPCNIGGAGNNTLTCPTDCFR -- therefor.
SEQ ID NO 14, line 56, delete "WHYPCTVNFIFKVRMYVGGVEHRFEAAC" and insert-- WHYPCTVNFTIFKVRMYVGGVEHRFEAAC -- therefor.

Column 30,
line 26, delete "BPLC" and insert -- HPLC -- therefor.

Column 31,
line 16, delete "Depl a" and insert -- Depla -- therefor.

Columns 31/32,
TABLE 2 (line 2),delete
"YEVRNVSGMYHVTNDCSNSSIVYEAADMIMHTPGCVPCVRENNSSRCWVALTPT LAAPNASVPTTTIR" and insert -- YEVRNVSGMYHVTNDCSNSSIVYEAAD MIMHTPGCVPCVRENNSSRCWVALTPTLAARNASVPTTTIR -- therefor.

Column 33,
TABLE 4 (line 6), delete "VRENNSSRCWVALTPLA " and
insert -- VRENNSSRCWVALTPTLA -- therefor

UNITED STATES PATENT AND TRADEMARK OFFICE
CERTIFICATE OF CORRECTION

PATENT NO. : 6,635,257 B1
DATED : October 21, 2003
INVENTOR(S) : Depla et al.

It is certified that error appears in the above-identified patent and that said Letters Patent is hereby corrected as shown below:

Columns 33/34,
TABLE 5, delete "MA<u>TCINGVCWT</u>VYHGRAAVCTRGVAK" of SEQ ID NO 24, and insert therefor -- M<u>ATCINGVCWTVYHG</u>RAAVCTRGVAK -- therefor.

Column 34,
TABLE 6, delete "VDFS<u>LATCINGVCWTVYHG</u>" of SEQ ID NO 26, and insert therefor -- VDFS<u>LATCI NGVCWTVYHG</u> -- therefor.
TABLE 6, delete "nil" in the heading, and insert -- ml -- therefor.

This certificate supersedes Certificate of Correction issued September 7, 2004.

Signed and Sealed this

Twenty-second Day of February, 2005

JON W. DUDAS
*Director of the United States Patent and Trademark Office*